US011149267B2

(12) United States Patent
Wang et al.

(10) Patent No.: US 11,149,267 B2
(45) Date of Patent: Oct. 19, 2021

(54) FUNCTIONAL GENOMICS USING CRISPR-CAS SYSTEMS, COMPOSITIONS, METHODS, SCREENS AND APPLICATIONS THEREOF

(71) Applicants: The Broad Institute, Inc., Cambridge, MA (US); Massachusetts Institute of Technology, Cambridge, MA (US); Whitehead Institute for Biomedical Research, Cambridge, MA (US)

(72) Inventors: Tim Wang, Boston, MA (US); David Sabatini, Cambridge, MA (US); Eric Lander, Cambridge, MA (US)

(73) Assignees: The Broad Institute, Inc., Cambridge, MA (US); Massachusetts Institute of Technology, Cambridge, MA (US); Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 15/141,348

(22) Filed: Apr. 28, 2016

(65) Prior Publication Data

US 2016/0251648 A1 Sep. 1, 2016

Related U.S. Application Data

(63) Continuation-in-part of application No. PCT/US2014/062558, filed on Oct. 28, 2014.

(60) Provisional application No. 61/961,980, filed on Oct. 28, 2013, provisional application No. 61/963,643, filed on Dec. 9, 2013, provisional application No. 62/069,243, filed on Oct. 27, 2014.

(51) Int. Cl.
| | | |
|---|---|---|
| *C12N 15/10* | (2006.01) | |
| *C12N 15/90* | (2006.01) | |
| *C12N 15/63* | (2006.01) | |
| *C12N 15/113* | (2010.01) | |

(52) U.S. Cl.
CPC ....... *C12N 15/102* (2013.01); *C12N 15/1082* (2013.01); *C12N 15/1093* (2013.01); *C12N 15/113* (2013.01); *C12N 15/63* (2013.01); *C12N 15/907* (2013.01); *C12N 2310/10* (2013.01); *C12N 2310/20* (2017.05); *C12N 2320/11* (2013.01); *C12N 2330/31* (2013.01)

(58) Field of Classification Search
None
See application file for complete search history.

(56) References Cited

U.S. PATENT DOCUMENTS

| 4,873,316 A | 10/1989 | Meade et al. | |
|---|---|---|---|
| 8,697,359 B1 * | 4/2014 | Zhang | C12N 15/85 424/94.1 |
| 8,771,945 B1 | 7/2014 | Zhang | |
| 8,795,965 B2 | 8/2014 | Zhang | |
| 8,865,406 B2 | 10/2014 | Zhang | |
| 8,871,445 B2 | 10/2014 | Cong et al. | |
| 2003/0186238 A1 | 10/2003 | Allawi et al. | |
| 2004/0111221 A1 | 10/2004 | Beattie | |
| 2006/0234247 A1 | 10/2006 | Puttaraju et al. | |
| 2007/0016012 A1 | 1/2007 | Hartlep | |
| 2010/0055798 A1 | 3/2010 | Battersby | |
| 2010/0076057 A1 | 3/2010 | Sontheimer et al. | |
| 2011/0016540 A1 | 1/2011 | Weinstein | |
| 2011/0059502 A1 | 3/2011 | Chalasani | |
| 2011/0189776 A1 | 8/2011 | Terns et al. | |
| 2011/0223638 A1 | 9/2011 | Wiedenheft et al. | |
| 2011/0239315 A1 | 9/2011 | Bonas et al. | |
| 2012/0029891 A1 | 2/2012 | Behlke et al. | |
| 2013/0130248 A1 | 5/2013 | Haurwitz et al. | |
| 2014/0068797 A1 | 3/2014 | Doudna et al. | |
| 2014/0179006 A1 | 6/2014 | Zhang | |
| 2014/0179770 A1 | 6/2014 | Zhang et al. | |
| 2014/0186843 A1 | 7/2014 | Zhang et al. | |
| 2014/0186919 A1 | 7/2014 | Zhang et al. | |
| 2014/0186958 A1 | 7/2014 | Zhang et al. | |

(Continued)

FOREIGN PATENT DOCUMENTS

| EP | 0264166 A1 | 4/1988 |
|---|---|---|
| EP | 2591770 | 5/2013 |

(Continued)

OTHER PUBLICATIONS

Sorek et al., "CRISPR-Mediated Adaptive Immune Systems in Bacteria and Archaea" 82 Annual Review of Biochemistry 237-266 (2013).*

(Continued)

*Primary Examiner* — Nancy J Leith

(74) *Attorney, Agent, or Firm* — Johnson, Marcou, Isaacs & Nix, LLC; F. Brent Nix, Esq.; Rachel D. Rutledge, Esq.

(57) ABSTRACT

The present invention generally relates to libraries, kits, methods, applications and screens used in functional genomics that focus on gene function in a cell and that may use vector systems and other aspects related to Clustered Regularly Interspaced Short Palindromic Repeats (CRISPR)-Cas systems and components thereof. The present invention also relates to rules for making potent single guide RNAs (sgRNAs) for use in CRISPR-Cas systems. Provided are genomic libraries and genome wide libraries, kits, methods of knocking out in parallel every gene in the genome, methods of selecting individual cell knock outs that survive under a selective pressure, methods of identifying the genetic basis of one or more medical symptoms exhibited by a patient, and methods for designing a genome-scale sgRNA library.

19 Claims, 17 Drawing Sheets

Specification includes a Sequence Listing.

(56) References Cited

U.S. PATENT DOCUMENTS

| | | |
|---|---|---|
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2016/0272965 A1* | 9/2016 | Zhang ............... C12N 15/1082 |

FOREIGN PATENT DOCUMENTS

| | | | |
|---|---|---|---|
| EP | 2764103 | 8/2014 | |
| EP | 2771468 | 9/2014 | |
| WO | 2008108989 | 9/2008 | |
| WO | 2010054108 | 5/2010 | |
| WO | 2011146121 | 11/2011 | |
| WO | 2012164565 | 12/2012 | |
| WO | 2013082519 | 6/2013 | |
| WO | 2013098244 | 7/2013 | |
| WO | 2013130824 | 9/2013 | |
| WO | 2013141680 | 9/2013 | |
| WO | 2013142578 | 9/2013 | |
| WO | 2013176772 | 11/2013 | |
| WO | 2014018423 A2 | 1/2014 | |
| WO | 2014065596 | 5/2014 | |
| WO | 2014089290 | 6/2014 | |
| WO | 2014093479 | 6/2014 | |
| WO | 2014093595 A1 | 6/2014 | |
| WO | 2014093622 | 6/2014 | |
| WO | 2014093622 A2 | 6/2014 | |
| WO | 2014093635 | 6/2014 | |
| WO | 2014093655 A1 | 6/2014 | |
| WO | 2014093655 A2 | 6/2014 | |
| WO | 2014093661 | 6/2014 | |
| WO | 2014093661 A2 | 6/2014 | |
| WO | 2014093694 | 6/2014 | |
| WO | 2014093694 A1 | 6/2014 | |
| WO | 2014093701 A1 | 6/2014 | |
| WO | 2014093709 A1 | 6/2014 | |
| WO | 2014093712 | 6/2014 | |
| WO | 2014093712 A1 | 6/2014 | |
| WO | 2014093718 | 6/2014 | |
| WO | 2014093718 A1 | 6/2014 | |
| WO | 2014099744 | 6/2014 | |
| WO | 2014099750 | 6/2014 | |
| WO | 2014204724 | 12/2014 | |
| WO | 2014204725 | 12/2014 | |
| WO | 2014204727 A1 | 12/2014 | |
| WO | 2014204729 | 12/2014 | |
| WO | WO-2014204727 A1 * | 12/2014 | ......... C12N 15/1082 |
| WO | 2015065964 A1 | 5/2015 | |
| WO | 2015089419 | 6/2015 | |

OTHER PUBLICATIONS

Koonin et al., "Diversity, classification and evolution of CRISPR-Cas Systems" 37 Current Opinion in Microbiology 67-78 (2017).*
U.S. Appl. No. 61/734,256, filed Dec. 6, 2012, Fuqiang Chen.
U.S. Appl. No. 61/758,624, filed Jan. 30, 2013, Fuqiang Chen.
U.S. Appl. No. 61/761,046, filed Feb. 5, 2013, Scott Knight.
U.S. Appl. No. 61/761,422, filed Mar. 15, 2013, Scott Knight.
U.S. Appl. No. 61/735,876, filed Dec. 11, 2012, Elake A. Wiedenheft.
U.S. Appl. No. 61/799,531, filed Mar. 15, 2013, Elake A. Wiedenheft.
U.S. Appl. No. 61/738,355, filed Dec. 17, 2012, George M. Church.
U.S. Appl. No. 61/799,169, filed Mar. 13, 2012, Frashant Mali.
U.S. Appl. No. Mar. 20, 2012, Virginijus Siksnys.
U.S. Appl. No. 61/625,420, filed Apr. 17, 2012, Virginijus Siksnys.
U.S. Appl. No. 61/652,086, filed May 25, 2012, Martin Jinek.
U.S. Appl. No. 61/716,256, filed Oct. 19, 2012, Martin Jinek.
U.S. Appl. No. 61/736,527, filed Dec. 12, 2012, F. Zhang.
U.S. Appl. No. 61/757,640, filed Jan. 28, 2013, Jinek.
U.S. Appl. No. 61/794,422, filed Mar. 15, 2013, Knight.
Andreas, et al. "Enhanced efficiency through nuclear localization signal fusion on phage C31-integrase: activity comparison with Cre and FLPe recombinase in mammalian cells" Nucleic Acids Research, 2002, 30(11):2299-2306.
Asuri, et al. "Directed Evolution of Adeno-Associated Virus for Enhanced Gene Delivery and Gene Targeting in Human Pluripotent Stem Cells" Molecular Therapy, Feb. 2012, 30(2):329-338.
Al-Attar, et al., "Clustered regularly interspaced short palindromic repeats (CRISPRs): the hallmark of an ingenious antiviral defense mechanism in prokaryotes" Biol Chem., 2011, 392(4):277-289.
Baker, "Gene editing at CRISPR Speed" Nature Biotechnology, 2014, 32(4):309-312.
Banaszewska, et al. "Proprotein Convertase Subtilisin/Kexin Type 9: A New Target Molecule for Gene Therapy" Cellular & Molecular Biology Letters, Feb. 2012, 17(2):228-239.
Barrangou, "RNA-mediated programmable DNA cleavage" Nature Biotechnology, Sep. 2012, 30(9):836-388.
Bergemann, et al. "Excision of specific DNA-sequences from integrated retroviral vectors via site-specific recombination" Nucleic Acids Res., 1995, 23(21):4451-4456.
Bikard, et al. "CRISPR Interference Can Prevent Natural Transformation and Virulence Acquisition During in Vivo Bacterial Infection" Cell Host & Microbe, Aug. 2012, vol. 12:177-186.
Boch, et al. "Breaking the Code of DNA Binding Specificity of TAL-Type III Effecors" Science, 2009, 326:1509-1512.
Boch, et al. "Xanthomonas AvrBs3 Family-Type III Effectors: Discovery and Function" Annu. Rev. Phytopathol, 2010, Vo. 48:419-436.
Bogdanove, et al. "TAL Effectors:Customizable Proteins for DNA Targeting" Science, 2011, 333:1843-1846.
Briner, et al. "Guide RNA Functional Modules Direct Cas9 Activity and Orthogonality" Molecular Cell, Oct. 2014, 56:333-339.
Carroll, "A CRISPR Approach to Gene Targeting" Molecular Therapy, 2012, 20(9): 1658-1660.
Cermak, et al. Efficient design and assembly of custom TALEN and other TAL Effector-Based Constructs for DNA Targeting, Nucleic Acids Research (2011) vol. 39, No. 12, e82, p. 1-11.
Chen, et al. "Dynamic Imaging of Genomic Loci in Living Human Cells by an Optimized CRISPR/Cas System" Cell, Dec. 2013, vol. 155:1479-1491.
Jieliang Chen, et al. "An Efficient Antiviral Strategy for Targeting Hepatitis B Virus Genome Using Transcription Activator-Like Effector Nucelases" Molecular Therapy, 2014, 22(2):303-311.
Sidi Chen, et al., "Genome-wide CRISPR Screen in a Mouse Model of Tumor Growth and Metastasis," Cell, 2015, 160:1-15, http://dx.doi.org/10.1016/j.cell.2015.02.038.
Cho, et al. "Generation of Transgenic Mice" Curr Protoc Cell Biol., 2011, 19.11.doi:10.1002/0471143030. cb1911s42.
Choulika, et al., "Transfer of Single Gene-Containing Long Terminal Repeats into the Genome of Mammalian Cells by a Retroviral Vector Carrying the cre Gene and the loxP site" Journal of Virology, 1996, 70(3):1792-1798.
Christian, et al. "Targeting DNA Double-Strand Breaks With TAL Effector Nucleases" Genetics, Oct. 2010, vol. 186:757-761.
Christian, et al. "Supporting Information-Targeting DNA Double-Strand Breaks With TAL Effector Nucleases" Genetics, 2010, DOI:10.1534/110.120717:1SI-8SI.
Chylinski, et al. "The tractRNA and Cas9 Families of Type II CRISPR-Cas Immunity Systems" RNA Biology, May 2013, 10(5):726-737.
Cong, et al. "Comprehensive interrogation of natural TALE DNA-binding modules and transcriptional repressor domains" Nature Communications, 2012, 3:968, DOI:10/2038/ncomms1962.
Connor, "Scientific split—the human genome breakthrough dividing former colleagues," Science, The Independent, Apr. 25, 2014, http://www.independent.co.uk/news/science/scientific-split--the-human-genome-breakthrough-dividing-former-colleagues-9300456.html.

(56) References Cited

OTHER PUBLICATIONS

CRISPR-associated endonuclease Cas9; Oct. 21, 2012, XP002738511M, http://ibis/exam/dbfetch.jsp?id=uniprot:J7RUA5.
Dahlman, et al. "In vivo endothelial siRNA delivery using polymeric nanoparticles with low molecular weight" Nat. Nanotechnol., 2014, 9(8)648-655. doi:10.1038/nnano.2014.84.
Datensenko, et al. "Molecular memory of prior infections activates the CRISPR/Cas adaptive bacterial immunity system" Nature Communications, Jul. 10, 2012, 3:935, DOI:10.1038/ncomms1937.
Dingwall, et al. "Abstract: A Polypeptide Domain That Specifies Migration of Nucleoplasmin into The Nucleus" Cell, 1982, 30(2):449-58.
Deltcheva, et al. "CRISPR RNA maturation by trans-encoded small RNA and host Factor RNase III" Nature, Mar. 2011, vol. 471:602-609.
Deltcheva, et al. "Supplementary Information: CRISPR RNA Maturation by Trans-Encoded Small RNA and Host Factor RNase III" www.Nature.com/doi:10.1038/nature09886:1-35, 2011.
Drittanti, et al. "High throughput production, screening and anyalysis of adeno-associated viral vectors" Gene Therapy, 2000, 7:924-929.
Ebina, et al. "Harnessing the CRISPR/Cas9 system to disrupt latent HIV-1 provirus" Scientific Reports, 2013, 2:2510, doi:10.1038/srep02510.
Ellis, et al. Macromolecular Crowding: Obvious But Underappreciated, TRENDS in Biochemical Sciences, Oct. 2001, 26(10):597-604.
Ellis, et al. "Zinc-finger nuclease-mediated gene correction using single AAV vector transduction and enhanced by Food and Drug Administration-Approved Drugs" Gene Therapy, 2013, vol. 20:35-42.
Enyeart, et al., "Biotechnological applications of mobile group II introns and their reverse transcriptases: gene targeting, RNA-seq, and non-coding RNA analysis" Mobile DNA, 2014, 5:2, http://www.mobilednajournal.com/contents5/1/2.
Gabriel, et al. "An unbiased genome-wide analysis of zinc-finger nuclease specificity" Nature Biotechnology, Aug. 2011, 29(9):816-823.
Gaj, et al. "ZFN, TALEN, and CRISPR/Cas-Based Methods for Genome Engineering" Trends in Biotechnology, Jul. 2013, 31(7):397-405.
Garneau, et al. "The CRISPR-Cas bacterial immune systems cleaves bacteriophage and plasmid DNA" Nature, Nov. 2010, 468:67-71.
Gasiunas, et al. "Cas9-crRNA ribonucleoprotein complex mediates specific DNA cleavage for adaptive immunity in bacteria" PNAS, Sep. 2012, 109(39): E2579-E2586.
Geißler, et al. "Trancscriptional Activators of Human Genes with Programmable DNA-Specificity" PLone, 2011, 6(5):e19509. Doi:10.1371/hournal.pone.0019509.
Goldfarb, et al. "Synthetic peptides as nuclear localization signals" Nature, Aug. 1986, 322(14):641-644.
Grens, Enzyme Improves CRISPR A smaller Cas9 protein enables in vivo genome engineering via viral vectors, The Scientist, Apr. 1, 2015.
Gustafsson, et al. "Codon Bias and heterologous protein expression" TRENDS in Biotechnology, Jul. 2004, 22(7):346-353.
Haft, et al. "Protein Families and Multiple CRISPR/Cas Subtypes Exist in Prokaryotic Genomes" PLoS Computational Biology, 2005, 1(6):0474-483.
Haft, et al. "A Guild of 45 CRISPR-Associated (Cas) Protein Families and Multiple CRISPR/Cas Subtypes Exist in Prokaryotic Genomes" PLoS Computational Biology, 2005, 1(6):0474-0483.
Hale, et al. "Essential Features and Rational Design of CRISPR RNAs that Function With The Cas RAMP Module Complex to Cleave RNAs" Molecular Cell, 2012, 45(3):292-302.
Hale, et al. "RNA-Guided RNA Cleavage by a CRISPR RNA-Cas Protein Complex" Cell, 2009, 139:945-956.
Hale, et al. "Prokaryotic siliencing (psi) RNAs in Pyrococcus furiosus", RNA, 2008, 14:2572-2579.

Handel, et al. "Versatile and Efficient Genome Editing in Human Cells by Combining Zinc-Finger Nucleases With Adeno-Associated Viral-Vectors" Human Gene Therapy, Mar. 2012, 23:321-329.
Hibbitt, et al. "RNAi-mediated knockdown of HMG CoA reductase enhances gene expression from physiologically regulated low-density lipoprotein receptor therapeutic vectors in vivo" Gene Therapy, 2012, 19:463-467.
Rand, et al. "Argonaute2 Cleaves the Anti-Guide Strand of siRNA during RISC Activation" Cell, 2005, 123:621-629.
Raymond, et al. "High-Efficiency FLP and φC31 Site-Specific Recombination in Mammalian Cells" PLoS ONE, 2007, 2(1):e162. Doi. 10.1371/journal.pone.0000162.
Rebar, et al. "Induction of angiogenesis in a mouse model using engineered transcription factors" Nature Medicine, Dec. 2002, 8(12):1427-1432.
Reiss, et al. "RecA protein stimulates homologous recombination in plants" Proc. Natl. Acad. Sci. USA, 1996, 93:3094-3098.
Sanders, et al. "Use of a macromolecular crowding agent to dissect interactions and define functions in transcriptional activation by a DNA-tracking protein: Bacteriophage T4 gene 45 protein and late transcription" PNAS, 1994, 9:7703-7707.
Sapranauskas, et al. "The *Streptococcus thermophilus* CRISPR-Cas system provides immunity in *Escherichia coli*" Nucleic Acids Research, 2011, 39(21): 9275-9282.
Sauer, "Functional Expression of the cre-lox Site-Specific Recombination System in the Yeast *Saccharomyces cerevisiae*" Mol. Cell. Biol., 1987, 7(6):2087-2096.
Sauer, et al. "Site-specific DNA recombination in mammalian cells by the Cre recombinase of bacteriophage P1" Proc. Natl. Acad. Sci. U.S.A., 1988, 85:5166-5170.
Schiffer, et al. "Predictors of Hepatitis B Cure Using Gene Therapy to Deliver DNA Cleavage Enzymes: A Mathematical Modeling Approach" PLOS Computational Biology,, 2013, 9(7):e1003131. www.ploscompbiol.org.
Scholze, et al. "TAL effector-DNA specificity" Virulence, 2010, 1(5):428-432, DOI:10.416/viru.1.5.12863.
Schunder, et al. "First indication for a functional CRISPR/Cas system in Francisella tularensis" International Journal of Medical Microbiology, 2013, 303:1438-4221.
Schramm et al. "Recruitment of RNA polymerase III to its target promoters" Genes & Development, 2002, 16:2593-2620.
Seung Woo Cho, et al. "Supplementary Information: Targeted genome engineering in human cells with RNA-guided endonuclease" Nature Biotechnology, Mar. 2013, 31(3):1-10.
Seung Woo Cho, et al. "Analysis off-target effects of CRISPR/Cas-derived RNA-guided endonucleases and nickases" Genome Research, Nov. 2014, 24:132-141.
Shen, et al. "Efficient genome modification by CRISPR-Cas9 mickase with minimal off-target effects" 2014, Nature Methods, 11(4):399-404.
Shen, et al. "Generation of gene-modified mice via Cas9/RNA-mediated gene targeting" Cell Research, 2013, 23:720-723.
Sims, et al., "High-throughput RNA interference screening using pooled shRNA libraries and next generation sequencing", Genome Biology 12(10):R104, Oct. 2011.
Sontheimer, "Project 7: Establishing RNA-Directed DNA Targeting in Eukaryotic Cells" Physical Sciences-Onc., Nov. 16, 2011-Dec. 31, 2012, htt://groups.molbiosci.northwestern.edu/sontheimer/Sontheimer_cv.php) Molecular Biosciences.
Sosa, et A. "Animal transgenesis: an overiew" Brain Struct Funct, 2010, 214:91-109.
Stolfi, et al, "Tissue-specific genome editing in Ciona embryos by CRISPR/Cas9," Development, 2014, 141:4115-4120 doi:10.1242/dev.114488.
Svviech et al., "In vivo interrogation of gene function in the mammalian brain using CRISPR-Cas9," Nature Biotechnology, 2015, doi:10.1038/nbt.3055.
Terns, et al. "Crispr-based adaptive immune systems" Current Opinion in Microbiology, 2011, 14:321-327.
Tolia, et al. "Slicer and the Argonautes" Nature Chemical Biology, 2007, 3(1):36-43.
Trevino, et al. "Genome Editing Using Cas9 Nickases" Methods in Enxymology, 2014, 546:161-174.

(56) References Cited

OTHER PUBLICATIONS

Urnov, et al. "Highly efficient endogenous human gene correction using designed zinc-finger nucleases" Nature, 2005, 435:646-651.
Vestergaard, et al. "CRISPR adaptive immune systems of Archaea" RNA Biology, 2014, 11(2):156-167.
Wang, et al. One-Step Generation of Mice Carrying Mutations in Multiple Genes by CRISPR/Cas-Mediated Genome Engineering, Cell, 2013, 153:910-918.
Wiedenheft, et al. "RNA-guided genetic silencing systems in bacteria and archaea" Nature, 2012, 482:331-338.
Wu, et al. "Genome-wide binding of the CRISPR endonuclease Cas9 in mammalian cells" Nature Biotechnology, 2014, doi:10.1038/nbt.2889.
Xiao, et al. "Chromosomal deletions and inversions mediated by TALENs and CRIPPR/Cas in zebrafish" Nucleic Acids Research, 2013, 41(14):E141. doi:10.1093/nar/gkt464.
Xiao, et al. Production of High-Titer Recombinant Adeno-Associated Virus Vectors in the Absence of Helper Adenovirus, 72(3) Journal of Virology 2224-2232 (1998).
Zetsche et al. "A split-Cas9 architecture for inducible genome editing and transcription modulation," Nature biotechnology, 2015, 33(2): 139-142.
Zetsche, et al. "CPF1 is a Single RNA-Guided Endonuclease of a Class 2 CRISPR-Cas System" Cell, 2015, 163:759-771.
Zhang, X. D., et al., "cSSMD: assessing collective activity for addressing off-target effects in genome-scale RNA interference screens", Bioinformatics (Oxford), 27(20);2775-2781, Oct. 2011.
Zhang, et al. "Efficient construction of sequence-specific TAL effectors for modulating mammalian transcription" nature biotechnology, 2011, 29(2):149-154.
Zhu, et al. "Crystal structure of Cmr2 suggests a nucleotide cyclase-related enzyme in type III CRISPR-Cas sytems" FEBS Letters, 2012, 939-945. Doi:10.1016/j.febslet2012.02.036.
Hou, et al., "Efficient genome engineering in human pluripotent stem cells using Cas9 from Neisseria meningitides," PNAS, 2013, 110(39):15644-15649.
Horvath et al. "RNA-guidded genome editing a la carte" Cell Research, 2013, 23:733-734, doi:10.1038/cr.2013.39.
Hsu, et al. "Development and Applications of CRISPR-Cas9 for Genome Engineering" Cell, Jun. 2014, 157: 1262-1278.
Hwang Woong, et al. "Efficient genome editing in zebrafish using a CRISPR-Cas System" Nature Biotechnology, Mar. 2013, 31(3):227-229.
Hwang Woong, et al. "Efficient In Vivo Genome Editing Usng RNA-Guided Nucleases" Nat. Biotechnol., 2013, 31(3):227.229. doi. 1.1038/mbt.2501.
Janssen, et al., "Mouse Models of K-ras-Initiated Carcinogenesis" Biochimicia et Biophysica Acta, 2005, 1756:145-154.
Jiang, et al. "RNA-guided editing of bacterial genomes using CRISPR-Cas systems" Nature Biotechnology, 2013, 31(3):233-239.
Jinek, et al, "A Programmable Dual-RNA-Guided DNA Endonuclease in Adaptive Bacterial Immunity" Science, 2012, 337:816-821.
Kanasty, et al. "Delivery materials for siRNA therapeutics" Nature Materials, 2013, 12:967-977.
Karvelis, et al. "crRNA and tracrRNA guide Cas9-mediated DNA interference in *Streptococcus thermophiles*" RNA Biology, 2013, 10(5):841-851.
Karvelis, et al. "Supplemental Material to: crRNA and tracrRNA guide Cas9-mediated DNA interference in *Streptococcus thermophiles*" Landes Bioscience, 2013, 10(5), http://dx.doi.org/10.4161/rna.24203.
Kim, et al. "Crystal structure of Cas1 from Archaeoglobus fulgidus and characterization of its nucleolytic activity" Biochemical and Biophysical Research Communications, 2013, 441:720-725.
Konermann, et al, "Genome-scale transcriptional activation by an engineered CRISPR-Cas9 complex" Nature, 2015, 517:583-588.
Koornneef, et al. "Apoliprotein B Knockdown by AAV-Delivered shRNA Lowers Plasma Cholesterol in Mice" Molecular Therapy, Apr. 2011, 19( 4)731-740.

Lambowitz, et al. "Group II Introns: Mobile Ribozymes that Invade DNA" Cold Spring Harb Perspect Biol., 2011, 3: a003616.
Larson, et al. "CRISPR interference (CRISPRI) for sequence-specific control of gene expression" Nature Protocols, 2013, 8(11):2180-2196.
Lewis, et al., "The c-myc and PyMT oncogenes induce different tumor types in a somatic mouse model for pancreatic cancer" Genes & Development, 2003, 17:3127-3138.
Li, et al. "In vivo genome editing restores hemostasis in a mouse model of hemophilia" Nature, 2011, 475 (7355):217-221. doi: 10.1038/nature10177.
Li, et al. "Multiplex and homologous recombination-mediated genome editing in *Arabidopsis* and *Nicotaina benthamiana* using guide RNA and Cas9" Nature Biotechnology, 2013, 31(9):688-691.
Lombardo, et al., "Gene editing in human stem cells using zinc finger nucleases and integrase-defective lentiviral vector delivery" Nature Biotechnology, 2007, 25(11):1298-1306.
Ma, et al. "A Guide RNA Sequence Design Platform for the CRISPR/Cas9 System for Model Organism Genomes", BioMed Research International, 2014, 2013:270805-4. http://dx.doi.org/10.1155/2014/270805.
Maeder, et al. "CRISPR RNA-guided activation of endogenous human genes" Nature Methods, 2013, 10(10):977-979. doi.10.1038/nmeth.2556.
Makarova, et al, "Evolution and classification of the CRISPR-CAS Systems" Nature Reviews Microbiology, 2011, 9(6):467-477.
Makarova et al. "Unification of Cas protein families and a simple scenario for the origin and evolution of CRISPR-Cas systms" Biology Direct, 2011, 6:38. http:///www.biology-direct.com/content/6/1/38.
Makarova, et al. "An updated evolutionary classification of CRISPR-Cas systems" Nature Reviews-Microbiology, 2015, 13:722-736.
Mali, et al. "CAS9 transcriptional activators for target specificity screening and paired nickases for cooperative genome engineering" nature biotechnology, 2013, 31(9):833-840.
Mali, et al. "Supplementary Information: Use of adjacent sgRNA:Cas9 complexes for transcriptional activation and genome engineering" Nature Biotechnoly, doi:10.1037/nbt.2675, 2013.
Malina, et al. "Repurposing CRISPR/Cas9 for in situ functional assays" Genes & Development, 2013, 27:2602-2614.
Marraffini, et al. "Self vs. non-self discrimination during CRISPR RNA-directed immunity" Nature, 2010, 463(7280):568-571.
Mastroianni, et al. "Group II Intron-Based Gene Targeting Reactions in Eukaryotes" Plos One, 2008, 3(9):e3121. Doi:10.1371/journal.pone.0003121.
Meshorer, et al. "Chromatin in pluripotent embryonic stem cells and differentiation" Nature Reviews Molecular Cell Biology, 2006, 7:540-546.
Miller, et al. "A Tale nuclease architecture for efficient genome editing" Nature Biotechnology, 2011, 29(2):143-150.
Minton, "How can biochemical reactions within cells differ from those in test tubes?" Journal of Cell Science, 2006, 119:2863-2869.
Mojica, et al. "Short motif sequences determine the targets of the prokaryotic CRISPR defence system", Microbiology, 2009, 155:733-740.
Morgan, et al. "Inducible Expression and Cytogenetic Effects of the EcoRI Restriction Endonuclease in Chinese Hamster Ovary Cells" Molecular and Cellular Biology, 1988, 8(10):4204-4211.
Mukhopadyay, "On the Same Wavelength," ASBMBTODAY, Aug. 2014, http://www.asbmb.org/asbmbtoday/201408/Features/Doudna/.
Nakamura, et al. "Codon usage tabulated from international DNA sequence databases: status for the year 2000" Nucleic Acids Research, 2000, 28(1): 292.
Nomura, et al., "Low-density lipoprotein receptor gene therapy using helper-dependent adenovirus produces long-term protection against atherosclerosis in a mouse model of familial hypercholesterolemia" Gene Therapy, 2004, 11:1540-1548.
Nishimasu et al. "Crystal Structure of *Staphylococcus aureus* Cas9," Cell 162, 1113-1126, Aug. 27, 2015.
Nishimasu, et al. Crystal Structure of Cas9 in Complex with Guide RNA and Target DNA, Cell, 2014, 156:935-949.

(56) References Cited

OTHER PUBLICATIONS

Oost, "New Tool for Genome Surgery" Science, Feb. 15, 2013, 399:768-770.
Panyam, et al. "Biodegradable nanoparticles for drug and gene delivery to cells and tissue" Advanced Drug Delivery Reviews, 2003, 55:329-347.
Patterson, et al. "Codon optimization of bacterial luciferase (lux) for expression in mammalian cells" J. Ind. Microbio. Biotechnology, 2005, 32:115-123.
Pinera, et al. "RNA-guided gene activation by CRISPR-Cas9-based transcription factors" Nature Methods, 2013, 10(10):973-978.
Platt, et al. "CRISPR-Cas9 Knockin Mice for Genome Editing and Cancer Modeling" Cell, 2014, 159(2):440-455.
Porteus, et al. "Gene targeting using zinc finger nucleases" Nature Biotechnology, 2005, 23(8):967-973.
Pougach, et al. "Transcription, Processing and Function of CRISPR Cassettes in *Escherichia coli*" Mol. Microbiol, 2010, 77(6):1367-1379.
Ran, et al, "In vivo genome editing using *Staphylococcus aureus* Cas9," Nature, 2015, doi:10.1038/nature14299.
Ran et al. "Double Nicking by RNA-Guided CRISPR Cas9 for Enhanced Genome Editing Specificity," Cell 154, 1-10, Sep. 12, 2013.
Ran, et al. "Genome engineering using the CRISPR-Cas9 system" Nature Protocols, 2013, 8(11):2281-2308.
International Search Report dated Feb. 17, 2015; which issued during prosecution of International Application No. PCT/US2014/062558.
Heintze, et al. "A CRISPR CASe for high-throughpu silencing", Frontiers in Genetics, Oct. 2013, 4(193): DOI:10.3389/gfene.2013.00193.
Mali, et al. "RNA-Guided Human Genome Engineering via Cas9", Science, 2013, 339:823-826.
Mali, et al., "Supplementary Materials for RNA-Guided Human Genome Engineering via Cas9", SCIENCE, 2013, DOI:10.1126/Science.1232033.
Hsu, et al. "DNA targeting specificity of RNA-guided Cas9 Nucleases" Nature Biotechnology, 2013, doi:10.1038/nbt.2647.
Hsu, et al. "Supplementary Information-DNA targeting specificity of RNA-guided Cas9 Nuclease" Nature Biotechnology, 2013, 31(9):827-382.
Gilbert, et al. "CRISPR-Mediated Modular RNA-Guided Regulation of Transcription in Eukaryotes", Cell, Jul. 2013, 154:442-S5.
Jao, et al. "Efficient multiplex biallelic zebrafish genome editing using a CRISPR nuclease system" Proceeding of the National Academy of Sciences, 2013, www.pnas.org/cgi/doi/10.1073/pnas.1308335110.
Zhang, et al., "Optimized CRISPR Design"; XP055167487, Oct. 23, 2013, URL:http://crispr.mit.edu/about[retrieved on Feb. 9, 2015].
"Fixes, extra genomes, and improvements to the CRISPR Design Tool" Google Groups, XP055167583, Oct. 21, 2013; URL:https://groups.google.com/forurm/#ltopic/crispr/g9Q8U1tNSis [retrieved on Feb. 5, 2015]. 1.
Holmes, "CRISPR Genome Engineering Resources" XP055167586, Oct. 2, 2013, https://groups.google/forum/#ltop1c/crispr/5BpJj_Y3ylG [retreieved on Feb. 5, 2015].
"Crispr genome engineering" XP055167591, Oct. 5, 2013, https://web.archive.org/web/2013100500 [retrieved on Feb. 5, 2015.
Holmes, "Understanding Scores" XP055167918, Oct. 23, 2013, https://groups.google.com/forum/'iprofo_nt50txrP9Yb6e_LXccolb9hNf7gKeMLt6rgaVQ4fOsQ/crispr/fkhX7Fu3r-l/rziHxKT76pYJ [retrieved on Feb. 6, 2015].
Lou et al. "Highly parallel identification of essential genes in cancer cells", Proceedings of the National Academy of Sciences 2008, 105(51):20380-20385.
Fu, et al. "High-frequency off-target mutagenesis induced by CRISPR-Cas nucleases in human cells", Nature Biotechnology, 2013, 31(9):822-826.

Cong, et al. "Multiplex Genorne Engineering Using CRISPR/Cas Systems" Science, 2013, 339:819-823. DOI:10.1126/science.1231143.
Cong, et al. "Supplementary-Multiplex Genome Engineering Using Crispr/Cas Systems" Science, 2013, DOI:10.1126/sciences.1231143.
Jinek et al. "RNA-programmed genome editing in human cells" E-LIFE, 2013, 2:E00471. DOI: 10.7554/eLife.00471.
Jinek et al. "Figures and figure Supplements-RNA-programmed genome editing in human cells", E-Life, 2013, 2:e00471. DOI:7554/e.Life.00471.
Qi, et al. "Repurposing CRISPR as an RNA-Guided Platform for Sequence-Specific Control of Gene Expression" Cell, 152:1173-S7, Feb. 28, 2013.
Seung Woo Cho, et al. "Targeted geonome engineering in human cells with the Cas9 RNA-guided endonuclease", Nature Biotechnology, 2013, 31(3):230-232, including Supplementary Information 1-11.
Shalem, et al. "Genome-Scale CRISPR-Cas9 Knockout Screening in Human Cells", Science, 343:84-87, Dec. 12, 2013.
Wang, et al. "Genetic Screens in Human Cells Using the CRISPR-Cas9 System", Science, 343:80-84, Dec. 12, 2013.
International Preliminary Report and Written Opinion of the International Searching Authority dated May 3, 2016, which issued during prosecution of International Application No. PCT/US2014/062558.
Sapranauskas, et al., "The *Streptococcus thermophilus* CRISPR/Cas System Provides Immunity in *Escherichia coli*," Nucleic Acids Research, vol. 39, No. 21, pp. 9275-9282, Aug. 2011.
Semenova, et al., "Interference by Clustered Regularly Interspaced Short Palindromic Repeat (CRISPR) RNA Is Governed by a Seed Sequence," Proceedings of the National Academy of Sciences, pp. 10098-10103, Jun. 2011.
Shalem, et al., "Genome-Scale CRISPR-Cas9 Knockout Screening in Human Cells," Science, vol. 343, No. 6166, pp. 84-87, 2014.
Terns, et al., "CRISPR-Based Adaptive Immune Systems," Current Opinion in Microbiology, vol. 14, No. 3, pp. 321-327, Jun. 2011.
Tsai, et al., "Dimeric CRISPR RNA-Guided Foki Nucleases for Highly Specific Genome Editing," Nature Biotechnology, vol. 32, No. 6, pp. 569-576, Jun. 2014.
Van Der Oost, "CRISPR-based Adaptive and Heritable Immunity in Prokaryotes," Trends in Biochemical Sciences, vol. 34, No. 8, pp. 401-407, Aug. 2009.
Wang, et al., "Genetic Screens in Human Cells Using the CRISPR/Cas9 System," Science, vol. 343, No. 6166, pp. 80-84, Jan. 2014.
Wang, et al., "Genome-Scale Promoter Engineering by Co-Selection MAGE," Nature Methods, vol. 9, No. 6, pp. 591-593, Jun. 2012.
Wang, et al., "One-Step Generation of Mice Carrying Mutations in Multiple Genes by CRISPR/Cas-Mediated Genome Engineering," Cell, vol. 153, No. 4, pp. 910-918, May 2013.
Wiedenheft B., "RNA-Guided Complex from a Bacterial Immune System Enhances Target Recognition Through Seed Sequence Interactions," Proceedings of the National Academy of Sciences, vol. 108, No. 25, pp. 10092-10097, Jun. 2011.
Wu, et al., "Genome-Wide Binding of the CRISPR Endonuclease Cas9 in Mammalian Cells," Nature Biotechnology, vol. 32, No. 7, pp. 670-676, Jul. 2014.
Zhang, et al., "CRISPR Genome Engineering Resources," Zhang Lab, retrieved on Oct. 2013, 3 pages.
Zhang, et al., "Optimized CRISPR Design," retrieved from www.groups.google.com/forum/#!forum/crispr, on Feb. 5, 2015, 2 pages.
Hsu, "CRISPR Design Tool—Google Groups," retrieved from www.crispr.mit.edu/about, on Feb. 5, 2015, 2 pages.
The Broad Institute Inc., International Preliminary Report on Patentability issued in International Application No. PCT/US2014/062558, 9 pages, dated May 3, 2016.
The Broad Institute Inc., International Search Report and Written Opinion issued in International Application No. PCT/US2014/062558, 16 pages, dated Feb. 17, 2015.
Barrangou, et al., "CRISPR Provides Acquired Resistance Against Viruses in Prokaryotes," Science, vol. 315, No. 5819, pp. 1709-1712, Mar. 23, 2007.

(56) References Cited

OTHER PUBLICATIONS

Bikard, et al., "CRISPR Interference Can Prevent Natural Transformation and Virulence Acquisition during In Vivo Bacterial Infection," Cell Host & Microbe, vol. 12, No. 12, pp. 177-186, Aug. 16, 2012.
Carroll, "A CRISPR Approach to Gene Targeting," Molecular Therapy, vol. 20, No. 9, pp. 1658-1660, Sep. 2002.
Carte, et al., "Cas6 is an Endoribonuclease that Generates Guide Rnas for Invader Defense in Prokaryotes," Genes & Development, vol. 22, pp. 3489-3496, 2008.
Zho, et al., "Targeted Genome Engineering in Human Cells with the Cas9 RNA-guided Endonuclease," Nature Biotechnology, vol. 31, No. 3, pp. 230-232, Mar. 2013.
Chylinski, et al., "The TracrRNA and Cas9 Families of Type II CRISPR-Cas Immunity Systems," RNA Biology, vol. 10, No. 5, pp. 726-737, May 2013.
Cong, et al., "Multiplex Genome Engineering Using CRISPR/Cas Systems," Science, vol. 339, No. 6121, pp. 819-823, Feb. 2013.
Cradick, et al., "CRISPR/Cas9 Systems Targeting B-Globin and CCR5 Genes Have Substantial Off-Target Activity," Nucleic Acids Research, vol. 41, No. 20, 9584-9592, Aug. 2013.
Deltcheva, et al., "CRISPR RNA Maturation by Trans-Encoded Small RNA and Host Factor Rnase III", Nature, vol. 471, No. 7340, Mar. 31, 2011, 602-607.
Doench, et al., "Rational Design of Highly Active Sgmas for CRISPR-Cas9-Mediated Gene Inactivation", Nature Biotechnology, vol. 32, No. 12, Sep. 3, 2014, 1262-1267.
Edgar, et al. "The Escherichia coli CRISPR System Protects from ? Lysogenization, Lysogens, and Prophage Induction," Journal of Bacteriology, vol. 192, No. 23, pp. 6291-6294, Dec. 2010.
Fischer, et al., "An Archaeal Immune System Can Detect Multiple Protospacer Adjacent Motifs (PAMs) to Target Invader DNA," The Journal of Biological Chemistry, vol. 287, No. 40, pp. 33351-33365, Sep. 2012.
Fu et al. "High Frequency Off-Target Mutagenesis Induced by CRISPR-Cas Nucleases in Human Cells," Nature Biotechnology, vol. 31, No. 9, pp. 822-826, Sep. 2013.
Garneau, et al., "The CRISPR/Cas Bacterial Immune System Cleaves Bacteriophage and Plasmid DNA," Nature, vol. 468, pp. 67-71, Nov. 2010.
Gasiunas, et al., "Cas9-CrRna Ribonucleoprotein Complex Mediates Specific DNA Cleavage for Adaptive Immunity in Bacteria", Proceedings of the National Academy of Sciences, vol. 109, No. 39, Sep. 25, 2012, E2579-E2586.
Gilbert, et al., "CRISPR-Mediated Modular RNA-Guided Regulation of Transcription in Eukaryotes," Cell, vol. 154, No. 2, pp. 442-451, Jul. 2013.
Gudbergsdottir, et al., "Dynamic Properties of the Sulfolobus CRISPR/Cas and CRISPR/Cmr Systems when Challenged with Vector-Borne Viral and Plasmid Genes and Protospacers," Molecular Microbiology, vol. 79, No. 1, pp. 35-49, 2011.
Hatoum-Aslan, et al., "Mature Clustered, Regularly Interspaced, Short Palindromic Repeats RNA (Crrna) Length is Measured by a Ruler Mechanism Anchored at the Precursor Processing Site," Proceedings of the National Academy of Sciences, vol. 108, No. 52, pp. 21218-21222, Dec. 2011.
Haurwitz, et al., "Sequence- and Structure-Specific RNA Processing by a CRISPR Endonuclease," Science, vol. 329, No. 5997, pp. 1355-1358, Sep. 2010.
Heintze, et al., "A CRISPR CASe for High-throughput Silencing," Frontiers in Genetics, vol. 4, Article 193, 6 pages, Oct. 2013.
Holmes, "Announcement, Fixes, Extra Genomes and Improvements to the CRISPR Design tool—Google Groups," retrieved from www.group.google.com/forum/#!topic/crispr/g9Q8UItNSis, retrieved on Feb. 5, 2015, 2 pages.
Holmes, "Announcement, Understanding Scores—Google Groups," retrieved from www.web.archive.org/web/2013005002950, on Feb. 5, 2015, 2 pages.

Horii, et al., "Generation of an ICF Syndrome Model by Efficient Genome Editing of Human Induced Pluripotent Stem Cells Using the CRISPR System," International Journal of Molecular Sciences, vol. 14, pp. 19774-19781, 2013.
Horvath, et al., "CRISPR/Cas, the Immune System of Bacteria and Archaea," Science, vol. 327, pp. 167-170, Jan. 2010.
Hsu, et al., "Development and Applications of CRISPR-Cas9 for Genome Engineering", Cell, vol. 157, No. 6, Jun. 5, 2014, 1262-1278.
Hsu, et al., "DNA Targeting Specificity of RNA-Guided Cas9 Nucleases", Nat. Biotechnol. vol. 31, No. 9, Sep. 3, 2013, 827-832.
Hwang, et al., "Efficient genome editing in zebrafish using a CRISPR-Cas system," Nature Biotechnology, vol. 31, No. 3, pp. 227-229, Mar. 2013.
Jansen, et al., "Identification of a Novel Family of Sequence Repeats among Prokaryotes," OMICS: A Journal of Integrative Biology, vol. 6, No. 1, pp. 23-33, Feb. 2002.
Jansen, et al., "Identification of Genes that are Associated with DNA Repeats in Prokaryotes," Molecular Microbiology, vol. 46, No. 6, pp. 1565-1575, Apr. 2002.
Jao, et al., "Efficient Multiplex Biallelic Zebrafish Genome Editing Using a CRISPR Nuclease System," Proceedings of the National Academy of Sciences, vol. 110, No. 34, pp. 13904-13909, Aug. 2013.
Jiang, et al., "RNA-guided editing of bacterial genomes using CRISPR-Cas systems", Nature Biotechnology, vol. 31, Issue 3, Mar. 2013, 233-239.
Jinek, et al., "A Programmable Dual-RNA-Guided DNA Endonuclease in Adaptive Bacterial Immunity", Science, vol. 337, No. 6096,, Aug. 17, 2012, 816-821.
Jinek, et al., "RNA-programmed Genome Editing in Human Cells," Elife, vol. 2, e00471, pp. 1-9, Jan. 2013.
Konermann, et al., "Optical Control of Mammalian Endogenous Transcription and Epigenetic States", Nature, vol. 500, No. 7463, Aug. 22, 2013, 472-476.
Luo, et al., "Highly Parallel Identification of Essential Genes in Cancer Cells," Proceedings of the National Academy of Sciences, vol. 105, No. 51, pp. 20380-20385, 2008.
Maeder, et al., "CRISPR RNA-Guided Activation of Endogenous Human Genes," Nature Methods, vol. 10, No. 10, pp. 977-979, Oct. 2013.
Makarova, et al., "Unification of Cas Protein Families and a Simple Scenario for the Origin and Evolution of Crisprcas Systems," Biology Direct, vol. 6, No. 38, 27 pages, 2011.
Mali, et al., "RNA-Guided Human Genome Engineering via Cas9", Science, vol. 339, No. 6121, Feb. 15, 2013, 823-826.
Mali, et al., "CAS9 Transcriptional Activators for Target Specificity Screening and Paired Nickases for Cooperative Genome Engineering," Nature Biotechnology, vol. 31, No. 9, pp. 833-838, Sep. 2013.
Marraffini, et al., "Self Vs. Non-Self Discrimination During CRISPR RNA-Directed Immunity," Nature, vol. 463, No. 7280, pp. 568-571, Jan. 2010.
Mojica, et al., "Intervening Sequences of Regularly Spaced Prokaryotic Repeats Derive from Foreign Genetic Elements," Journal of Molecular Evolution, vol. 60, No. 2, pp. 174-182, Mar. 2005.
Mojica, et al., "MicroCorrespondence: Biological significance of a family of regularly spaced repeats in the genomes of Archaea, Bacteria and mitochondria," Molecular Microbiology, vol. 36, pp. 244-246, 2000.
Nishimasu, et al., "Crystal Structure of Cas9 in Complex with Guide RNA and Target DNA", Cell, vol. 156, No. 5, Feb. 27, 2014, pp. 935-949.
Perez-Pinera, et al., "RNA-Guided Gene Activation by CRISPR-Cas9-Based Transcription Factors," Nature Methods, vol. 10, No. 10, pp. 973-976, Oct. 2013.
Qi, et al., "Repurposing CRISPR as an RNA-Guided Platform for Sequence-Specific Control of Gene Expression," Cell, vol. 152, No. 5, pp. 1173-1183, Feb. 2013.
Ran, et al., "Double Nicking by RNA-Guided CRISPR Cas9 for Enhanced Genome Editing Specificity," Cell, vol. 154, No. 6, pp. 1380-1389, Sep. 2013.

(56) References Cited

OTHER PUBLICATIONS

Ran, et al., "Genome Engineering using the CRISPR-Cas9 System", Nature Protocols, vol. 8, No. 11, Nov. 2013, pp. 2281-2308.

* cited by examiner

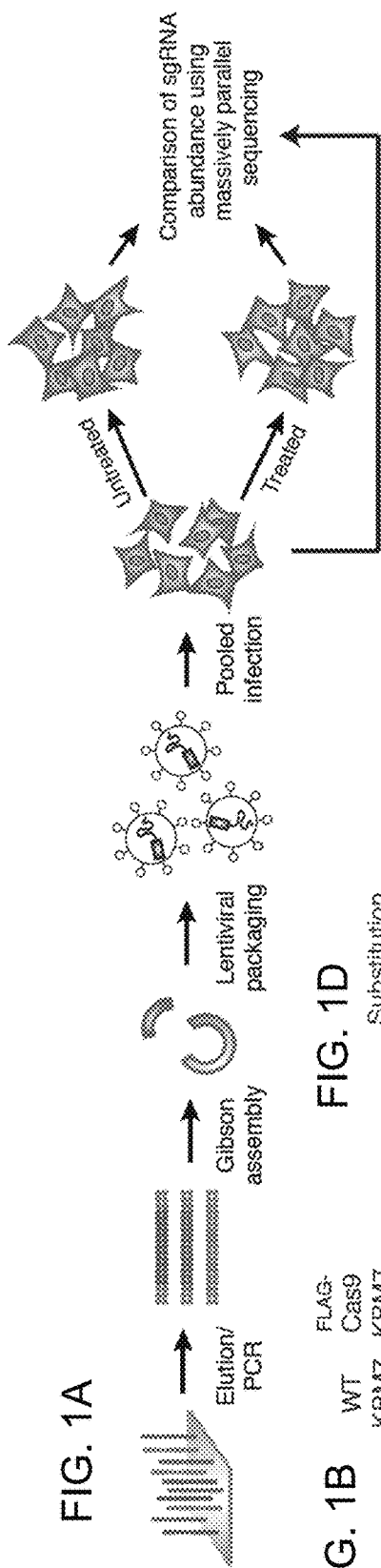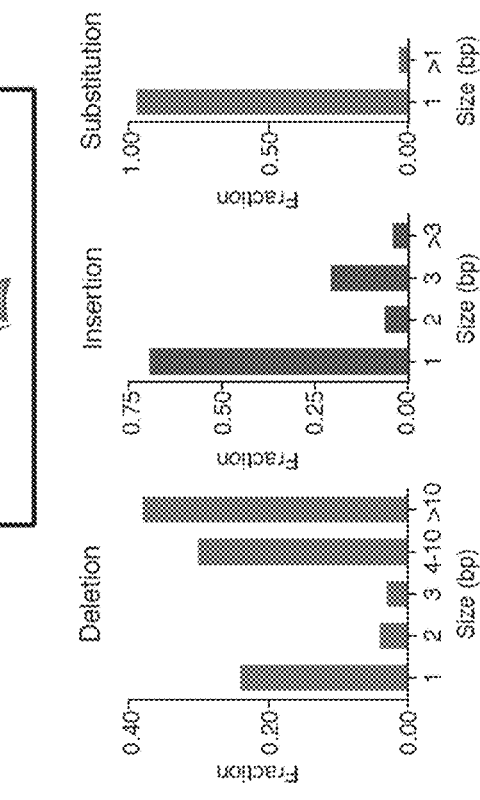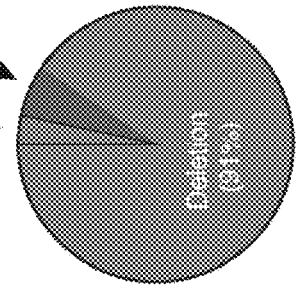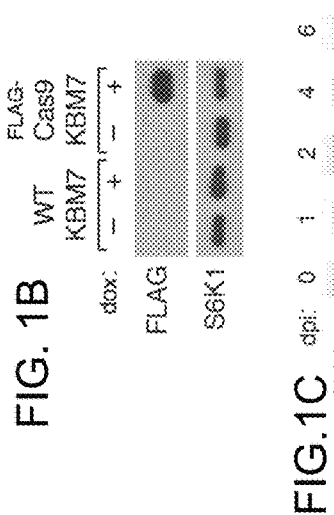
FIG. 1A
FIG. 1B
FIG. 1C
FIG. 1D

FIG. 1E
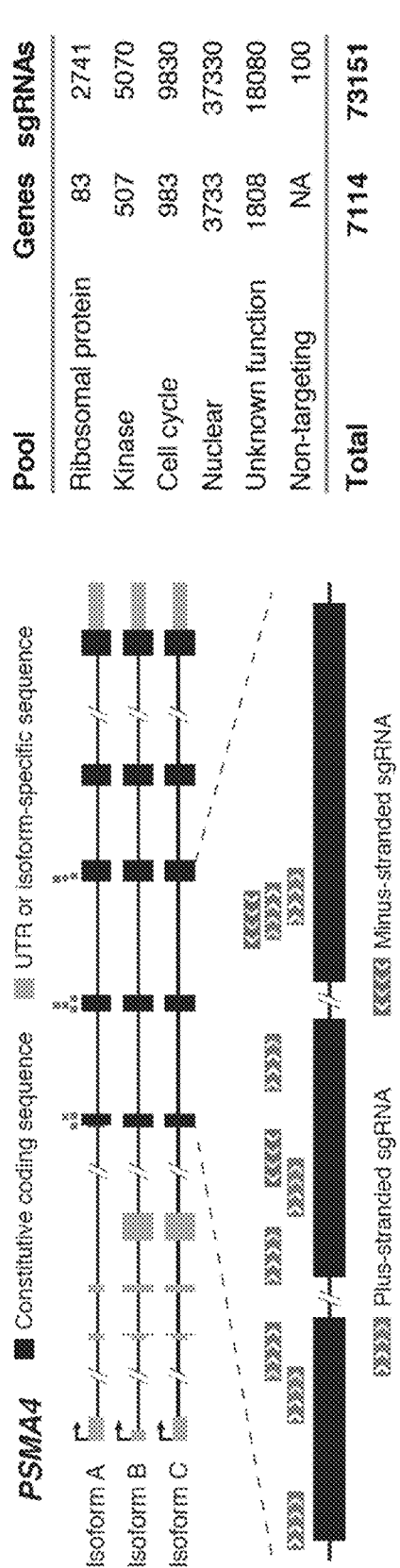
FIG. 1F
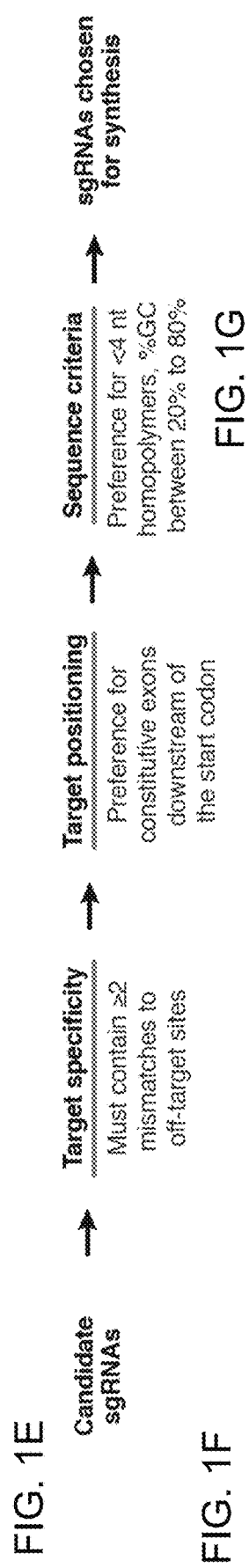
FIG. 1G
| Pool | Genes | sgRNAs |
|---|---|---|
| Ribosomal protein | 83 | 2741 |
| Kinase | 507 | 5070 |
| Cell cycle | 983 | 9830 |
| Nuclear | 3733 | 37330 |
| Unknown function | 1808 | 18080 |
| Non-targeting | NA | 100 |
| Total | 7114 | 73151 |

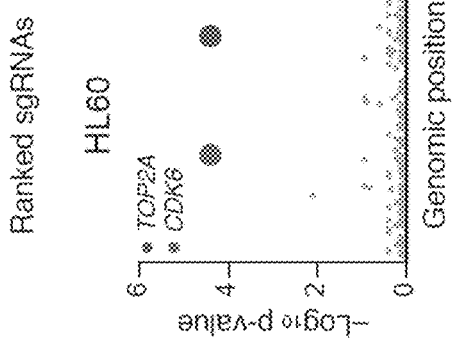
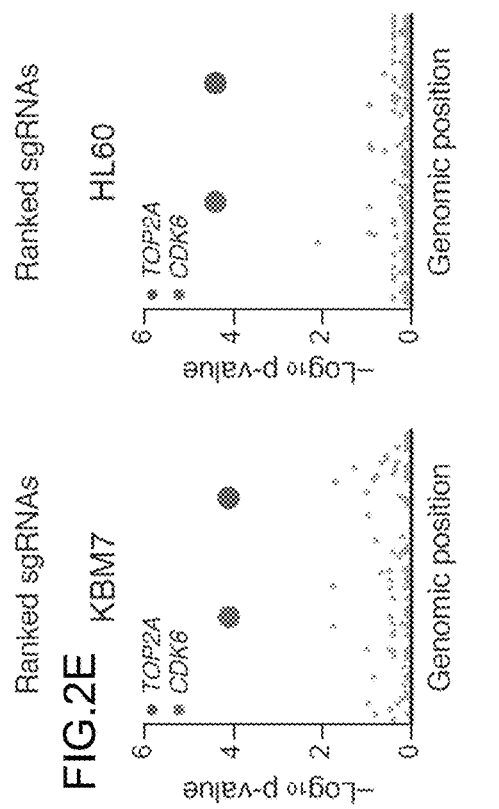
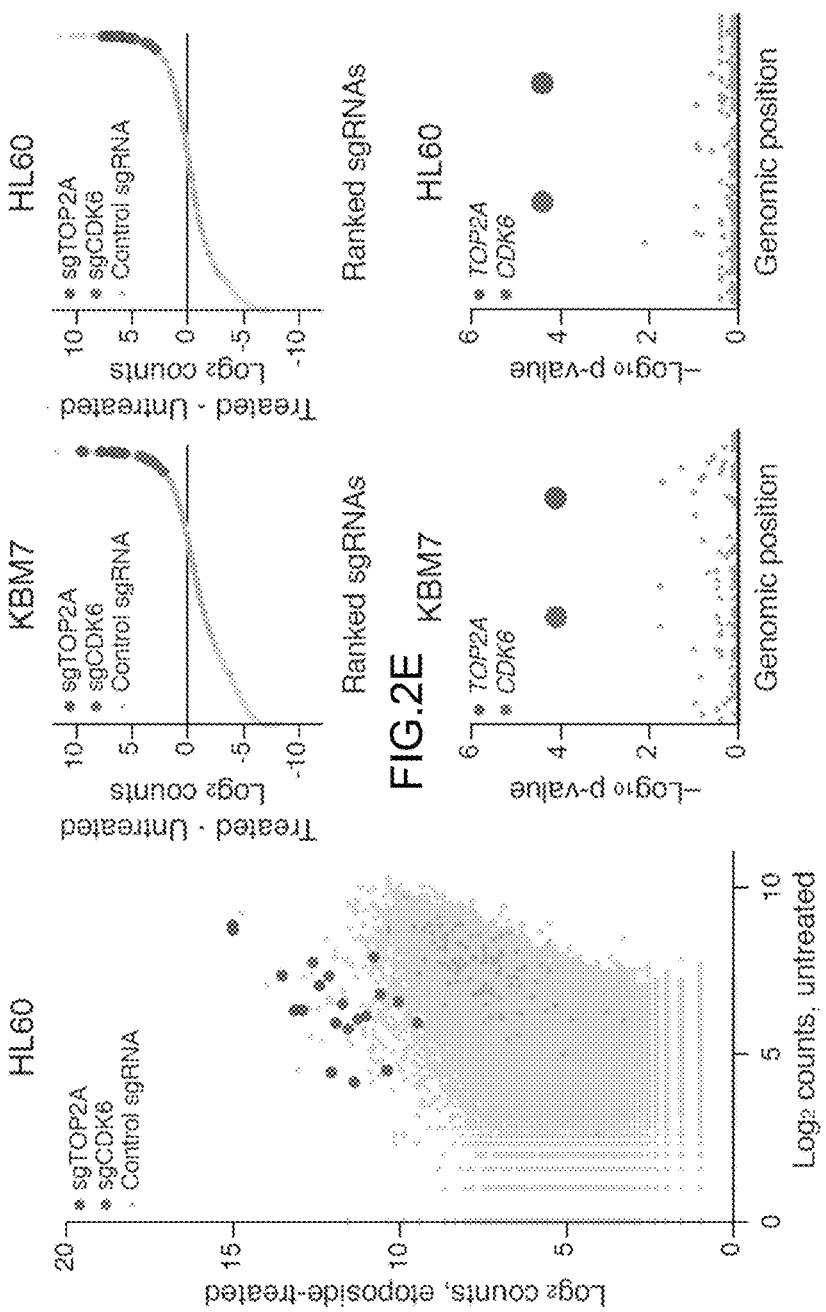
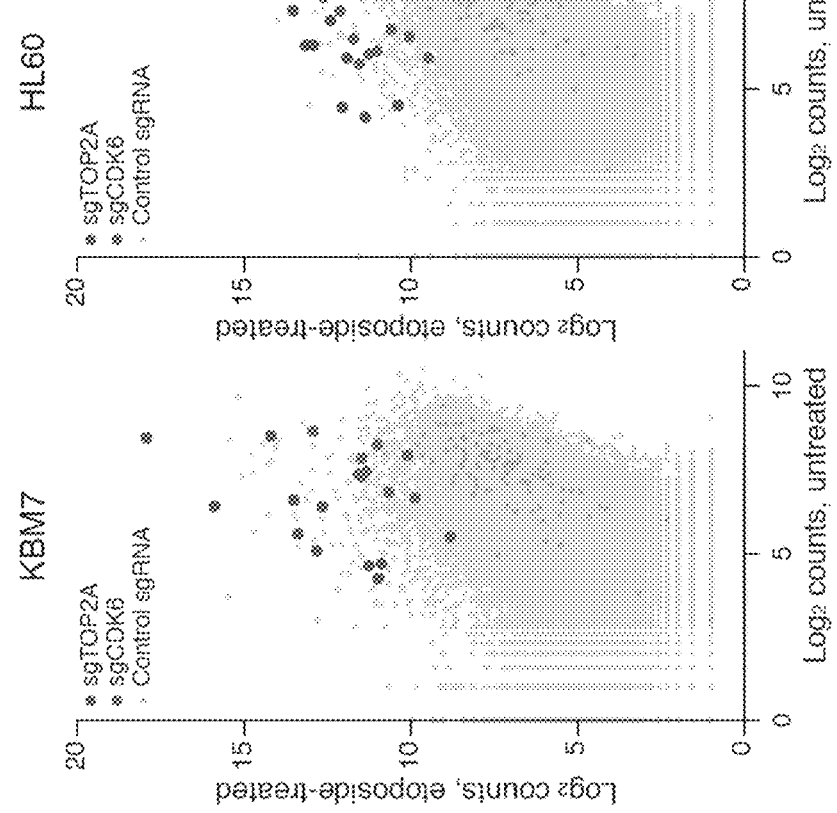

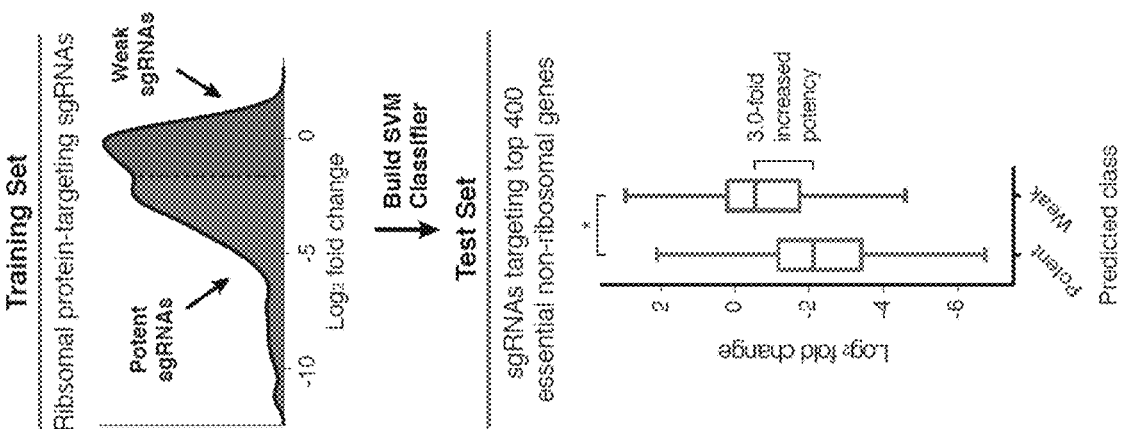
FIG. 3E
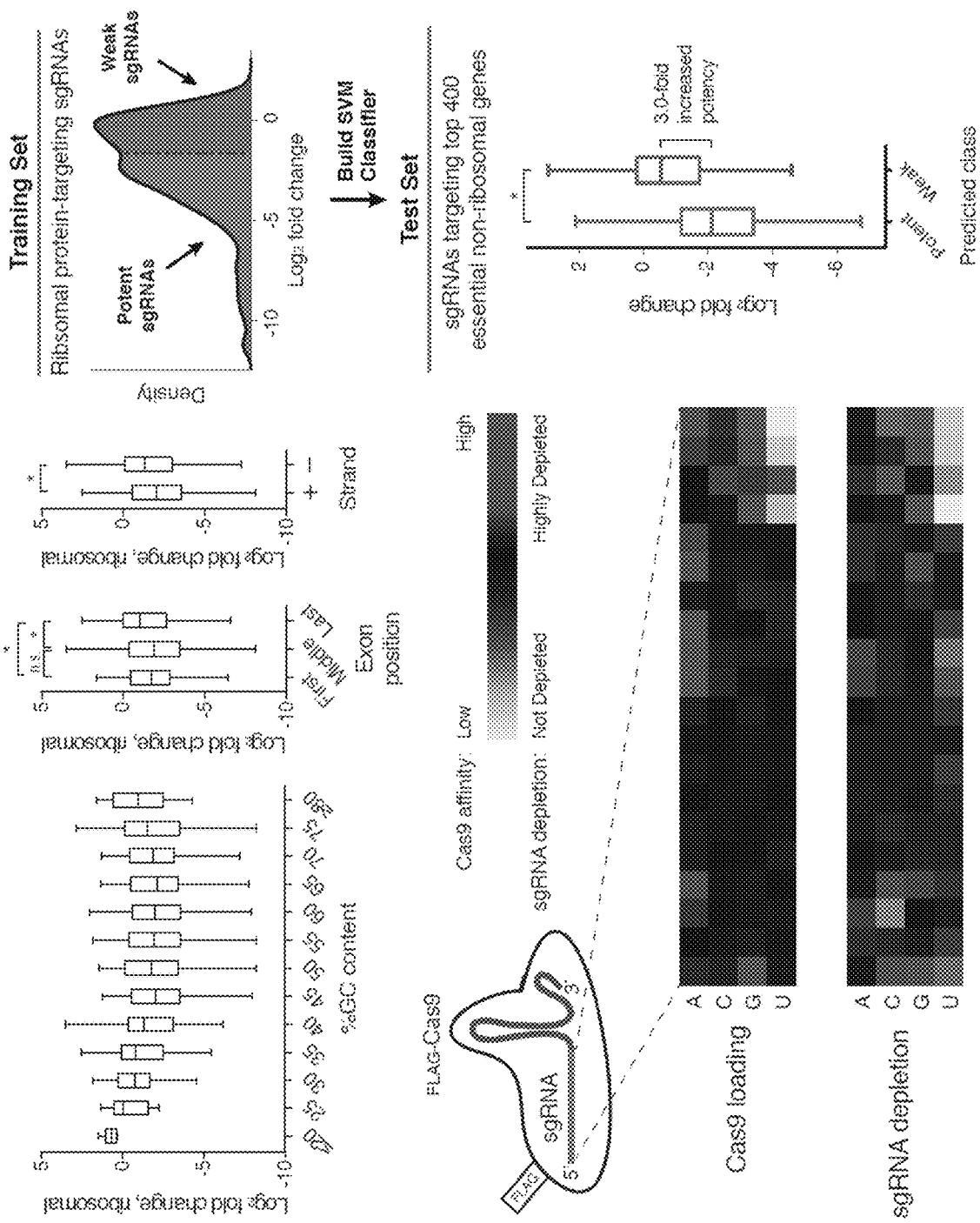
FIG. 3G
FIG. 3F

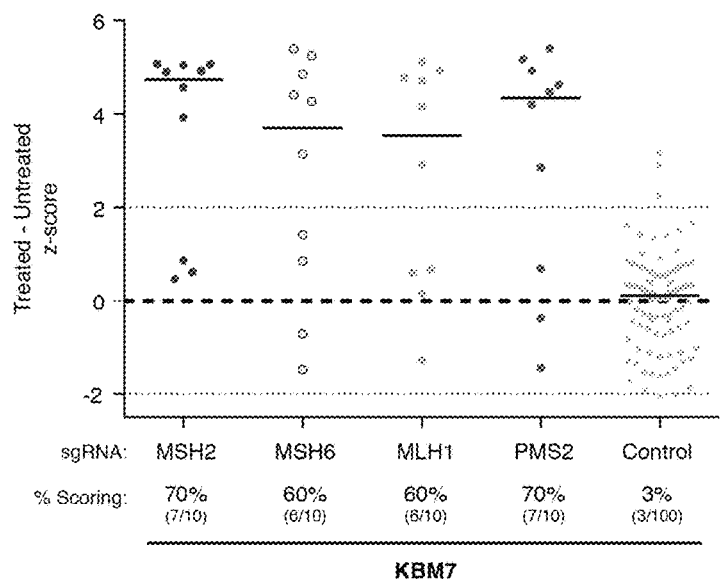
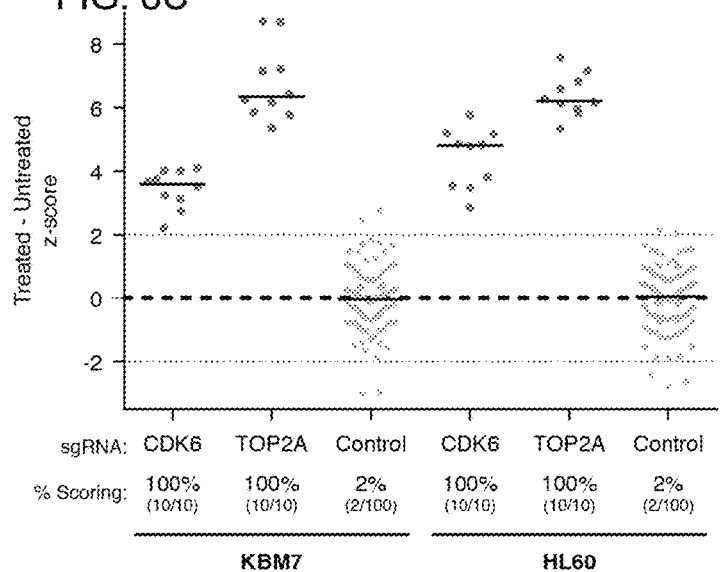

FUNCTIONAL GENOMICS USING CRISPR-CAS SYSTEMS, COMPOSITIONS, METHODS, SCREENS AND APPLICATIONS THEREOF

RELATED APPLICATIONS AND INCORPORATION BY REFERENCE

This application is a continuation-in-part of International patent application Serial No. PCT/US2014/062558 filed Oct. 28, 2014, and published as PCT Publication No. WO2015/065964 on May 7, 2015 and which priority is claimed from U.S. provisional patent applications 61/961,980, 61/963,643 and 62/069,243 each entitled FUNCTIONAL GENOMICS USING CRISPR-CAS SYSTEMS, COMPOSITIONS, METHODS, SCREENS AND APPLICATIONS THEREOF, filed Oct. 28, 2013, Dec. 9, 2013 and Oct. 27, 2014 respectively. Reference is also made to PCT/US2014/041806, filed Jun. 10, 2014, U.S. provisional patent applications 61/836,123, 61/960,777 and 61/995,636, filed on Jun. 17, 2013, Sep. 25, 2013 and Apr. 15, 2014, and PCT/US13/74800, filed Dec. 12, 2013.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

The disclosure in each of the foregoing US provisional and PCT patent applications is particularly incorporated herein by reference and particularly the disclosure of the CDs filed with U.S. provisional patent applications 61/960,777 and 61/995,636 is particularly incorporated herein by reference in their entirety and is also included in this disclosure by way of the Biological Deposit(s) with the ATCC of plasmids/plasmid library(ies) containing nucleic acid molecules encoding selected guide sequences having the information set forth in U.S. provisional patent applications 61/960,777 and 61/995,636, namely, Deposit Nos: PTA-121339, PTA-121340, PTA-121341, PTA-121342, PTA-121343, deposited on Jun. 10, 2014, with the American Type Culture Collection on American Type Culture Collection (ATCC), 10801 University Boulevard, Manassas, Va. 20110 USA, under and pursuant to the terms of the Budapest Treaty. Upon issuance of a patent, all restrictions upon the Deposit(s) will be irrevocably removed, and the Deposit(s) is/are intended to meet the requirements of 37 CFR §§ 1.801-1.809. The Deposit(s) will be maintained in the depository for a period of 30 years, or 5 years after the last request, or for the effective, enforceable life of the patent, whichever is longer, and will be replaced if necessary during that period; and the requirements of 37 CFR §§ 1.801-1.809 are met. The herein term "GeCKO library" can mean the information in the foregoing US provisional and PCT patent applications, or the disclosure of the CDs filed with U.S. provisional patent applications 61/960,777 and 61/995,636, or any one or more of ATCC Deposit Nos: PTA-121339, PTA-121340, PTA-121341, PTA-121342 and PTA-121343.

STATEMENT AS TO FEDERALLY SPONSORED RESEARCH

This invention was made with government support under Grant Nos. CA103866 and HG03067 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Apr. 5, 2021, is named BROD-3080US_ST25.txt is 10,724 bytes in size.

FIELD OF THE INVENTION

The present invention generally relates to compositions, methods, applications and screens used in functional genomics that focus on gene function in a cell and that may use vector systems and other aspects related to Clustered Regularly Interspaced Short Palindromic Repeats (CRISPR)-Cas systems and components thereof.

BACKGROUND OF THE INVENTION

Recent advances in genome sequencing techniques and analysis methods have significantly accelerated the ability to catalog and map genetic factors associated with a diverse range of biological functions and diseases. Functional genomics is a field of molecular biology that may be considered to utilize the vast wealth of data produced by genomic projects (such as genome sequencing projects) to describe gene (and protein) functions and interactions. Contrary to classical genomics, functional genomics focuses on the dynamic aspects such as gene transcription, translation, and protein-protein interactions, as opposed to the static aspects of the genomic information such as DNA sequence or structures, though these static aspects are very important and supplement one's understanding of cellular and molecular mechanisms. Functional genomics attempts to answer questions about the function of DNA at the levels of genes, RNA transcripts, and protein products. A key characteristic of functional genomics studies is a genome-wide approach to these questions, generally involving high-throughput methods rather than a more traditional "gene-by-gene" approach. Given the vast inventory of genes and genetic information it is advantageous to use genetic screens to provide information of what these genes do, what cellular pathways they are involved in and how any alteration in gene expression can result in particular biological process. Functional genomic screens attempt to characterize gene function in the context of living cells and hence are likely to generate biologically significant data. There are three key elements for a functional genomics screen: a good reagent to perturb the gene, a good tissue culture model and a good readout of cell state.

A reagent that has been used for perturbing genes in a number of functional genomics screens is RNA interference (RNAi). One can perform loss-of-function genetic screens and facilitate the identification of components of cellular signaling pathways utilizing RNAi. Gene silencing by RNAi in mammalian cells using small interfering RNAs (siRNAs) and short hairpin RNAs (shRNAs) has become a valuable genetic tool. Development of efficient and robust approaches to perform genome-scale shRNA screens have been described in Luo B et al., "Highly parallel identification of essential genes in cancer cells" Proc Natl Acad Sci USA. 2008 Dec. 23:105(51):20380-5; Paddison P J et al., "A resource for large-scale RNA-interference-based screens in mammals" Nature. 2004 Mar. 25; 428(6981):427-31; Berns K et al., "A large-scale RNAi screen in human cells identifies new components of the p53 pathway" Nature. 2004 Mar. 25; 428(6981):431-7, the contents of all of which are incorporated by reference herein in their entirety.

However, there are aspects of using shRNAs for functional genomic screens that are not advantageous. For example, there may be off-target effects for the shRNAs that limit spatial control. It is also important to note that using RNAi or other current technologies in functional genomics screens as mentioned herein results in a gene knockdown and not a gene knockout. Another minor factor that may be considered is the need for the continued expression of shRNA. Hence, there remains a need for new genome engineering technologies that are affordable, easy to set up, scalable, and amenable to knockout genes for de novo loss of function and afford spatial and temporal control with minimal off-target activity in a eukaryotic genome.

SUMMARY OF THE INVENTION

There exists a pressing need for alternative and robust systems and techniques for sequence targeting in functional genomic screens and other applications thereof. This invention addresses this need and provides related advantages. The CRISPR/Cas or the CRISPR-Cas system (both terms are used interchangeably throughout this application) does not require the generation of customized proteins (as in the case of technologies involving zinc finger proteins, meganucleases or transcription activator like effectors (TALEs)) to target specific sequences but rather a single Cas enzyme can be programmed by a short RNA molecule to recognize a specific DNA target, in other words the Cas enzyme can be recruited to a specific DNA target using said short RNA molecule. This enables parallel targeting of thousands of genomic loci using oligo library synthesis. Adding the CRISPR-Cas system to the repertoire of functional genomics tools and analysis methods may significantly simplify the methodology and accelerate the ability to catalog and map genetic factors associated with a diverse range of biological functions and diseases. The CRISPR-Cas system can be used effectively for gene targeting and knockout without deleterious effects in functional genomic screens and other applications thereof.

In one aspect, the invention provides a genome wide library comprising a plurality of unique CRISPR-Cas system guide sequences that are capable of targeting a plurality of target sequences in genomic loci, wherein said targeting results in a knockout of gene function.

In one aspect, the invention provides a non-transitory computer program product comprising one or more stored sequences of instructions that is accessible to a processor and which, when executed by the processor, causes the processor to carry out a machine learning algorithm (support vector machine—SVM) that predicts the efficacy of a sgRNA based solely on the primary sequence of the sgRNA. It also relates to a (non-transitory) computer readable medium carrying out said sequence of instructions.

In another aspect, the invention provides for a method of knocking out in parallel every gene in the genome, the method comprising contacting a population of cells with a composition comprising a vector system comprising one or more packaged vectors comprising a) a first regulatory element operably linked to a CRISPR-Cas system chimeric RNA (chiRNA) polynucleotide sequence that targets a DNA molecule encoding a gene product,
    wherein the polynucleotide sequence comprises
        (a) a guide sequence capable of hybridizing to a target sequence,
        (b) a tracr mate sequence, and
        (c) a tracr sequence, and
b) a second regulatory element operably linked to a Cas protein and a selection marker,
wherein components (a) and (b) are located on same or different vectors of the system,
wherein each cell is transfected with a single packaged vector, selecting for successfully transfected cells,
wherein when transcribed, the tracr mate sequence hybridizes to the tracr sequence and the guide sequence directs sequence-specific binding of a CRISPR complex to a target sequence in the genomic loci of the DNA molecule encoding the gene product,
wherein the CRISPR complex comprises a CRISPR enzyme complexed with (1) the guide sequence that is hybridized to the target sequence, and (2) the tracr mate sequence that is hybridized to the tracr sequence,
wherein the guide sequence is selected from the library of the invention,
wherein the guide RNAs target the genomic loci of the DNA molecule encoding the gene product and the CRISPR enzyme cleaves the genomic loci of the DNA molecule encoding the gene product and whereby each cell in the population of cells has a unique gene knocked out in parallel. In preferred embodiments, the cell is a eukaryotic cell. In further embodiments the vector is a lentivirus, a adenovirus or a AAV and/or the first regulatory element is a U6 promoter and/or the second regulatory element is an EFS promoter, and/or the vector system comprises one vector and/or the CRISPR enzyme is Cas9.

The invention also encompasses methods of selecting individual cell knock outs that survive under a selective pressure, the method comprising contacting a population of cells with a composition comprising a vector system comprising one or more packaged vectors comprising a) a first regulatory element operably linked to a CRISPR-Cas system chimeric RNA (chiRNA) polynucleotide sequence that targets a DNA molecule encoding a gene product,
    wherein the polynucleotide sequence comprises
        (a) a guide sequence capable of hybridizing to a target sequence,
        (b) a tracr mate sequence, and
        (c) a tracr sequence, and
b) a second regulatory element operably linked to a Cas protein and a selection marker,
wherein components (a) and (b) are located on same or different vectors of the system,
wherein each cell is transfected with a single packaged vector, selecting for successfully transfected cells,
wherein when transcribed, the tracr mate sequence hybridizes to the tracr sequence and the guide sequence directs sequence-specific binding of a CRISPR complex to a target sequence in the genomic loci of the DNA molecule encoding the gene product,
wherein the CRISPR complex comprises a CRISPR enzyme complexed with (1) the guide sequence that is hybridized to the target sequence, and (2) the tracr mate sequence that is hybridized to the tracr sequence, wherein the guide sequence is selected from the library of the invention,
wherein the guide RNAs target the genomic loci of the DNA molecule encoding the gene product and the CRISPR enzyme cleaves the genomic loci of the DNA molecule encoding the gene product, whereby each cell in the population of cells has a unique gene knocked out in parallel,
applying the selective pressure,
and selecting the cells that survive under the selective pressure.
In preferred embodiments, the selective pressure is application of a drug, FACS sorting of cell markers or aging and/or the vector is a lentivirus, a adenovirus or a AAV and/or the first regulatory element is a U6 promoter and/or the second regulatory element is an EFS promoter, and/or the vector system comprises one vector and/or the CRISPR enzyme is Cas9.

In other aspects, the invention encompasses methods of identifying the genetic basis of one or more medical symptoms exhibited by a subject, the method comprising obtaining a biological sample from the subject and isolating a population of cells having a first phenotype from the biological sample;
contacting the cells having the first phenotype with a composition comprising a vector system comprising one or more packaged vectors comprising
a) a first regulatory element operably linked to a CRISPR-Cas system chimeric RNA (chiRNA) polynucleotide sequence that targets a DNA molecule encoding a gene product,
   wherein the polynucleotide sequence comprises
   (a) a guide sequence capable of hybridizing to a target sequence,
   (b) a tracr mate sequence, and
   (c) a tracr sequence, and
b) a second regulatory element operably linked to a Cas protein and a selection marker,
wherein components (a) and (b) are located on same or different vectors of the system,
wherein each cell is transfected with a single packaged vector, selecting for successfully transfected cells,
wherein when transcribed, the tracr mate sequence hybridizes to the tracr sequence and the guide sequence directs sequence-specific binding of a CRISPR complex to a target sequence in the genomic loci of the DNA molecule encoding the gene product,
wherein the CRISPR complex comprises a CRISPR enzyme complexed with (1) the guide sequence that is hybridized to the target sequence, and (2) the tracr mate sequence that is hybridized to the tracr sequence,
wherein the guide sequence is selected from the library of the invention,
wherein the guide RNAs target the genomic loci of the DNA molecule encoding the gene product and the CRISPR enzyme cleaves the genomic loci of the DNA molecule encoding the gene product, whereby each cell in the population of cells has a unique gene knocked out in parallel,
applying the selective pressure,
selecting the cells that survive under the selective pressure,
determining the genomic loci of the DNA molecule that interacts with the first phenotype and identifying the genetic basis of the one or more medical symptoms exhibited by the subject.
In preferred embodiments, the selective pressure is application of a drug, FACS sorting of cell markers or aging and/or the vector is a lentivirus, a adenovirus or a AAV and/or the first regulatory element is a U6 promoter and/or the second regulatory element is an EFS promoter, and/or the vector system comprises one vector and/or the CRISPR enzyme is Cas9.

The invention also comprehends kit comprising the library of the invention. In certain aspects, wherein the kit comprises a single container comprising vectors comprising the library of the invention. In other aspects, the kit comprises a single container comprising plasmids comprising the library of the invention. The invention also comprehends kits comprising a panel comprising a selection of unique CRISPR-Cas system guide sequences from the library of the invention, wherein the selection is indicative of a particular physiological condition. In preferred embodiments, the targeting is of about 100 or more sequences, about 1000 or more sequences or about 20,000 or more sequences or the entire genome. In other embodiments a panel of target sequences is focused on a relevant or desirable pathway, such as an immune pathway or cell division.

In one aspect, the invention provides a genome wide library comprising a plurality of unique CRISPR-Cas system guide sequences that are capable of targeting a plurality of target sequences in genomic loci of a plurality of genes, wherein said targeting results in a knockout of gene function. In preferred embodiments of the invention the unique CRISPR-Cas system guide sequences are selected by an algorithm that predicts the efficacy of the guide sequences based on the primary nucleotide sequence of the guide sequence and/or by a heuristic that ranks the guide sequences based on off target scores. An algorithm of the invention may be represented as in FIG. 9B. In certain embodiments of the invention, the guide sequences are capable of targeting a plurality of target sequences in genomic loci of a plurality of genes selected from the entire genome. In embodiments, the genes may represent a subset of the entire genome; for example, genes relating to a particular pathway (for example, an enzymatic pathway) or a particular disease or group of diseases or disorders may be selected. One or more of the genes may include a plurality of target sequences; that is, one gene may be targeted by a plurality of guide sequences. In certain embodiments, a knockout of gene function is not essential, and for certain applications, the invention may be practiced where said targeting results only in a knockdown of gene function. However, this is not preferred.
In other embodiments, the genomic library comprises guide sequences having a % GC nucleotide content between 20-80%, more preferably between 30-70%. In a further embodiment, the guide sequences target constitutive exons downstream of a start codon of the gene. In an advantageous embodiment, the guide sequences target either a first or a second exon of the gene. In yet another embodiment, the guide sequences target a non-transcribed strand of the genomic loci of the gene. The genomic libraries of the invention comprehend the guide sequence being 20 nucleotides long and likelihood of nucleotide T being at nucleotide position 17, 18, 19 or 20 being less than 20%. In additional embodiments, the guide sequences with the lowest off target scores are highly ranked and are selected. Furthermore, in preferred embodiments, the guide sequences do not have off target scores greater than 400.

In another aspect, the invention provides for a method of knocking out in parallel every gene in the genome, the method comprising contacting a population of cells with a composition comprising a vector system comprising one or more packaged vectors comprising a) a first regulatory element operably linked to a CRISPR-Cas system chimeric RNA (chiRNA) polynucleotide sequence that targets a DNA molecule encoding a gene product,
wherein the polynucleotide sequence comprises
(a) a guide sequence capable of hybridizing to a target sequence,
(b) a tracr mate sequence, and
(c) a tracr sequence, and
b) a second regulatory element operably linked to a Cas protein and a selection marker,
wherein components (a) and (b) are located on same or different vectors of the system,
wherein each cell is transduced with a single packaged vector,
selecting for successfully transduced cells,
wherein when transcribed, the tracr mate sequence hybridizes to the tracr sequence and the guide sequence directs sequence-specific binding of a CRISPR complex to a target sequence in the genomic loci of the DNA molecule encoding the gene product,
wherein the CRISPR complex comprises a CRISPR enzyme complexed with (1) the guide sequence that is hybridized to the target sequence, and (2) the tracr mate sequence that is hybridized to the tracr sequence,
wherein the guide sequence is selected from the library of the invention,
wherein the guide sequence targets the genomic loci of the DNA molecule encoding the gene product and the CRISPR enzyme cleaves the genomic loci of the DNA molecule encoding the gene product and whereby each cell in the population of cells has a unique gene knocked out in parallel. In preferred embodiments, the cell is a eukaryotic cell. The eukaryotic cell may be a plant or animal cell; for example, algae or microalgae; vertebrate, preferably mammalian, including murine, ungulate, primate, human; insect. In further embodiments the vector is a lentivirus, an adenovirus or an AAV and/or the first regulatory element is a U6 promoter and/or the second regulatory element is an EFS promoter or a doxycycline inducible promoter, and/or the vector system comprises one vector and/or the CRISPR enzyme is Cas9. In aspects of the invention the cell is a eukaryotic cell, preferably a human cell. In a further embodiment the cell is transduced with a multiplicity of infection (MOI) of 0.3-0.75, preferably, the MOI has a value close to 0.4, more preferably the MOI is 0.3 or 0.4.

The invention also encompasses methods of selecting individual cell knock outs that survive under a selective pressure, the method comprising contacting a population of cells with a composition comprising a vector system comprising one or more packaged vectors comprising
a) a first regulatory element operably linked to a CRISPR-Cas system chimeric RNA (chiRNA) polynucleotide sequence that targets a DNA molecule encoding a gene product,
wherein the polynucleotide sequence comprises
(a) a guide sequence capable of hybridizing to a target sequence,
(b) a tracr mate sequence, and
(c) a tracr sequence, and
b) a second regulatory element operably linked to a Cas protein and a selection marker,
wherein components (a) and (b) are located on same or different vectors of the system,
wherein each cell is transduced with a single packaged vector,
selecting for successfully transduced cells,
wherein when transcribed, the tracr mate sequence hybridizes to the tracr sequence and the guide sequence directs sequence-specific binding of a CRISPR complex to a target sequence in the genomic loci of the DNA molecule encoding the gene product,
wherein the CRISPR complex comprises a CRISPR enzyme complexed with (1) the guide sequence that is hybridized to the target sequence, and (2) the tracr mate sequence that is hybridized to the tracr sequence,
wherein the guide sequence is selected from the library of the invention,
wherein the guide sequence targets the genomic loci of the DNA molecule encoding the gene product and the CRISPR enzyme cleaves the genomic loci of the DNA molecule encoding the gene product, whereby each cell in the population of cells has a unique gene knocked out in parallel,
applying the selective pressure,
and selecting the cells that survive under the selective pressure.

In preferred embodiments, the selective pressure is application of a drug, FACS sorting of cell markers or aging and/or the vector is a lentivirus, a adenovirus or a AAV and/or the first regulatory element is a U6 promoter and/or the second regulatory element is an EFS promoter or a doxycycline inducible promoter, and/or the vector system comprises one vector and/or the CRISPR enzyme is Cas9. In a further embodiment the cell is transduced with a multiplicity of infection (MOI) of 0.3-0.75, preferably, the MOI has a value close to 0.4, more preferably the MOI is 0.3 or 0.4. In aspects of the invention the cell is a eukaryotic cell. The eukaryotic cell may be a plant or animal cell; for example, algae or microalgae; vertebrate, preferably mammalian, including murine, ungulate, primate, human; insect. Preferably the cell is a human cell. In preferred embodiments of the invention, the method further comprises extracting DNA and determining the depletion or enrichment of the guide sequences by deep sequencing.

In other aspects, the invention encompasses methods of identifying the genetic basis of one or more medical symptoms exhibited by a subject, the method comprising obtaining a biological sample from the subject and isolating a population of cells having a first phenotype from the biological sample;
contacting the cells having the first phenotype with a composition comprising a vector system comprising one or more packaged vectors comprising
a) a first regulatory element operably linked to a CRISPR-Cas system chimeric RNA (chiRNA) polynucleotide sequence that targets a DNA molecule encoding a gene product,
wherein the polynucleotide sequence comprises
(a) a guide sequence capable of hybridizing to a target sequence,
(b) a tracr mate sequence, and
(c) a tracr sequence, and
b) a second regulatory element operably linked to a Cas protein and a selection marker,
wherein components (a) and (b) are located on same or different vectors of the system,
wherein each cell is transduced with a single packaged vector,
selecting for successfully transduced cells,
wherein when transcribed, the tracr mate sequence hybridizes to the tracr sequence and the guide sequence directs sequence-specific binding of a CRISPR complex to a target sequence in the genomic loci of the DNA molecule encoding the gene product,
wherein the CRISPR complex comprises a CRISPR enzyme complexed with (1) the guide sequence that is hybridized to the target sequence, and (2) the tracr mate sequence that is hybridized to the tracr sequence,
wherein the guide sequence is selected from the library of the invention,
wherein the guide sequence targets the genomic loci of the DNA molecule encoding the gene product and the CRISPR enzyme cleaves the genomic loci of the DNA molecule encoding the gene product, whereby each cell in the population of cells has a unique gene knocked out in parallel,
applying a selective pressure,
selecting the cells that survive under the selective pressure, determining the genomic loci of the DNA molecule that interacts with the first phenotype and identifying the genetic basis of the one or more medical symptoms exhibited by the subject. In preferred embodiments, the selective pressure is application of a drug, FACS sorting of cell markers or aging and/or the vector is a lentivirus, an adenovirus or an AAV and/or the first regulatory element is a U6 promoter and/or the second regulatory element is an EFS promoter or a doxycycline inducible promoter, and/or the vector system comprises one vector and/or the CRISPR enzyme is Cas9. In a further embodiment the cell is transduced with a multiplicity of infection (MOI) of 0.3-0.75, preferably, the MOI has a value close to 0.4, more preferably the MOI is 0.3 or 0.4. In aspects of the invention the cell is a eukaryotic cell, preferably a human cell.

The invention also comprehends kits comprising the libraries of the invention. In certain aspects, the kit comprises a single container comprising vectors comprising the library of the invention. In other aspects, the kit comprises a single container comprising plasmids comprising the library of the invention. The invention also comprehends kits comprising a panel comprising a selection of unique CRISPR-Cas system guide sequences from the library of the invention, wherein the selection is indicative of a particular physiological condition. In preferred embodiments, the targeting is of about 100 or more sequences, about 1000 or more sequences or about 20,000 or more sequences or the entire genome. In other embodiments a panel of target sequences is focused on a relevant or desirable pathway, such as an immune pathway or cell division.

The invention also provides a method for designing a genome-scale sgRNA library, the method comprising identifying early constitutive exons for all coding genes,
selecting sgRNAs to target these early constitutive exons by choosing sgRNAs that were predicted to have minimal off-target activity,
for each candidate exon, listing all possible S. pyogenes Cas9 sgRNA sequences of the form (N)20NGG as candidate targets,
mapping each 20mer candidate sgRNA to a precompiled index containing all 20mer sequences in the human genome followed by either NGG or NAG,
ranking sgRNAs for each exon based on the characterized sequence specificity of Cas9 nuclease by using the following heuristic:
  discarding sgRNAs with other targets in the genome that match exactly or differ by only 1 base,
  calculating for the remaining sgRNAs the following off target sore:

$$OS = \sum_{\text{off targets}} (\text{sum } mm \text{ location})(D(mm)/D(\max))$$

sum mm location=sum of the mismatch locations from 3' to 5'. The PAM (NGG) proximal base is 1 and the PAM distal base is 20.
D(mm)=distance in bp between mismatch locations.
D(max)=maximal possible distance between 2 or 3 mismatches.

In an aspect, the invention provides a non-human eukaryotic organism; preferably a multicellular eukaryotic organism, comprising a eukaryotic host cell according to any of the described embodiments in which a candidate gene is knocked down or knocked out. Preferably the gene is knocked out. In other aspects, the invention provides a eukaryotic organism; preferably a multicellular eukaryotic organism, comprising a eukaryotic host cell which has been altered according to any of the described embodiments. The organism in some embodiments of these aspects may be an animal; for example a mammal. Also, the organism may be an arthropod such as an insect. The organism also may be a plant. Further, the organism may be a fungus. In some embodiments, the invention provides a set of non-human eukaryotic organisms, each of which comprises a eukaryotic host cell according to any of the described embodiments in which a candidate gene is knocked down or knocked out. In preferred embodiments, the set comprises a plurality of organisms, in each of which a different gene is knocked down or knocked out.

In some embodiments, the CRISPR enzyme comprises one or more nuclear localization sequences of sufficient strength to drive accumulation of said CRISPR enzyme in a detectable amount in the nucleus of a eukaryotic cell. In some embodiments, the CRISPR enzyme is a type I CRISPR system enzyme. In some embodiments, the CRISPR enzyme is a Cas9 enzyme. In some embodiments, the Cas9 enzyme is S. pneumoniae, S. pyogenes or S. thermophilus Cas9, and may include mutated Cas9 derived from these organisms. The enzyme may be a Cas9 homolog or ortholog. In some embodiments, the CRISPR enzyme is codon-optimized for expression in a eukaryotic cell. In some embodiments, the CRISPR enzyme directs cleavage of one or two strands at the location of the target sequence. In some embodiments, the CRISPR enzyme lacks DNA strand cleavage activity. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length. In an advantageous embodiment the guide sequence is 20 nucleotides in length.

Aspects of the invention allow for selection of specific cells without requiring a selection marker or a two-step process that may include a counter-selection system.

Aspects of the invention relate to rules for making potent sgRNAs. The invention comprehends machine learning algorithms (a support vector machine—SVM) that predicts the efficacy of a sgRNA based solely on the primary sequence of the sgRNA. This algorithm may be trained using data from ribosomal targeting sgRNAs or from any other exhaustive experimental data set. The trained algorithm may be used to predict the efficacy of an independent set of sgRNAs targeting other essential genes (obtained from screening data). The results indicated that the median sgRNA predicted to be "potent" versus the median sgRNA predicted to be "weak" is roughly 3× more effective. In preferred embodiments of the invention, in the last 4 positions of the guide sequence the nucleotide composition is preferably more Gs/Cs and less Ts.

As mentioned previously, a critical aspect of the invention is gene knock-out and not knock-down (which can be done with genome-wide siRNA or shRNA libraries). Applicants have provided the first demonstration of genome-wide knockouts that are barcoded and can be easily readout with next generation sequencing. Every single gene (or a subset of desired genes, for example, those relating to a particular enzymatic pathway or the like) may be knocked OUT in parallel. This allows quantification of how well each gene KO confers a survival advantage with the selective pressure of the screen. In a preferred embodiment, the invention has advantageous pharmaceutical application, e.g., the invention may be harnessed to test how robust any new drug designed to kill cells (eg. chemotherapeutic) is to mutations that KO genes. Cancers mutate at an exceedingly fast pace and the libraries and methods of the invention may be used in functional genomic screens to predict the ability of a chemotherapy to be robust to "escape mutations". (Refer to PLX data in BRAF V600E mutant A375 cells in Example 9. Other mutations (eg. NF1, NF2, MED12) allow escape from the killing action of PLX.)

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. These and other embodiments are disclosed or are obvious from and encompassed by, the following Detailed Description.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1A-G show A pooled approach for genetic screening in mammalian cells using a lentiviral CRISPR/Cas9 system (A) Outline of sgRNA library construction and genetic screening strategy (B) Immunoblot analysis of wild-type KBM7 cells and KBM7 cells transduced with a doxycycline inducible FLAG-Cas9 construct upon doxycycline induction. S6K1 was used as a loading control. (C) Sufficiency of single copy sgRNAs to induce genomic cleavage. Cas9-expressing KBM7 cells were transduced with AAVS1-targeting sgRNA lentivirus at low MOI. The SURVEYOR mutation detection assay was performed on cells at the indicated days post-infection (dpi). Briefly, mutations resulting from cleavage of the AAVS1 locus were detected through PCR amplification of a 500-bp amplicon flanking the target sequence, re-annealing of the PCR product and selective digestion of mismatched heteroduplex fragments. (D) Characterization of mutations induced by CRISPR/Cas9 as analyzed by high-throughput sequencing. (E) sgRNA library design pipeline. (F) Example of sgRNAs designed for PSMA 4. sgRNAs targeting constitutive exonic coding sequences nearest to the start codon were chosen for construction. (G) Composition of genome-scale sgRNA library.

FIGS. 2A-G show Resistance screens using CRISPR/Cas9. (A) Raw abundance (%) of sgRNA barcodes after 12 days of selection with 6-thioguanine (6-TG). (B) Mismatch repair (MMR) deficiency confers resistance to 6-TG. Diagram depicts cellular DNA repair processes. Only sgRNAs targeting components of the DNA MMR pathway were enriched. Diagram modified and adapted from. (C) Primary etoposide screening data. The count for a sgRNA is defined as the number of reads that perfectly match the sgRNA target sequence. (D) sgRNAs from both screens were ranked by their differential abundance between the treated versus untreated populations. For clarity, sgRNAs with no change in abundance are omitted. (E) Gene hit identification by comparing differential abundances of all sgRNAs targeting a gene to differential abundances of non-targeting sgRNAs in a one-sided Kolmogorov-Smirnov test. p-values are corrected for multiple hypothesis testing. (F) Immunoblot analysis of WT and sgRNA-modified HL60 cells 1 week after infection. S6K1 was used as a loading control. (G) Viability, as measured by cellular ATP concentration, of WT and sgRNA-modified HL60 cells at indicated etoposide concentrations. Error bars denote standard deviation (n=3).

FIGS. 3A-G shows Negative selection screens using CRISPR/Cas9 reveal rules governing sgRNA potency. (A) Selective depletion of sgRNAs targeting exons of BCR and ABL1 present in the fusion protein. Individual sgRNAs are plotted according to their target sequence position along each gene and the height of each bar indicates the level of depletion observed. Boxes indicate individual exons. (B) Cas9-dependent depletion of sgRNAs targeting ribosomal proteins. Cumulative distribution function plots of log 2 fold changes in sgRNA abundance before and after twelve cell doublings in Cas9-KBM7, Cas9-HL60 and WT-KBM7 cells. (C) Requirement of similar sets of ribosomal protein genes for proliferation in the HL60 and KBM7 cells. Gene scores are defined as the median $\log_2$ fold change of all sgRNAs targeting a gene. (D) Depleted sgRNAs target genes involved in fundamental biological processes. Gene Set Enrichment Analysis was performed on genes ranked by their combined depletion scores from screens in HL60 and KBM7 cells. Vertical lines underneath the x-axis denote members of the gene set analyzed. (E) Features influencing sgRNA efficacy. Depletion ($\log_2$ fold change) of sgRNAs targeting ribosomal protein genes was used as an indicator of sgRNA potency. Correlation between log 2 fold changes and spacer % GC content (left), exon position targeted (middle) and strand targeted (right) are depicted. (*p<0.05) (F) sgRNA target sequence preferences for Cas9 loading and cleavage efficiency. Position-specific nucleotide preferences for Cas9 loading are determined by counting sgRNAs bound to Cas9 normalized to the number of corresponding genomic integrations. Heatmaps depict sequence-dependent variation in Cas9 loading (top) and ribosomal protein gene-targeting sgRNA depletion (bottom). The color scale represents the median value (of Cas9 affinity or log 2 fold-change) for all sgRNAs with the specified nucleotide at the specified position. (G) sgRNA potency prediction. Ribosomal protein gene-targeting sgRNAs were designated as 'weak' or 'potent' based their log 2 fold change and used to train a support-vector-machine (SVM) classifier. As an independent test, the SVM was used to predict the potency of sgRNAs targeting 400 essential non-ribosomal genes. (*$p<0.05$).

FIGS. 8A-D show z-score analysis of positive selection screens. (A) z-scores of all sgRNAs targeting hit genes and non-targeting controls in the 6-TG screen. A sgRNA 'scores' if $z>2$. (B) Perfect discrimination between true and false positives is achieved at this significance threshold. (C) z-scores of all sgRNAs targeting hit genes and non-targeting controls in the etoposide screens. A sgRNA 'scores' if $z>2$. (D) Perfect discrimination between true and false positives is achieved at this significance threshold.

Figures 2A, 2B:
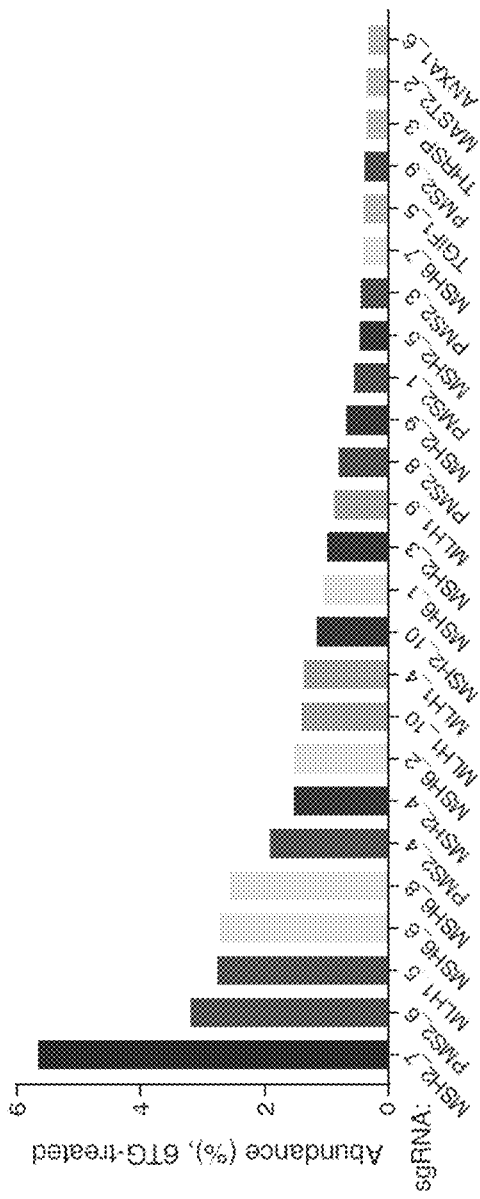

The figures herein are for illustrative purposes only and are not necessarily drawn to scale.

DETAILED DESCRIPTION OF THE INVENTION

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,697,359, 8,771,945, 8,795,965, 8,865,406 and 8,871,445; US Patent Publications US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486); PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO2014/093701 (PCT/US2013/074800), and WO2014/018423 (PCT/US2013/051418); U.S. provisional patent applications 61/961,980 and 61/963,643 each entitled FUNCTIONAL GENOMICS USING CRISPR-CAS SYSTEMS, COMPOSITIONS, METHODS, SCREENS AND APPLICATIONS THEREOF, filed Oct. 28 and Dec. 9, 2013 respectively; PCT/US2014/041806, filed Jun. 10, 2014, U.S. provisional patent applications 61/836,123, 61/960,777 and 61/995,636, filed on Jun. 17, 2013, Sep. 25, 2013 and Apr. 15, 2014, and PCT/US13/74800, filed Dec. 12, 2013.: Reference is also made to U.S. provisional patent applications 61/736,527, 61/748,427, 61/791,409 and 61/835,931, filed on Dec. 12, 2012, Jan. 2, 2013, Mar. 15, 2013 and Jun. 17, 2013, respectively. Reference is also made to U.S. provisional applications 61/757,972 and 61/768,959, filed on Jan. 29, 2013 and Feb. 25, 2013, respectively. Reference is also made to U.S. provisional patent applications 61/835,931, 61/835,936, 61/836,127, 61/836,101, 61/836,080 and 61/835,973, each filed Jun. 17, 2013. Each of these applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these applications and the appln cited documents) are incorporated herein by reference to the same extent as if each individual document was specifically and individually indicated to be incorporated by reference. Citations for documents cited herein may also be found in the foregoing herein-cited documents, as well as those hereinbelow cited.

Also with respect to general information on CRISPR-Cas Systems, mention is made of:

- Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121): 819-23 (2013);
- RNA-guided editing of bacterial genomes using CRISPR-Cas systems. Jiang W., Bikard D., Cox D., Zhang F, Manraffini L A. Nat Biotechnol March; 31(3):233-9 (2013);
- One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4):910-8 (2013);
- Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. 2013 Aug. 22; 500(7463):472-6. doi: 10.1038/Nature2466. Epub 2013 Aug. 23;
- Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5. (2013);
- DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol 2013 Sep.; 31(9):827-32. doi: 10.1038/nbt.2647. Epub 2013 Jul. 21; Y Genome engineering using the CRISPR-Cas9 system. Ran, F A., Hsu, P D., Wright, J., Agarwala, V., Scott, D A., Zhang, F. Nature Protocols November; 8(11):2281-308. (2013);
- Genome-Scale CRISPR-Cas9 Knockout Screening in Human Cells. Shalem, O., Sanjana, N E., Hartenian, E., Shi, X., Scott, D A., Mikkelson, T., Hecki, D., Ebert, B L., Root, D E., Doench, J G., Zhang, F. Science December 12. (2013). [Epub ahead of print];
- Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27. (2014). 156 (5):935-49;
- Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. (2014) April 20. doi: 10.1038/nbt.2889,
- Development and Applications of CRISPR-Cas9 for Genome Engineering, Hsu et al, Cell 157, 1262-1278 (Jun. 5, 2014) (Hsu 2014),
- Genetic screens in human cells using the CRISPR/Cas9 system, Wang et al., Science. 2014 Jan. 3: 343(6166): 80-84. doi:10.1126/science.1246981, and
- Rational design of highly active sgRNAs for CRISPR-Cas9-mediated gene inactivation, Doench et al., Nature Biotechnology published online 3 Sep. 2014; doi: 10.1038/nbt.3026.

each of which is incorporated herein by reference, and discussed briefly below:

Cong et al. engineered type II CRISPR/Cas systems for use in eukaryotic cells based on both *Streptococcus thermophilus* Cas9 and also *Streptoccocus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR/Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Konermann et al. addressed the need in the art for versatile and robust technologies that enable optical and chemical modulation of DNA-binding domains based CRISPR Cas9 enzyme and also Transcriptional Activator Like Effectors.

Cas9 nuclease from the microbial CRISPR-Cas system is targeted to specific genomic loci by a 20 nt guide sequence, which can tolerate certain mismatches to the DNA target and thereby promote undesired off-target mutagenesis. To address this, Ran et al. described an approach that combined a Cas9 nickase mutant with paired guide RNAs to introduce targeted double-strand breaks. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors reported that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Hsu 2014 is a review article that discusses generally CRISPR-Cas9 history from yogurt to genome editing, including genetic screening of cells, that is in the information, data and findings of the applications in the lineage of this specification filed prior to Jun. 5, 2014. The general teachings of Hsu 2014 do not involve the specific models, animals of the instant specification.

Mention is also made of Tsai et al, "Dimeric CRISPR RNA-guided FokI nucleases for highly specific genome editing," Nature Biotechnology 32(6): 569-77 (2014), incorporated herein by reference.

With regard to US and PCT patent applications herein cited, and the practice of the instant invention, especially as to GeCKO libraries, the herein mentioned CDs (as filed in connection with U.S. applications 61/960,777 and 61/995,636) can be accessed and also the GeCKO library(ies) as have been deposited with the ATCC can be accessed. The GeCKO library(ies) have been deposited as plasmid library (ies) as follows:

(A) GeCKO1—library of sgRNA plasmids each encoding selected guide sequences and cloned into vector (lentiCRISPRv2)—ATCC Deposit No. PTA-121339;

(B) GeCKO2—half library A (human) sgRNA plasmids each encoding selected guide sequences and cloned into vector—ATCC Deposit No. PTA-121340;

(C) GeCKO2—half library B (human) of sgRNA plasmids each encoding selected guide sequences and cloned into vector—ATCC Deposit No. PTA-121341;

(D) GeCKO2—half library A (mouse) sgRNA plasmids each encoding selected guide sequences and cloned into vector—ATCC Deposit No. PTA-121342; and (E) GeCKO2—half library A (mouse) sgRNA plasmids each encoding selected guide sequences and cloned into vector—ATCC Deposit No. PTA-121343;

wherein "GeCKO" stands for Genome-scale CRISPR-Cas9 Knock Out". The various GeCKO libraries have been generated for targeting either human or mouse genomes and consist of a one vector system or a two vector system for delivery of short 20 bp sequences of the sgRNA with or without Cas9. The GeCKO1 library consists of specific sgRNA sequences for gene knock-out in either the human or mouse genome. The GeCKO2 libraries consist of specific sgRNA sequences for gene knock-out in either the human or mouse genome, wherein each species-specific library is delivered as two half-libraries (A and B). When used together, the A and B libraries contain 6 sgRNAs per gene (3 sgRNAs in each library) and may contain 4 sgRNAs per microRNA ("miRNA") for over 1000 miRNA per genome (1864 in human, 1175 in mouse). Any one or more GeCKO library may be used in any one of the methods or in any one of the kits of the present invention. The GeCKO libraries, and specifically each of (A) to (E), above, were deposited with the American Type Culture Collection (ATCC) on Jun. 10, 2014, and are further exemplified in ATCC Deposit Nos: PTA-121339, PTA-121340, PTA-121341, PTA-121342, PTA-121343, deposited on Jun. 10, 2014, as provided herein and in the compact discs (CDs) created Apr. 11, 2014, as filed in connection with U.S. applications 61/960,777 and 61/995,636, including as the information set forth in those US applications and the compact discs (CDs) filed therewith is presented herein via the ATCC Deposits.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non nucleotide components. A polynucleotide may be further modified after polymerization, such as by conjugation with a labeling component.

As used herein the term "candidate gene" refers to a cellular, viral, episomal, microbial, protozoal, fungal, animal, plant, chloroplastic, or mitochondrial gene. This term also refers to a microbial or viral gene that is part of a naturally occurring microbial or viral genome in a microbially or virally infected cell. The microbial or viral genome can be extrachromosomal or integrated into the host chromosome. This term also encompasses endogenous and exogenous genes, as well as cellular genes that are identified as ESTs. Often, the candidate genes of the invention are those for which the biological function is unknown. An assay of choice is used to determine whether or not the gene is associated with a selected phenotype upon regulation of candidate gene expression with systems of the invention. If the biological function is known, typically the candidate gene acts as a control gene, or is used to determine if one or more additional genes are associated with the same phenotype, or is used to determine if the gene participates with other genes in a particular phenotype.

A "selected phenotype" refers to any phenotype, e.g., any observable characteristic or functional effect that can be measured in an assay such as changes in cell growth, proliferation, morphology, enzyme function, signal transduction, expression patterns, downstream expression patterns, reporter gene activation, hormone release, growth factor release, neurotransmitter release, ligand binding, apoptosis, and product formation. Such assays include, e.g., transformation assays, e.g., changes in proliferation, anchorage dependence, growth factor dependence, foci formation, growth in soft agar, tumor proliferation in nude mice, and tumor vascularization in nude mice; apoptosis assays, e.g., DNA laddering and cell death, expression of genes involved in apoptosis; signal transduction assays, e.g., changes in intracellular calcium, cAMP, cGMP, IP3, changes in hormone and neurotransmitter release; receptor assays, e.g., estrogen receptor and cell growth; growth factor assays, e.g., EPO, hypoxia and erythrocyte colony forming units assays; enzyme product assays, e.g., FAD-2 induced oil desaturation; transcription assays, e.g., reporter gene assays; and protein production assays, e.g., VEGF ELISAs. A candidate gene is "associated with" a selected phenotype if modulation of gene expression of the candidate gene causes a change in the selected phenotype.

In aspects of the invention the terms "chimeric RNA", "chimeric guide RNA", "guide RNA", "single guide RNA" and "synthetic guide RNA" are used interchangeably and refer to the polynucleotide sequence comprising the guide sequence, the tracr sequence and the tracr mate sequence. The term "guide sequence" refers to the about 20 bp sequence within the guide RNA that specifies the target site and may be used interchangeably with the terms "guide" or "spacer". The term "tracr mate sequence" may also be used interchangeably with the term "direct repeat(s)".

As used herein the term "wild type" is a term of the art understood by skilled persons and means the typical form of an organism, strain, gene or characteristic as it occurs in nature as distinguished from mutant or variant forms.

As used herein the term "variant" should be taken to mean the exhibition of qualities that have a pattern that deviates from what occurs in nature.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 900, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refers to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogsteen binding, or in any other sequence specific manner. The complex may comprise two strands forming a duplex structure, three or more strands forming a multi stranded complex, a single self hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R.I. Freshney, ed. (1987)).

Several aspects of the invention relate to vector systems comprising one or more vectors, or vectors as such. Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990), the contents of which are incorporated herein by reference. Alternatively, the recombinant expression vector can be transcribed and translated in vitro, for example the lentiviral vectors encompassed in aspects of the invention may comprise a U6 RNA pol III promoter.

In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Advantageous vectors include lentiviruses, adenoviruses and adeno-associated viruses, and types of such vectors can also be selected for targeting particular types of cells. In aspects on the invention the vectors may include but are not limited to packaged vectors. In other aspects of the invention a population of cells or host cells may be transduced with a vector with a low multiplicity of infection (MOI). As used herein the MOI is the ratio of infectious agents (e.g. phage or virus) to infection targets (e.g. cell). For example, when referring to a group of cells inoculated with infectious virus particles, the multiplicity of infection or MOI is the ratio of the number of infectious virus particles to the number of target cells present in a defined space (e.g. a well in a plate). In embodiments of the invention the cells are transduced with an MOI of 0.3-0.75 or 0.3-0.5; in preferred embodiments, the MOI has a value close to 0.4 and in more preferred embodiments the MOI is 0.3. In aspects of the invention the vector library of the invention may be applied to a well of a plate to attain a transduction efficiency of at least 20%, 30%, 40%, 50%, 60%, 70%, or 80%. In a preferred embodiment the transduction efficiency is approximately 30% wherein it may be approximately 370-400 cells per lentiCRISPR construct. In a more preferred embodiment, it may be 400 cells per lentiCRISPR construct.

Vectors may be introduced and propagated in a prokaryote. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST)', maltose E binding protein, or protein A, respectively, to the target recombinant protein.

Examples of suitable inducible non-fusion *E. coli* expression vectors include pTrc (Amrann et al., (1988) *Gene* 69:301-315) and pET 11d (Studier et al., GENE EXPRESSION TECHNOLOGY: METHODS IN ENZYMOLOGY 185, Academic Press, San Diego, Calif. (1990) 60-89).

In some embodiments, a vector is a yeast expression vector. Examples of vectors for expression in yeast *Saccharomyces cerevisiae* include pYepSec1 (Baldari, et al., 1987. *EMBO J.* 6: 229-234), pMFa (Kuijan and Herskowitz, 1982. *Cell* 30: 933-943), pJRY88 (Schultz et al., 1987. *Gene* 54: 113-123), pYES2 (Invitrogen Corporation, San Diego, Calif.), and picZ (InVitrogen Corp, San Diego, Calif.).

In some embodiments, a vector drives protein expression in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156-2165) and the pVL series (Lucknow and Summers, 1989. *Virology* 170: 31-39).

In some embodiments, a vector is capable of driving expression of one or more sequences in mammalian cells using a mammalian expression vector. Examples of mammalian expression vectors include pCDM8 (Seed, 1987. *Nature* 329: 840) and pMT2PC (Kaufman, et al., 1987. *EMBO J.* 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268-277), lymphoid-specific promoters (Calame and Eaton, 1988. *Adv. Immunol.* 43: 235-275), in particular promoters of T cell receptors (Winoto and Baltimore, 1989. *EMBO. J.* 8: 729-733) and immunoglobulins (Baneiji, et al., 1983. *Cell* 33: 729-740; Queen and Baltimore, 1983. *Cell* 33: 741-748), neuron-specific promoters (e.g., the neurofilament promoter; Byrne and Ruddle, 1989. *Proc. Natl. Acad. Sci. USA* 86: 5473-5477), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374-379) and the α-fetoprotein promoter (Campes and Tilghman, 1989. *Genes Dev.* 3: 537-546).

In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., *J. Bacteriol.*, 169:5429-5433 [1987]; and Nakata et al., *J. Bacteriol.*, 171:3553-3556 [1989]), and associated genes. Similar interspersed SSRs have been identified in *Haloferax mediterranei, Streptococcus pyogenes, Anabaena*, and *Mycobacterium* tuberculosis (See, Groenen et al., *Mol. Microbiol.*, 10:1057-1065 [1993]; Hoe et al., *Emerg. Infect. Dis.*, 5:254-263 [1999]; Masepohl et al., *Biochim. Biophys. Acta* 1307:26-30 [1996]; and Mojica et al., *Mol. Microbiol.*, 17:85-93 [1995]). The CRISPR loci typically differ from other SSRs by the structure of the repeats, which have been termed short regularly spaced repeats (SRSRs) (Janssen et al., *OMICS J. Integ. Biol.*, 6:23-33 [2002]; and Mojica et al., *Mol. Microbiol.*, 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., *J. Bacteriol.*, 182:2393-2401 [2000]). CRISPR loci have been identified in more than 40 prokaryotes (See e.g., Jansen et al., *Mol. Microbiol.*, 43:1565-1575 [2002]; and Mojica et al., [2005]) including, but not limited to *Aeropyrum, Pyrobaculum, Silfolobus, Archaeoglobus, Haloarcula, Methanobacterium, Methanococcus, Methanosarcina, Methanopyrus, Pyrococcus, Picrophilus, Thermoplasma, Corynebacterium, Mycobacterium, Streptomyces, Aqifex, Porphyromonas, Chlorobium, Thermus, Bacillus, Listeria, Staphylococcus, Clostridium, Thermoanaerobacter, Mycoplasma, Fusobacterium, Azoarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema,* and *Thermotoga*.

In aspects of the invention functional genomics screens allow for discovery of novel human and mammalian therapeutic applications, including the discovery of novel drugs, for, e.g., treatment of genetic diseases, cancer, fungal, protozoal, bacterial, and viral infection, ischemia, vascular disease, arthritis, immunological disorders, etc. As used herein assay systems may be used for a readout of cell state or changes in phenotype include, e.g., transformation assays, e.g., changes in proliferation, anchorage dependence, growth factor dependence, foci formation, growth in soft agar, tumor proliferation in nude mice, and tumor vascularization in nude mice apoptosis assays, e.g., DNA laddering and cell death, expression of genes involved in apoptosis; signal transduction assays, e.g., changes in intracellular calcium, cAMP, cGMP, IP3, changes in hormone and neurotransmitter release; receptor assays, e.g., estrogen receptor and cell growth; growth factor assays, e.g., EPO, hypoxia and erythrocyte colony forming units assays; enzyme product assays, e.g., FAD-2 induced oil desaturation; transcription assays, e.g., reporter gene assays; and protein production assays, e.g., VEGF ELISAs.

Aspects of the invention relate to modulation of gene expression and modulation can be assayed by determining any parameter that is indirectly or directly affected by the expression of the target candidate gene. Such parameters include, e.g., changes in RNA or protein levels, changes in protein activity, changes in product levels, changes in downstream gene expression, changes in reporter gene transcription (luciferase, CAT, .beta.-galactosidase, .beta.-glucuronidase, GFP (see, e.g., Mistili & Spector, Nature Biotechnology 15:961-964 (1997)); changes in signal transduction, phosphorylation and dephosphorylation, receptor-ligand interactions, second messenger concentrations (e.g., cGMP, cAMP, IP3, and $Ca^{2+}$), cell growth, and neovascularization, etc., as described herein. These assays can be in vitro, in vivo, and ex vivo. Such functional effects can be measured by any means known to those skilled in the art, e.g., measurement of RNA or protein levels, measurement of RNA stability, identification of downstream or reporter gene expression, e.g., via chemiluminescence, fluorescence, calorimetric reactions, antibody binding, inducible markers, ligand binding assays; changes in intracellular second messengers such as cGMP and inositol triphosphate (IP3); changes in intracellular calcium levels; cytokine release, and the like, as described herein.

Several methods of DNA extraction and analysis are encompassed in the methods of the invention. As used herein "deep sequencing" indicates that the depth of the process is many times larger than the length of the sequence under study. Deep sequencing is encompassed in next generation sequencing methods which include but are not limited to single molecule real-time sequencing (Pacific Bio), Ion semiconductor (Ion torrent sequencing), Pyrosequencing (454), Sequencing by synthesis (Illumina), Sequencing by ligations (SOLiD sequencing) and Chain termination (Sanger sequencing).

To determine the level of gene expression modulated by the CRISPR-Cas system, cells contacted with the CRISPR-Cas system are compared to control cells, e.g., without the CRISPR-Cas system or with a non-specific CRISPR-Cas system, to examine the extent of inhibition or activation. Control samples may be assigned a relative gene expression activity value of 100%. Modulation/inhibition of gene expression is achieved when the gene expression activity value relative to the control is about 80%, preferably 50% (i.e., 0.5 times the activity of the control), more preferably 25%, more preferably 5-0/o. Modulation/activation of gene expression is achieved when the gene expression activity value relative to the control is 110%, more preferably 150% (i.e., 1.5 times the activity of the control), more preferably 200-500%, more preferably 1000-2000% or more.

In general, "CRISPR system" or the "CRISPR-Cas system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. In some embodiments, one or more elements of a CRISPR system is derived from a type I, type II, or type III CRISPR system. In some embodiments, one or more elements of a CRISPR system is derived from a particular organism comprising an endogenous CRISPR system, such as *Streptococcus pyogenes*. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In some embodiments, a target sequence is located in the nucleus or cytoplasm of a cell. In some embodiments, the target sequence may be within an organelle of a eukaryotic cell, for example, mitochondrion or chloroplast. A sequence or template that may be used for recombination into the targeted locus comprising the target sequences is referred to as an "editing template" or "editing polynucleotide" or "editing sequence". In aspects of the invention, an exogenous template polynucleotide may be referred to as an editing template. In an aspect of the invention the recombination is homologous recombination.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence. In some embodiments, the tracr sequence has sufficient complementarity to a tracr mate sequence to hybridize and participate in formation of a CRISPR complex. As with the target sequence, it is believed that complete complementarity is not needed, provided there is sufficient to be functional. In some embodiments, the tracr sequence has at least 50%, 60%, 70%, 80%, 90%, 95% or 99% of sequence complementarity along the length of the tracr mate sequence when optimally aligned. In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter.

In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell.

In some embodiments, a vector comprises a regulatory element operably linked to an enzyme-coding sequence encoding a CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of *S. pyogenes* Cas9 protein may be found in the SwissProt database under accession number Q99ZW2. In some embodiments, the unmodified CRISPR enzyme has DNA cleavage activity, such as Cas9. In some embodiments the CRISPR enzyme is Cas9, and may be Cas9 from *S. pyogenes* or *S. pneumoniae*. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. In aspects of the invention, nickases may be used for genome editing via homologous recombination.

In some embodiments, a Cas9 nickase may be used in combination with guide sequence(s), e.g., two guide sequences, which target respectively sense and antisense strands of the DNA target. This combination allows both strands to be nicked and used to induce NHEJ. Applicants have demonstrated (data not shown) the efficacy of two nickase targets (i.e., sgRNAs targeted at the same location but to different strands of DNA) in inducing mutagenic NHEJ. A single nickase (Cas9-D10A with a single sgRNA) is unable to induce NHEJ and create indels but Applicants have shown that double nickase (Cas9-D10A and two sgRNAs targeted to different strands at the same location) can do so in human embryonic stem cells (hESCs). The efficiency is about 50% of nuclease (i.e., regular Cas9 without D10 mutation) in hESCs.

As a further example, two or more catalytic domains of Cas9 (RuvC I, RuvC II, and RuvC III) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is less than about 25%, 10%, 5%, 1%, 0.1%, 0.01%, or lower with respect to its non-mutated form. Other mutations may be useful; where the Cas9 or other CRISPR enzyme is from a species other than *S. pyogenes*, mutations in corresponding amino acids may be made to achieve similar effects.

In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence may be selected to target any target sequence. In some embodiments, the target sequence is a sequence within a genome of a cell. Exemplary target sequences include those that are unique in the target genome. For example, for the S. pyogenes Cas9, a unique target sequence in a genome may include a Cas9 target site of the form NNNNNNNNNNNNNNNNNNNNNGG (SEQ ID NO: 1) where NNNNNNNNNNNNNGG (SEQ ID NO: 2) (N is A, G, T, or C; and N at position 21 in SEQ ID NO: 1 and position 13 is SEQ ID NO: 2 can be any nucleotide) has a single occurrence in the genome. A unique target sequence in a genome may include an S. pyogenes Cas9 target site of the form NNNNNNNNNNNNNNNNNNNNNGG (SEQ ID NO: 3) where NNNNNNNNNNNNGG (SEQ ID NO: 4) (N is A, G, T, or C; and N at position 21 in SEQ ID NO: 3 and position 13 in SEQ ID NO: 4 can be any nucleotide) has a single occurrence in the genome. For the S. thermophilus CRISPR1 Cas9, a unique target sequence in a genome may include a Cas9 target site of the form NNNNNNNNNNNNNNNNNNNNNAGAAWAGAAW (SEQ ID NO: 5) where NNNNNNNNNNNNNAGAAW (SEQ ID NO: 6) (N is A, G, T, or C; N at positions 21-22 in SEQ ID NO: 5 and positions 13-14 in SEQ ID NO: 6 can be any nucleotide; and W is A or T) has a single occurrence in the genome. A unique target sequence in a genome may include an S. thermophilus CRISPR1 Cas9 target site of the form NNNNNNNNNNNNNNNNNNNNAGAAW (SEQ ID NO: 7) where NNNNNNNNNNNNAGAAW (SEQ ID NO: 8) (N is A, G, T, or C; N at positions 21-22 in SEQ ID NO: 7 and positions 12-13 in SEQ ID NO: 8 can be any nucleotide; and W is A or T) has a single occurrence in the genome. For the S. pyogenes Cas9, a unique target sequence in a genome may include a Cas9 target site of the form NNNNNNNNNNNNNNNNNNNNNGGNG (SEQ ID NO: 9) where NNNNNNNNNNNNNGGNG (SEQ ID NO: 10) (N is A, G, T, or C; and N at positions 21 and 24 in SEQ ID NO: 11 and positions 12 and 15 in SEQ ID NO: 12 can be any nucleotide) has a single occurrence in the genome. A unique target sequence in a genome may include an S. pyogenes Cas9 target site of the form NNNNNNNNNNNNNNNNNNNNNGGNG (SEQ ID NO: 11) where NNNNNNNNNNNNGGNG (SEQ ID NO: 12) (N is A, G, T, or C; and N at positions 21 and 24 in SEQ ID NO: 11 and positions 12 and 15 in SEQ ID NO: 12 can be any nucleotide) has a single occurrence in the genome. In each of SEQ ID NOS: 1, 5, and 9, the "N" at positions 1-8 may be A, G, T, or C, and in each of SEQ ID NOS: 3, 7, and 11, the "N" at positions 1-9 may be A, G, T, or C, and need not be considered in identifying a sequence as unique.

In some embodiments, a guide sequence is selected to reduce the degree of secondary structure within the guide sequence. Secondary structure may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, *Cell* 106(1): 23-24; and P A Carr and G M Church, 2009, *Nature Biotechology* 27(12): 1151-62). Further algorithms may be found in U.S. application Ser. No. 61/836,080; Broad Reference BI-2013/004A); incorporated herein by reference.

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence.

In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. Preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In some embodiments, the single transcript further includes a transcription termination sequence; preferably this is a polyT sequence, for example six T nucleotides. Further non-limiting examples of single polynucleotides comprising a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator:

(1)
(SEQ ID NO: 13)
NNNNNNNNNNNNNNNNNNNNNgttttttgtactctcaagatttaGAAAtaaa
tcttgcagaagctacaaagataaggcttcatgccgaaatcaacaccctgt
cattttatggcagggtgttttcgttatttaaTTTTTT;

(2)
(SEQ ID NO: 14)
NNNNNNNNNNNNNNNNNNNNNgttttttgtactctcaGAAAtgcagaagcta
caaagataaggcttcatgccgaaatcaacaccctgtcattttatggcagg
gtgttttcgttatttaaTTTTTT;

(3)
(SEQ ID NO: 15)
NNNNNNNNNNNNNNNNNNNNNgttttttgtactctcaGAAAtgcagaagcta
caaagataaggcttcatgccgaaatcaacaccctgtcattttatggcagg
gtgtTTTTTT;

(4)
(SEQ ID NO: 16)
NNNNNNNNNNNNNNNNNNNNNgttttagagctaGAAAtagcaagttaaaat
aaggctagtccgttatcaacttgaaaaagtggcaccgagtcggtgcTTTT
TT;

(5)
(SEQ ID NO: 17)
NNNNNNNNNNNNNNNNNNNNNgttttagagctaGAAATAGcaagttaaaat
aaggctagtccgttatcaacttgaaaaagtgTTTTTTT;
and (6)
(SEQ ID NO: 18)
NNNNNNNNNNNNNNNNNNNNNgttttagagctagAAATAGcaagttaaaat
aaggctagtccgttatcaTTTTT.

In some embodiments, sequences (1) to (3) are used in combination with Cas9 from *S. thermophilus* CRISPR1. In some embodiments, sequences (4) to (6) are used in combination with Cas9 from *S. pyogenes*. In some embodiments, the tracr sequence is a separate transcript from a transcript comprising the tracr mate sequence.

In some embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) VP16 protein fusions. Additional domains that may form part of a fusion protein comprising a CRISPR enzyme are described in US20110059502, incorporated herein by reference. In some embodiments, a tagged CRISPR enzyme is used to identify the location of a target sequence.

In an aspect of the invention, a reporter gene which includes but is not limited to glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP), may be introduced into a cell to encode a gene product which serves as a marker by which to measure the alteration or modification of expression of the gene product. In a further embodiment of the invention, the DNA molecule encoding the gene product may be introduced into the cell via a vector. In a preferred embodiment of the invention the gene product is luciferase. In a further embodiment of the invention the expression of the gene product is decreased.

In one aspect, the invention provides kits containing any one or more of the elements disclosed in the above methods and compositions. In some embodiments, the kit comprises a vector system and instructions for using the kit. In some embodiments, the vector system comprises (a) a first regulatory element operably linked to a tracr mate sequence and one or more insertion sites for inserting a guide sequence upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence; and/or (b) a second regulatory element operably linked to an enzyme-coding sequence encoding said CRISPR enzyme comprising a nuclear localization sequence. Elements may be provided individually or in combinations, and may be provided in any suitable container, such as a vial, a bottle, or a tube. In some embodiments, the kit includes instructions in one or more languages, for example in more than one language.

In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element. In some embodiments, the kit comprises a homologous recombination template polynucleotide.

In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR enzyme complexed with a guide sequence hybridized to a target sequence within the target polynucleotide. The guide sequence is linked to a tracr mate sequence, which in turn hybridizes to a tracr sequence.

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence) Examples of PAM sequences are given in the examples section below, and the skilled person will be able to identify further PAM sequences for use with a given CRISPR enzyme.

The target polynucleotide of a CRISPR complex may include a number of disease-associated genes and polynucleotides as well as signaling biochemical pathway-associated genes and polynucleotides as listed in U.S. provisional patent applications 61/736,527 and 61/748,427 having Broad reference BI-2011/008/WSGR Docket No. 44063-701.101 and BI-2011/008/WSGR Docket No. 44063-701.102 respectively, both entitled SYSTEMS METHODS AND COMPOSITIONS FOR SEQUENCE MANIPULATION filed on Dec. 12, 2012 and Jan. 2, 2013, respectively, the contents of all of which are herein incorporated by reference in their entirety. The target polynucleotide of a CRISPR complex can be a gene of previously unknown function wherein its presence or absence in a screen (integrated barcode of the sgRNA) reveals details about its function. The target polynucleotide of a CRISPR complex may also be a gene whose interaction with the screening agent (eg. drug or other selection agent) is discovered through its presence or absence in cells (barcode of the sgRNA) in the screen. Hence, in an aspect of the invention new drugs or pharmaceutical compositions may be tested for performance against all possible genetic KOs (or a subset of possible KOs; for example, genes associated with a particular enzymatic pathway) to understand how different organisms, e.g., humans (who carry different genetic KOs) might react to the drug and in which genetic background the drug might work better or worse.

Examples of genes and genomic loci that may be targeted by the CRISPR-Cas system guide RNA sequences described in *Genetic screens in human cells using the CRISPR-Cas9 system*. Wang T, Wei J J, Sabatini D M, Lander E S. Science. 2014 Jan. 3; 343(6166):80-4. doi: 10.1126/science.1246981. Epub 2013 Dec. 12 and supplemental material; and in *Genome-scale CRISPR-Cas9 knockout screening in human cells*. Shalem O, Sanjana N E, Hartenian E, Shi X, Scott D A, Mikkelsen T S, Heckl D, Ebert B L, Root D E, Doench J G, Zhang F. Science. 2014 Jan. 3; 343(6166):84-7. doi: 10.1126/science.1247005. Epub 2013 Dec. 12 and supplemental material, the respective content of which is incorporated herein by reference; see also herein-cited US and PCT patent applications and ATCC Deposits concerning the GeCKO Library(ies), incorporated herein by reference.

These may include but are not limited to sequences associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level, it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

Examples of disease-associated genes and polynucleotides are available from the relevant literature, for example from McKusick-Nathans Institute of Genetic Medicine, Johns Hopkins University (Baltimore, Md.) and National Center for Biotechnology Information, National Library of Medicine (Bethesda, Md.), available on the World Wide Web. Mutations in these genes and pathways can result in production of improper proteins or proteins in improper amounts which affect function. Further examples of genes, diseases and proteins are hereby incorporated by reference from U.S. Provisional applications 61/736,527 and 61/748,427. Such genes, proteins and pathways may be the target polynucleotide of a CRISPR complex.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Genetic Screens in Human Cells Using the CRISPR/Cas9 System

The bacterial CRISPR-Cas9 system for genome editing has greatly expanded the toolbox for mammalian genetics, enabling the rapid generation of isogenic cell lines and mice with modified alleles. Here, Applicants described a pooled, loss-of-function genetic screening approach suitable for both positive and negative selection that uses a genome-scale lentiviral single guide RNA (sgRNA) library. sgRNA expression cassettes were stably integrated into the genome, which enabled a complex mutant pool to be tracked by massively parallel sequencing. Applicants used a library containing 73,000 sgRNAs to generate knockout collections and performed screens in two human cell lines. A screen for resistance to the nucleotide analog 6-thioguanine identified all expected members of the DNA mismatch repair pathway, while another for the DNA topoisomerase II (TOP2A) poison etoposide identified TOP2A, as expected, and also cyclin-dependent kinase 6, CDK6. A negative selection screen for essential genes identified numerous gene sets corresponding to fundamental processes. Finally, Applicants showed that sgRNA efficiency is associated with specific sequence motifs, enabling the prediction of potent sgRNAs. Collectively, these results establish Cas9/sgRNA screens as a powerful tool for systematic genetic analysis in mammalian cells.

A critical need in biology is the ability to efficiently identify the set of genes underlying a cellular process. In microorganisms, powerful methods allow systematic loss-of-function genetic screening. In mammalian cells, however, current screening methods fall short—primarily because of the difficulty of inactivating both copies of a gene in a diploid mammalian cell. Insertional mutagenesis screens in cell lines that are near-haploid or carry Blm mutations, that cause frequent somatic crossing-over, have proven powerful but are not applicable to most cell lines and suffer from integration biases of the insertion vectors. The primary solution has been to target mRNAs with RNA interference (RNAi). However, this approach is also imperfect as it only partially suppresses target gene levels and can have off-target effects on other mRNAs—resulting in false negative and false positive results. Thus, there remains an unmet need for an efficient, large-scale, loss of function screening method in mammalian cells.

Recently, the Clustered Regularly Interspaced Short Palindromic Repeats (CRISPR) pathway, which functions as an adaptive immune system in bacteria, has been co-opted to engineer mammalian genomes in an efficient manner. In this two-component system, a single guide RNA (sgRNA) directs the Cas9 nuclease to cause double-stranded cleavage of matching target DNA sequences. In contrast to previous genome-editing techniques, such as zinc-finger nucleases and TALENs, the target specificity of CRISPR-Cas9 is dictated by a 20-base pair sequence at the 5'-end of the sgRNA, allowing for much greater ease of construction of knockout reagents. Mutant cells lines and mice bearing multiple modified alleles may be generated with this technology.

Applicants explored the feasibility of using the CRISPR-Cas9 system to perform large-scale, loss-of-function screens in mammalian cells. The idea was to use a pool of sgRNA-expressing lentivirus to generate a library of knockout cells that could be screened under both positive and negative selection. Each sgRNA would serve as a distinct DNA barcode that can be used to count the number of cells carrying it using high-throughput sequencing (FIG. 1A). Pooled screening requires that single-copy sgRNA integrants are sufficient to induce efficient cleavage of both copies of a targeted locus. This contrasts with the high expression of sgRNAs achieved by transfection that is typically used to engineer a specific genomic change using the CRISPR-Cas9 system.

Applicants first tested the concept in the near-haploid, human KBM7 CML cell line, by creating a clonal derivative expressing the Cas9 nuclease (with a FLAG-tag at its N-terminus) under a doxycycline-inducible promoter (FIG. 1B). Transduction of these cells at low multiplicity of infection (MOI) with a lentivirus expressing a sgRNA targeting the endogenous AAVS1 locus revealed substantial cleavage at the AAVS1 locus 48 hours after infection (FIG. 1C). Moreover, because the sgRNA was stably expressed, genomic cleavage continued to increase over the course of the experiment. Deep sequencing of the locus revealed that repair of Cas9-induced double-strand breaks resulted in small deletions (<20 bp) in the target sequence, with tiny insertions or substitutions (<3 bp) occurring at a lower frequency (FIG. 1D). The vast majority of the lesions, occurring in a protein-coding region, would be predicted to give rise to a non-functional protein product, indicating that CRISPR-Cas9 is an efficient means of generating loss-of-function alleles.

Applicants also analyzed off-target activity of CRISPR-Cas9. Although the specificity of CRISPR/Cas9 has been extensively characterized in transfection-based settings, Applicants wanted to examine its off-target behavior in this system, where Cas9 and a single guide RNA targeting AAVS1 (sgAAVS1) were stably expressed for two weeks. Applicants compared the level of cleavage observed at the target locus (97%) to levels at 13 potential off-target cleavage sites in the genome (defined as sites differing by up to 3 bp from sgAAVS1). Minimal cleavage (<2.5%) was observed at all sites with one exception, which was the only site that had perfect complementarity in the 'seed' region (terminal 8 bp). On average, sgRNAs have ~2.2 such sites in the genome, almost always (as in this case) occurring in non-coding DNA and thus less likely to affect gene function. For the examination of potential sgRNA off-target sites, Applicants determined the expected number of potential off-target sites in the human genome and exome allowing for up to 3 mismatches in the non-seed region (first 12 base pairs) by the following calculation:

$$p_{20} = \left(\frac{1}{4}\right)^{20} = \text{probability of a perfect 20 base pair match}$$

$$p_{PAM} = \left(\frac{1}{2}\right)\left(\frac{1}{4}\right) =$$

$$\left(\frac{1}{8}\right) = \text{probability of a } PAM \text{ sequence match } (AG \text{ or } GG \text{ allowed})$$

$$MM_3 = \binom{12}{3}(4-1)^3 = \text{\# of 3 base pair mismatch combinations in non-seed region}$$

$$MM_2 = \binom{12}{2}(4-1)^2 = \text{\# of 2 base pair mismatch combinations in non-seed region}$$

$$MM_1 = \binom{12}{1}(4-1) = \text{\# of 1 base pair mismatch combinations in non-seed region}$$

$$PM = 1 = \text{perfect match in non-seed region}$$

$$S_{genome} = 3 \times 10^9 = \text{size of human genome}$$

$$S_{exome} = 5 \times 10^7 = \text{size of the human exome } (UTR + CDS)$$

$$OT_{Genome} = (p_{20})(p_{PAM})(MM_3 + MM_2 + MM_1 + PM)(S_{genome}) \approx$$

2.23 expected off-target sites in the genome per sgRNA $$OT_{Exome} = (p_{20})(p_{PAM})(MM_3 + MM_2 + MM_1 + PM)(S_{exome}) \approx$$

$$0.0072 \approx \frac{1}{27} \text{ expected off-target sites in the exome per } sgRNA$$

Figure 5A:
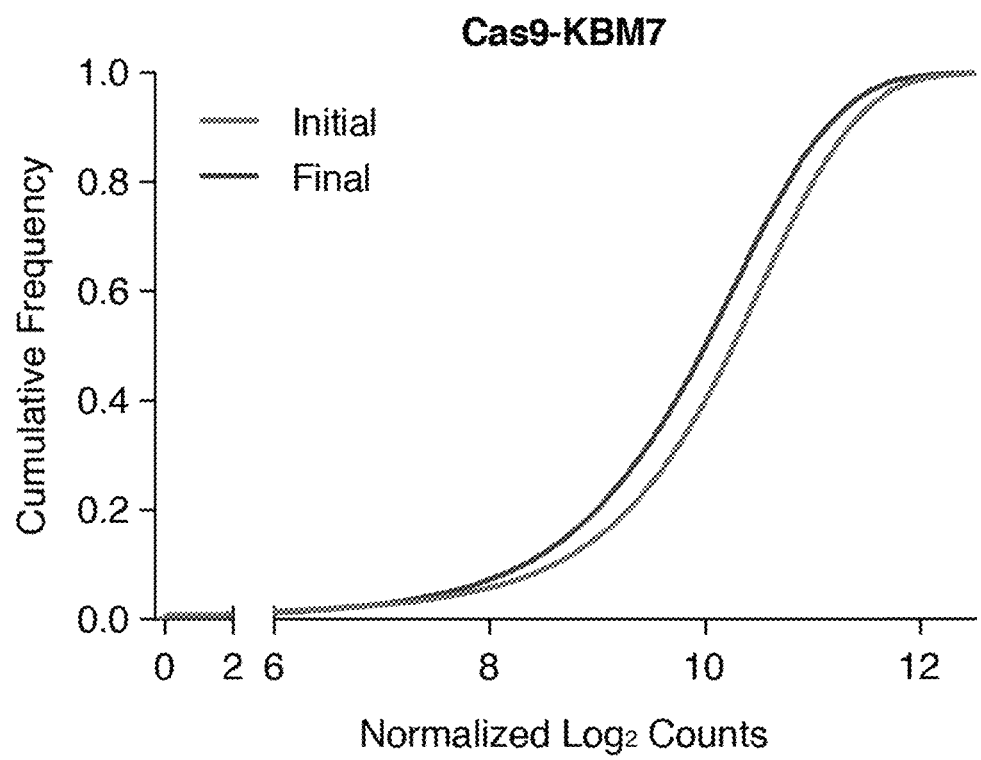
FIGS. 5A-B show Deep sequencing analysis of initial and final sgRNA library representation. (A) Cumulative distribution function plots of sgRNA barcodes 24 hours after infection and after twelve cell doublings in Cas9-KBM7 and (B) Cas9-HL60 cells.

To test the ability to simultaneously screen tens of thousands of sgRNAs, Applicants designed a sgRNA library with 73,151 members, consisting of multiple sgRNAs targeting 7,114 genes and 100 non-targeting controls (FIG. 1E and see *Genetic screens in human cells using the CRISPR-Cas93system*. Wang T, Wei J J, Sabatini D M, Lander E S. Science. 2014 Jan. 3; 343(6166):80-4. doi: 10.1126/science.1246981. Epub 2013 Dec. 12. and supplemental material, the respective content of which is incorporated herein by reference; providing annotations for the genome-scale sgRNA library containing spacer sequences and target gene information; see also herein-cited US and PCT patent applications and ATCC Deposits concerning the GeCKO Library (ies), all incorporated herein by reference). sgRNAs were designed against constitutive coding exons near the beginning of each gene and filtered for potential off-target effects based on sequence similarity to the rest of the human genome (FIG. 1F-G). The library included 10 sgRNAs for each of 7033 genes and all possible sgRNAs for each of the 84 genes encoding ribosomal proteins (FIG. 1H). To assess the effective representation of Applicants' microarray synthesized library, Applicants sequenced sgRNA barcodes from KBM7 cells 24 hours after infection with the entire lentiviral pool and were able to detect the overwhelming majority (>99° %) of Applicants' sgRNAs, with high uniformity across constructs (only 6-fold increase in abundance between the 10th and 90th percentiles) (FIG. 5A).

As an initial test of this approach, Applicants screened the library for genes that function in DNA mismatch repair (MMR). In the presence of the nucleotide analog 6-thioguanine (6-TG), MMR-proficient cells are unable to repair 6-TG-induced lesions and arrest at the G2-M cell-cycle checkpoint, while MMR-defective cells do not recognize the lesions and continue to divide. Applicants infected Cas9-KBM7 cells with the entire sgRNA library, cultured the cells in a concentration of 6-TG that is lethal to wild-type KBM7 cells, and sequenced the sgRNA barcodes in the final population. sgRNAs targeting the genes encoding the four components of the MMR pathway (MSH2, MSH6, MLH1 and PMS2) were dramatically enriched in the 6-TG-treated cells. At least four independent sgRNAs for each gene showed very strong enrichment and barcodes corresponding to these genes made up >30% of all barcodes (FIG. 2A-B). Strikingly, each of the twenty most abundant sgRNAs targeted one of these four genes. The fact that few of the other 73,000 sgRNAs scored highly in this assay suggests a low frequency of off-target effects.

Figure 2G:
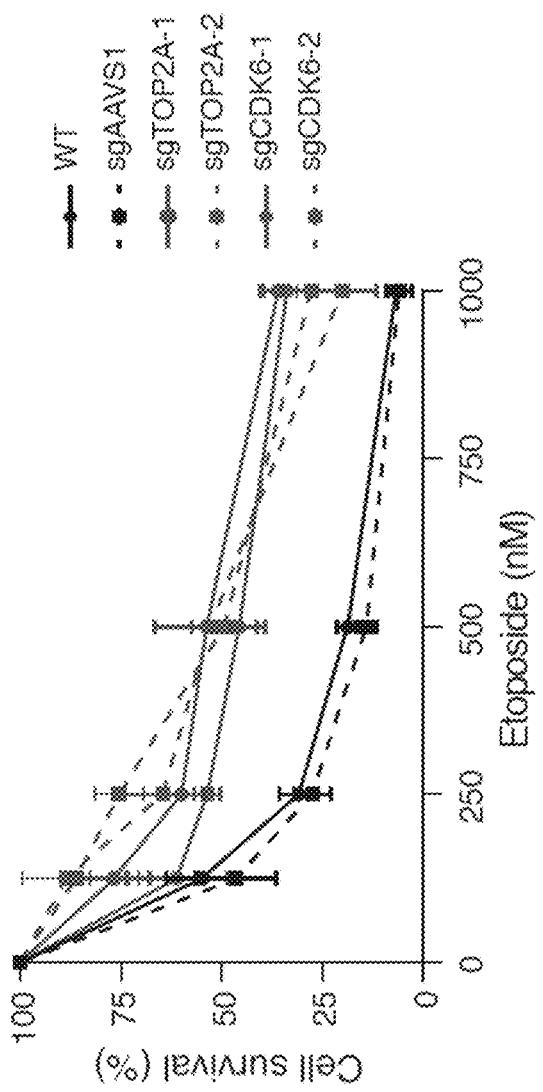
Figure 2F:
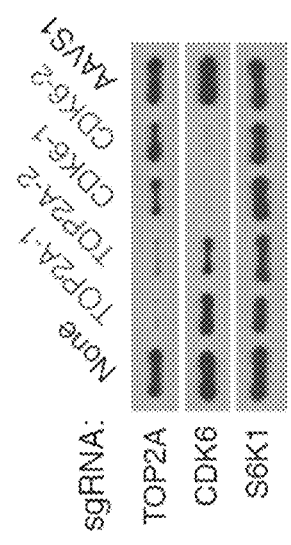

Applicants next addressed the challenge of loss of function screening in diploid cells, which require bi-allelic inactivation of a target gene. Applicants therefore generated an inducible Cas9 derivative of the HL60 pseudo-diploid human leukemic cell line. In both HL60 and KBM7 cells, Applicants screened for genes whose loss conferred resistance to etoposide, a chemotherapeutic agent that poisons DNA topoisomerase IIA (TOP2A). To identify hit genes, Applicants calculated the difference in abundance between the treated and untreated populations for each sgRNA, calculated a score for each gene by using a Kolmogorov-Smirnov test to compare the sgRNAs targeting the gene against the non-targeting control sgRNAs, and corrected for multiple hypothesis testing (FIG. 2C-E and see *Genetic screens in human cells using the CRISPR-Cas9 system*. Wang T, Wei J J, Sabatini D M, Lander E S. Science. 2014 Jan. 3; 343(6166):80-4. doi: 10.1126/science.1246981. Epub 2013 Dec. 12. and supplemental material, the respective content of which is incorporated herein by reference; and which shows gene-level data for etoposide screens in KBM7 and HL60 cells; see also herein-cited US and PCT patent applications and ATCC Deposits concerning the GeCKO Library(ies)). Identical genes were detected in both screens, with significance levels exceeding all other genes by more than 100-fold. As expected, loss of TOP2A itself conferred strong protection to etoposide. The screen also revealed a role for CDK6, a G1 cyclin-dependent kinase, in mediating etoposide-induced cytotoxicity. Notably, every one of the 20 sgRNAs in the library targeting TOP2A or CDK6 was strongly enriched (>90th percentile) in both screens, indicating that the effective coverage of Applicants' libraries is very high. Applicants generated isogenic HL60 cell lines with individual sgRNAs against TOP2A and CDK6 and, consistent with the screen results, these lines were much more resistant to etoposide than parental or sgAAVS1-modified HL60 cells (FIG. 2F-G). Thus, Applicants Cas9/sgRNA system enables large-scale positive selection loss-of-function screens.

To identify genes required for cellular proliferation Applicants screened for genes whose loss conferred a selective disadvantage on cells. Such a screen requires accurate identification of sgRNAs that are depleted from the final cell population. Importantly, a sgRNA will show depletion only if cleavage of the target gene occurs in the majority of cells carrying the construct.

Figure 3A:
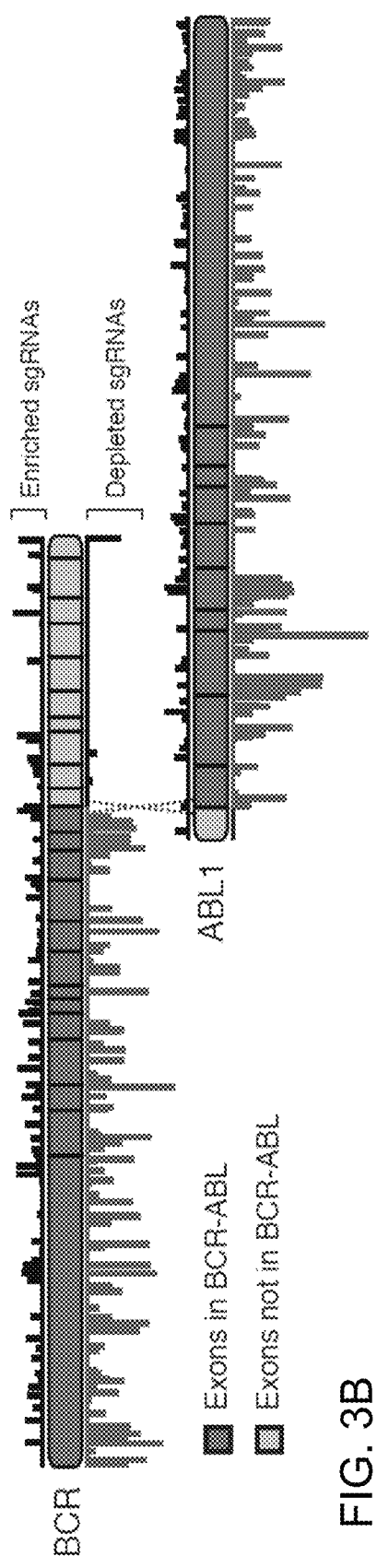

As an initial test, Applicants screened KBM7 cells with a small library containing sgRNAs targeting the BCR and ABL1 genes (see *Genetic screens in human cells using the CRISPR-Cas9 system*. Wang T, Wei J J, Sabatini D M, Lander E S. Science. 2014 Jan. 3; 343(6166):80-4. doi: 10.1126/science.1246981. Epub 2013 Dec. 12. and supplemental material, the respective content of which is incorporated herein by reference, providing annotations for the mini sgRNA library containing spacer sequences and target gene information; see also herein-cited US and PCT patent applications and ATCC Deposits concerning the GeCKO Library (ies)). The survival of KBM7 cells depends on the fusion protein produced by the BCR-ABL translocation. As expected, depletion was seen only for sgRNAs targeting the exons of BCR and ABL1 that encode the fusion protein, but not for those targeting the other exons of BCR and ABL1 (FIG. 3A).

Figure 5B:
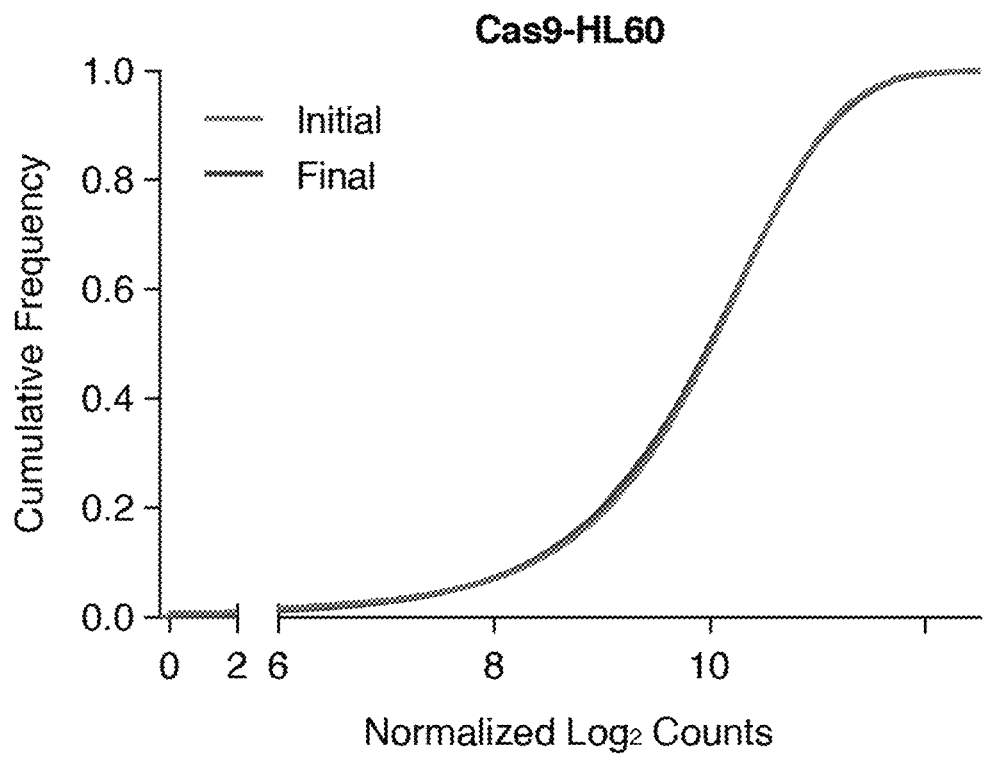

Applicants then infected Cas9-HL60, Cas9-KBM7, and WT KBM7 cells with the entire 73,000-member sgRNA library and used deep sequencing of the sgRNA barcodes to monitor the change in abundance of each sgRNA between the initial seeding and a final population obtained after twelve cell doublings (FIG. 5A-B).

Figure 3B:
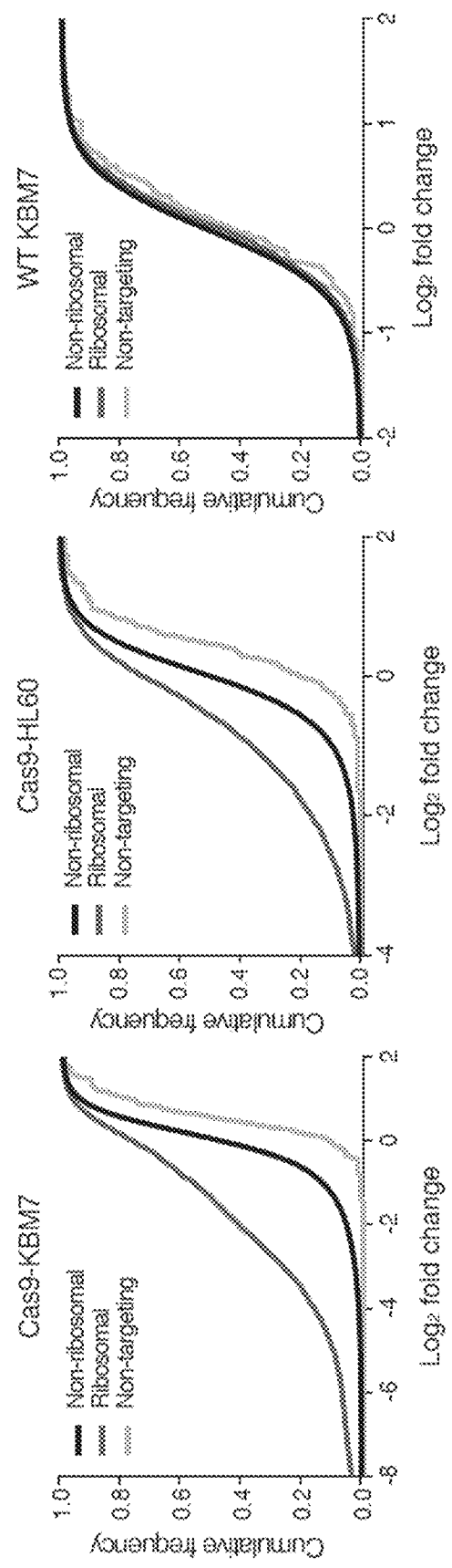
Figure 3D:
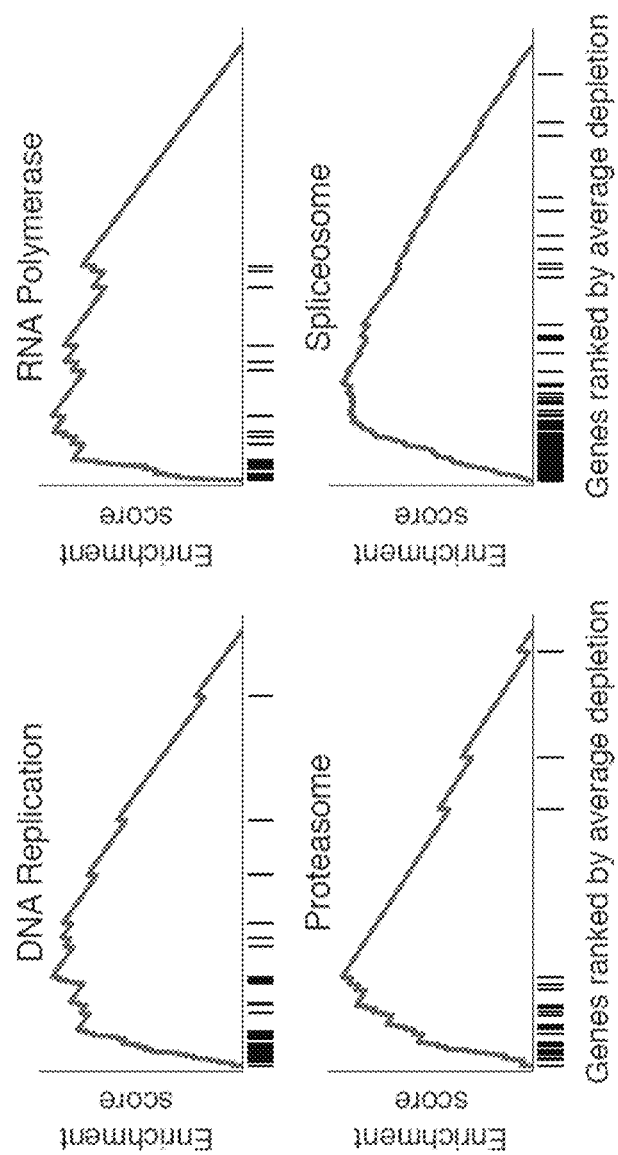
Figure 3C:
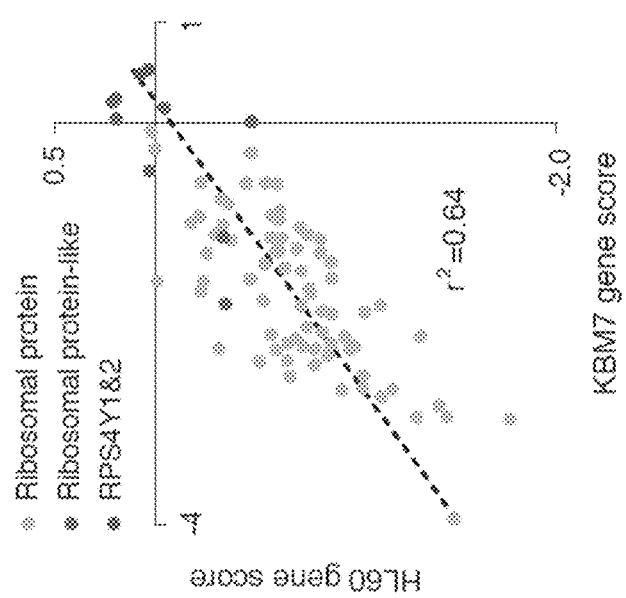

Applicants began by analyzing ribosomal proteins genes, for which the library contained all possible sgRNAs. Applicants observed strong Cas9-dependent depletion of sgRNAs targeting genes encoding ribosomal proteins, with good concordance between the sets of ribosomal protein genes essential for cell proliferation in the HL60 and KBM7 screens (the median sgRNA fold-change in abundance was used as a measure of gene essentiality) (FIG. 3B-C). Interestingly, a few ribosomal protein genes were not found to be essential. These were two genes encoded on chromosome Y (RPS4Y2, which is testes-specific, and RPS4Y1, which is expressed at low levels compared to its homolog RPS4X on chromosome X), and 'ribosome-like' proteins, which may be required only in select tissues and generally are lowly expressed in KBM7 cells.

Figures 4A, 4B:
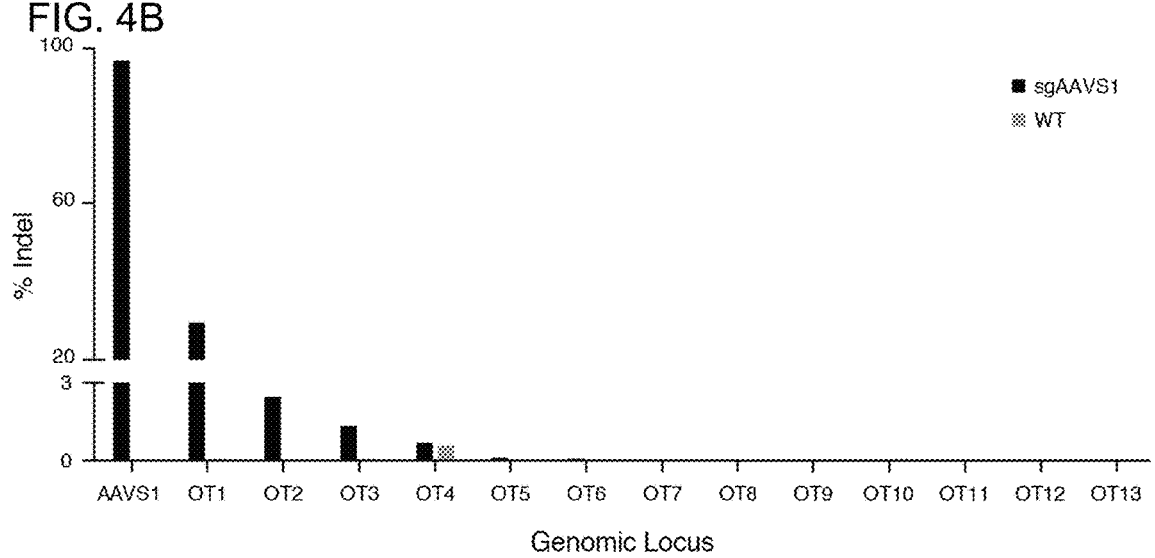
FIGS. 4A-B show Off-target cleavage analysis. (A) AAVS1 and predicted sgAAVS1 off-target (OT) sites were individually amplified in a nested PCR from genomic DNA from sgAAVS-modified and WT Cas9-KBM7 cells and analyzed by high-throughput sequencing. Figure discloses SEQ ID NOS 25-38, respectively, in order of appearance. (B) Barplot summary of the results.

FIG. 4A-B show Off-target cleavage analysis: (A) AAVS1 and predicted sgAAVS1 off-target (OT) sites were individually amplified in a nested PCR from genomic DNA from sgAAVS-modified and WT Cas9-KBM7 cells and analyzed by high-throughput sequencing. (B) Barplot summary of the results.

Figure 6A:
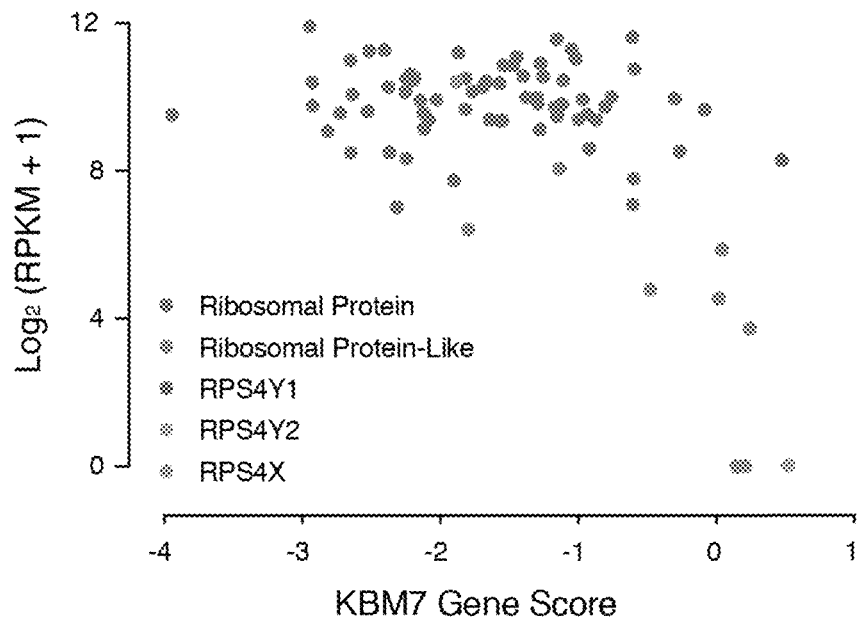
FIGS. 6A-B show Negative selection screens reveal essential genes. (A) Ribosomal protein gene essentiality correlates with expression. Ribosomal protein gene depletion scores from the negative selection screen in Cas9-KBM7 cells are plotted against transcript abundance as determined by RNA-seq analysis of the KBM7 cell line. (B) Gene depletion scores of all genes screened are well correlated between Cas9-KBM7 and Cas9-HL60 cells.
Figure 6B:
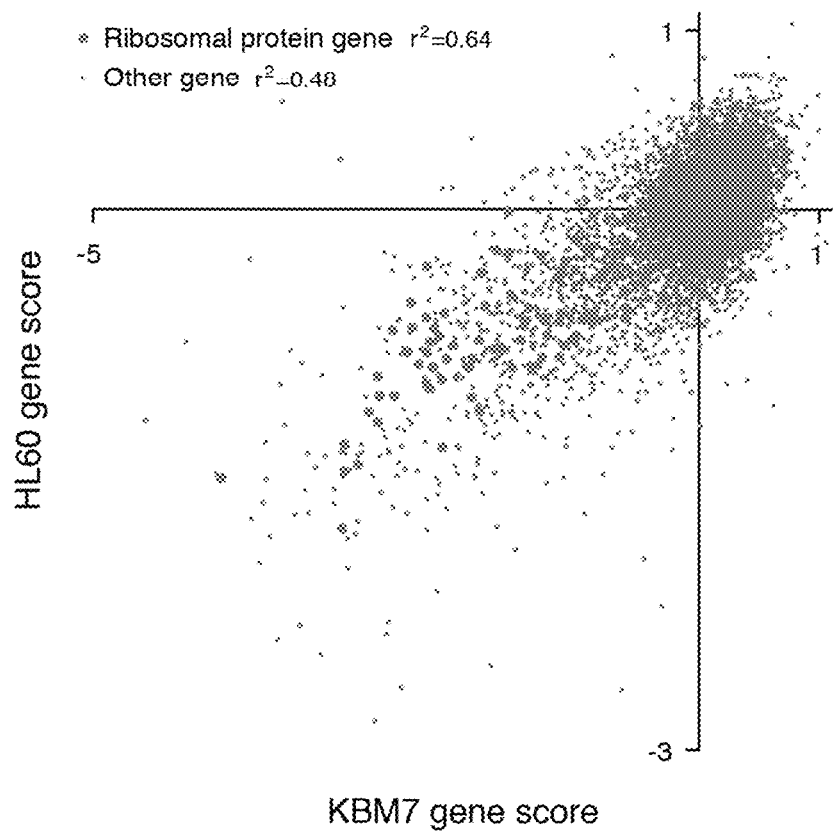

FIGS. 6A-B show Negative selection screens reveal essential genes: (A) Ribosomal protein gene essentiality correlates with expression. Ribosomal protein gene depletion scores from the negative selection screen in Cas9-KBM7 cells are plotted against transcript abundance as determined by RNA-seq analysis of the KBM7 cell line. (B) Gene depletion scores of all genes screened are well correlated between Cas9-KBM7 and Cas9-HL60 cells.

Applicants then turned attention to other genes within Applicants' dataset, for which ten sgRNAs were designed. As for the ribosomal genes, the essentiality scores of these genes were also strongly correlated between the two cells lines (see *Genetic screens in human cells using the CRISPR-Cas9 system*. Wang T, Wei J J, Sabatini D M, Lander E S. Science. 2014 Jan. 3; 343(6166):80-4. doi: 10.1126/science.1246981. Epub 2013 Dec. 12 and supplemental material, the respective content of which is incorporated herein by reference, providing Gene-level data for negative selection screens in KBM7 and HL60 cells; see also herein-cited US and PCT patent applications and ATCC Deposits concerning the GeCKO Library(ies)). For the twenty highest scoring genes, Applicants found independent evidence for essentiality, based primarily on data from large-scale functional studies in model organisms (Table 1).

TABLE 1

Independent evidence of essentiality for the top 20 non-ribosomal genes. Functional data from large-scale studies in model organisms and single gene studies in mice and human cell lines. 16 of 17 yeast homologs are essential. The sole except TPT1 is essential in mice and *C. elegans*.

| Rank | Gene | Name | Yeast homolog | Essential in yeast?[a] | Evidence in other organisms |
|---|---|---|---|---|---|
| 1 | SF3B3 | splicing factor 3b, subunit 3, 130 kDa | RSE1 | Yes | teg-4[b] CG13900[d] |
| 2 | RPP21 | ribonuclease P/MRP 21 kDa subunit | RPR2 | Yes | |
| 3 | C1orf109 | chromosome 1 open reading frame 109 | — | — | c1orf109[f] human |
| 4 | PCNA | proliferating cell nuclear antigen | POL30 | Yes | pcn-1[b] mus209[e] |
| 5 | CDAN1 | codanin 1 | — | — | dlt[e] mouse |
| 6 | PSMA7 | proteasome (prosome, macropain) subunit, alpha type, 7 | PRE6 | Yes | pas-4[b] |
| 7 | GTF2B | general transcription factor IIB | SUA7 | Yes | ttb-1[b] |
| 8 | ANAPC4 | anaphase promoting complex subunit 4 | APC4 | Yes | emb-30[c] |
| 9 | CDC16 | cell division cycle 16 | CDC16 | Yes | emb-27[b] |
| 10 | TPT1 | tumor protein, translationally-controlled 1 | TMA19 | NO | tct-1[c] mouse |
| 11 | SF3A3 | splicing factor 3a, subunit 3, 60 kDa | PRP9 | Yes | T13H5.4[b] noi[e] sf3a3[f] |
| 12 | PREB | prolactin regulatory element binding | SEC12 | Yes | sec-12[c] |
| 13 | HSPA9 | heat shock 70 kDa protein 9 (mortalin) | SSC1 | Yes | hsp-6[b] Hsc70-5[e] Hspa9b[f] |
| 14 | POLR2A | polymerase (RNA) II (DNA directed) polypeptide A, 220 kDa | RPO21 | Yes | ama-1[b] RpII215[d] |
| 15 | PCF11 | PCF11 cleavage and polyadenylation factor subunit | PCF11 | Yes | pcf-11[b] CG10228[d] |
| 16 | POLR2L | polymerase (RNA) II (DNA directed) polypeptide L, 7.6 kDa | RPB10 | Yes | rpb-10[b] rpb10[d] |
| 17 | SPC24 | SPC24, NDC80 kinetochore complex component | SPC24 | Yes | |
| 18 | THAP1 | THAP domain containing, apoptosis associated protein 1 | — | — | human |
| 19 | CDC123 | cell division cycle 123 | CDC123 | Yes | |
| 20 | WDR74 | WD repeat domain 74 | NSA1 | Yes | TO6E6.1[b] CG7845[d] |

Large-scale studies:
[a]*S. cerevisiae* (G. Giaever et al., Functional profiling of the *Saccharomyces cerevisiae* genome. *Nature* 418, 387-391 (2002));
[b]*C. elegans* (B. Sonnichsen et al., Full-genome RNAi profiling of early embryogenesis in *Caenorhabditis elegans. Nature* 434, 462-469 (2005));
[c]*C. elegans* (J.-F. Rual et al., Toward Improving *Caenorhabditis elegans* Phenome Mapping With an ORFeome-Based RNAi Library. *Genome Research* 14, 2162-2168 (2004));
[d]*D. melanogaster* J. L. Mummery-Widmer et al., Genome-wide analysis of Notch signalling in *Drosophila* by transgenic RNAi. *Nature* 458, 987-992 (2009));
[e]*D. melanogaster* A. C. Spradling et al., The Berkeley *Drosophila* Genome Project Gene Disruption Project: Single P-Element Insertions Mutating 25% of Vital *Drosophila* Genes. *Genetics* 153, 135-177 (1999));
[f]*D. rerio* A. Amsterdam et al., Identification of 315 genes essential for early zebrafish development. *Proceedings of the National Academy of Sciences of the United States of America* 101, 12792-12797 (2004).

To evaluate the results at a global level, Applicants tested 4722 gene sets to see if they showed strong signatures of essentiality, using Gene Set Enrichment Analysis. Gene sets related to fundamental biological processes—including DNA replication, gene transcription, and protein degradation—showed strong depletion, consistent with their essentiality (FIG. 3D, Table 2).

TABLE 2

Gene Set Enrichment Analysis. Gene composition and scores of the enriched gene sets highlighted in FIG. 3D.

| Gene | Rank in Gene List | Raw Metric | Running ES | Core |
|---|---|---|---|---|
| KEGG_DNA_REPLICATION | | | | |
| RPA4 | 1045 | 5512 | −0.12 | No |
| POLD1 | 3054 | 3944 | −0.378 | No |
| POLE4 | 3938 | 3332 | −0.474 | No |
| MCM3 | 4717 | 2712.5 | −0.556 | No |
| RFC1 | 4959 | 2497.5 | −0.561 | No |
| LIG1 | 5098 | 2369 | −0.551 | No |
| POLD4 | 5587 | 1839.5 | −0.592 | Yes |
| POLE3 | 5640 | 1778 | −0.57 | Yes |
| RPA2 | 5668 | 1751.5 | −0.544 | Yes |
| POLA1 | 5689 | 1723.5 | −0.518 | Yes |
| RNASEH2B | 6006 | 1322.5 | −0.533 | Yes |
| POLE | 6039 | 1283 | −0.509 | Yes |
| RPA3 | 6180 | 1120 | −0.499 | Yes |
| RNASEH2C | 6462 | 720.5 | −0.51 | Yes |

TABLE 2-continued

Gene Set Enrichment Analysis. Gene composition and scores of the enriched gene sets highlighted in FIG. 3D.

| Gene | Rank in Gene List | Raw Metric | Running ES | Core |
|---|---|---|---|---|
| DNA2 | 6496 | 673.5 | −0.485 | Yes |
| RFC4 | 6533 | 629.5 | −0.461 | Yes |
| MCM7 | 6542 | 615.5 | −0.433 | Yes |
| MCM2 | 6557 | 596 | −0.405 | Yes |
| RNASEH2A | 6586 | 565.5 | −0.38 | Yes |
| RFC2 | 6668 | 465 | −0.362 | Yes |
| MCM5 | 6684 | 428.5 | −0.335 | Yes |
| MCM4 | 6724 | 385.5 | −0.311 | Yes |
| POLD3 | 6766 | 342 | −0.287 | Yes |
| POLD2 | 6806 | 286.5 | −0.264 | Yes |
| MCM6 | 6808 | 286 | −0.234 | Yes |
| PRIM1 | 6817 | 275 | −0.206 | Yes |
| PRIM2 | 6845 | 247.5 | −0.18 | Yes |
| RFC5 | 6867 | 218 | −0.154 | Yes |
| POLE2 | 6904 | 175.5 | −0.13 | Yes |
| RFC3 | 6917 | 153.5 | −0.102 | Yes |
| RPA1 | 6944 | 119 | −0.076 | Yes |
| FEN1 | 6972 | 72.5 | −0.051 | Yes |
| POLA2 | 6979 | 66.5 | −0.022 | Yes |
| PCNA | 7026 | 13 | 1.00E−03 | Yes |
| KEGG_RNA_POLYMERASE | | | | |
| POLR1D | 3555 | 3610 | −0.466 | No |
| POLR2F | 3644 | 3534.5 | −0.437 | No |
| POLR3B | 3902 | 3352.5 | −0.432 | No |
| POLR3GL | 4839 | 2604.5 | −0.524 | No |
| POLR3A | 5107 | 2363 | −0.52 | No |
| POLR3D | 5251 | 2215 | −0.499 | No |
| POLR1A | 5985 | 1354.5 | −0.562 | Yes |
| POLR3F | 6247 | 1026.5 | −0.557 | Yes |
| POLR1C | 6313 | 922.5 | −0.525 | Yes |
| POLR2H | 6431 | 771 | −0.5 | Yes |
| ZNRD1 | 6694 | 412.5 | −0.496 | Yes |
| POLR3C | 6709 | 398 | −0.456 | Yes |
| POLR2B | 6744 | 368 | −0.419 | Yes |
| POLR2D | 6763 | 348 | −0.38 | Yes |
| POLR2C | 6776 | 335 | −0.34 | Yes |
| POLR1E | 6791 | 312 | −0.3 | Yes |
| POLR1B | 6844 | 249 | −0.266 | Yes |
| POLR2G | 6919 | 152.5 | −0.235 | Yes |
| POLR3K | 6948 | 108 | −0.197 | Yes |
| POLR3H | 6983 | 63.5 | −0.161 | Yes |
| POLR2E | 6998 | 47.5 | −0.121 | Yes |
| POLR2I | 7007 | 37.5 | −0.08 | Yes |
| POLR2L | 7014 | 27.5 | −0.04 | Yes |
| POLR2A | 7018 | 24.5 | 0.002 | Yes |
| KEGG_SPLICEOSOME | | | | |
| HSPA1L | 460 | 6160 | −0.057 | No |
| PRPF40B | 1234 | 5313 | −0.159 | No |
| TCERG1 | 1450 | 5129 | −0.18 | No |
| HSPA6 | 2452 | 4350.5 | −0.315 | No |
| SRSF8 | 2672 | 4196.5 | −0.337 | No |
| HSPA2 | 3066 | 3934.5 | −0.384 | No |
| TRA2A | 3276 | 3781.5 | −0.404 | No |
| SRSF4 | 3524 | 3624 | −0.43 | No |
| PQBP1 | 3603 | 3564 | −0.432 | No |
| U2SURP | 3746 | 3466 | −0.442 | No |
| PPIL1 | 4504 | 2883.5 | −0.542 | No |
| DDX5 | 4508 | 2881 | −0.533 | No |
| WBP11 | 4689 | 2731.5 | −0.549 | No |
| SNRPB2 | 4710 | 2718 | −0.542 | No |
| DHX16 | 4751 | 2683 | −0.538 | No |
| DDX42 | 4956 | 2499 | −0.558 | No |
| SNRNP40 | 5269 | 2200 | −0.593 | No |
| DDX46 | 5457 | 1988.5 | −0.61 | Yes |
| PPIE | 5472 | 1974.5 | −0.603 | Yes |
| PRPF31 | 5486 | 1958 | −0.595 | Yes |
| SRSF5 | 5499 | 1941.5 | −0.587 | Yes |
| LSM5 | 5615 | 1812 | −0.594 | Yes |
| U2AF1 | 5617 | 1810.5 | −0.584 | Yes |
| HNRNPA1 | 5676 | 1736 | −0.583 | Yes |
| USP39 | 5738 | 1674 | −0.582 | Yes |
| PRPF4 | 5788 | 1616.5 | −0.579 | Yes |
| DHX8 | 5893 | 1466.5 | −0.585 | Yes |
| LSM2 | 5958 | 1387 | −0.584 | Yes |
| AQR | 5982 | 1355.5 | −0.578 | Yes |
| PLRG1 | 6062 | 1261 | −0.58 | Yes |
| U2AF2 | 6076 | 1250.5 | −0.572 | Yes |
| CCDC12 | 6110 | 1221 | −0.567 | Yes |
| THOC1 | 6112 | 1219 | −0.557 | Yes |
| DDX23 | 6147 | 1159 | −0.552 | Yes |
| CRNKL1 | 6183 | 1116 | −0.548 | Yes |
| LSM4 | 6186 | 1114.5 | −0.538 | Yes |
| ISY1 | 6204 | 1092 | −0.531 | Yes |
| RBMX | 6210 | 1084.5 | −0.522 | Yes |
| CWC15 | 6252 | 1015 | −0.518 | Yes |
| SRSF9 | 6270 | 984.5 | −0.511 | Yes |
| RBM8A | 6291 | 956 | −0.504 | Yes |
| SNRNP70 | 6321 | 915.5 | −0.499 | Yes |
| SNRNP27 | 6324 | 912.5 | −0.489 | Yes |
| SRSF10 | 6325 | 912 | −0.48 | Yes |
| SLU7 | 6337 | 894.5 | −0.471 | Yes |
| DHX38 | 6338 | 894 | −0.462 | Yes |
| SF3A1 | 6343 | 889 | −0.453 | Yes |
| XAB2 | 6371 | 856.5 | −0.447 | Yes |
| SNW1 | 6373 | 854 | −0.437 | Yes |
| SNRPD3 | 6395 | 829 | −0.431 | Yes |
| RBM17 | 6402 | 819.5 | −0.422 | Yes |
| CDC40 | 6406 | 814 | −0.412 | Yes |
| PRPF3 | 6442 | 746.5 | −0.408 | Yes |
| NHP2L1 | 6463 | 718 | −0.401 | Yes |
| THOC2 | 6469 | 709 | −0.392 | Yes |
| RBM25 | 6473 | 707.5 | −0.383 | Yes |
| HNRNPU | 6478 | 698 | −0.374 | Yes |
| PRPF8 | 6486 | 685.5 | −0.365 | Yes |
| NAA38 | 6492 | 677.5 | −0.356 | Yes |
| SNRPA | 6495 | 673.5 | −0.346 | Yes |
| SYF2 | 6514 | 654.5 | −0.339 | Yes |
| HNRNPM | 6518 | 648.5 | −0.33 | Yes |
| BCAS2 | 6534 | 629 | −0.323 | Yes |
| EFTUD2 | 6569 | 578.5 | −0.318 | Yes |
| PRPF18 | 6605 | 544 | −0.313 | Yes |
| SMNDC1 | 6609 | 538.5 | −0.304 | Yes |
| PRPF38A | 6641 | 499 | −0.299 | Yes |
| SF3B5 | 6643 | 494.5 | −0.289 | Yes |
| PRPF38B | 6655 | 480.5 | −0.281 | Yes |
| SNRPB | 6657 | 479.5 | −0.271 | Yes |
| ACIN1 | 6664 | 468.5 | −0.262 | Yes |
| DHX15 | 6686 | 426.5 | −0.256 | Yes |
| SNRPC | 6727 | 383 | −0.252 | Yes |
| CTNNBL1 | 6739 | 375 | −0.244 | Yes |
| TRA2B | 6741 | 373.5 | −0.234 | Yes |
| ZMAT2 | 6742 | 370 | −0.224 | Yes |
| SNRPD2 | 6771 | 339.5 | −0.219 | Yes |
| LSM7 | 6772 | 339.5 | −0.209 | Yes |
| PUF60 | 6783 | 325 | −0.201 | Yes |
| CDC5L | 6801 | 297 | −0.194 | Yes |
| SART1 | 6805 | 291 | −0.184 | Yes |
| SRSF6 | 6807 | 286 | −0.175 | Yes |
| NCBP1 | 6826 | 264.5 | −0.168 | Yes |
| SNRPA1 | 6827 | 264.5 | −0.158 | Yes |
| SF3B2 | 6831 | 261 | −0.149 | Yes |
| SRSF7 | 6841 | 250.5 | −0.14 | Yes |
| DDX39B | 6852 | 241 | −0.132 | Yes |
| RBM22 | 6859 | 230.5 | −0.123 | Yes |
| PRPF19 | 6864 | 224.5 | −0.114 | Yes |
| HNRNPK | 6894 | 189 | −0.108 | Yes |
| SF3A2 | 6912 | 167.5 | −0.101 | Yes |
| BUD31 | 6923 | 149.5 | −0.093 | Yes |
| PRPF6 | 6927 | 147 | −0.084 | Yes |
| PCBP1 | 6928 | 142.5 | −0.074 | Yes |
| EIF4A3 | 6939 | 129 | −0.066 | Yes |
| NCBP2 | 6942 | 121.5 | −0.056 | Yes |
| SNRNP200 | 6951 | 101.5 | −0.048 | Yes |
| TXNL4A | 6963 | 88.5 | −0.04 | Yes |
| SRSF3 | 6975 | 69.5 | −0.031 | Yes |
| SRSF2 | 6989 | 54.5 | −0.024 | Yes |

TABLE 2-continued

Gene Set Enrichment Analysis. Gene composition and scores of the enriched gene sets highlighted in FIG. 3D.

| Gene | Rank in Gene List | Raw Metric | Running ES | Core |
|---|---|---|---|---|
| SRSF1 | 7002 | 44 | −0.016 | Yes |
| SF3A3 | 7020 | 23.5 | −0.008 | Yes |
| SF3B3 | 7030 | 8 | 0.00E+00 | Yes |
| BIOCARTA_PROTEASOME_PATHWAY | | | | |
| UBE2A | 319 | 6328.5 | −0.007 | No |
| UBE3A | 2034 | 4674.5 | −0.213 | No |
| PSMD8 | 2876 | 4054.5 | −0.295 | No |
| PSMA4 | 5599 | 1831 | −0.645 | Yes |
| PSMC4 | 5706 | 1708.5 | −0.622 | Yes |
| PSMB6 | 5800 | 1603 | −0.596 | Yes |
| PSMD12 | 6056 | 1267 | −0.594 | Yes |
| PSMA3 | 6094 | 1233 | −0.561 | Yes |
| RPN2 | 6161 | 1148 | −0.532 | Yes |
| PSMB4 | 6202 | 1096 | −0.499 | Yes |
| PSMD14 | 6366 | 862 | −0.484 | Yes |
| PSMB3 | 6394 | 829 | −0.45 | Yes |
| PSMC2 | 6438 | 753 | −0.417 | Yes |
| PSMB1 | 6516 | 652.5 | −0.39 | Yes |
| PSMB5 | 6649 | 487.5 | −0.37 | Yes |
| PSMA2 | 6674 | 451.5 | −0.335 | Yes |
| P SMA1 | 6716 | 392.5 | −0.303 | Yes |
| PSMB2 | 6762 | 348 | −0.271 | Yes |
| PSMA5 | 6768 | 341.5 | −0.233 | Yes |
| PSMD6 | 6795 | 306.5 | −0.198 | Yes |
| PSMB7 | 6813 | 281.5 | −0.162 | Yes |
| PSMC6 | 6834 | 258 | −0.126 | Yes |
| PSMA6 | 6855 | 238 | −0.091 | Yes |
| PSMC3 | 6916 | 155 | −0.061 | Yes |
| PSMD11 | 6934 | 133.5 | −0.025 | Yes |
| PSMA7 | 7027 | 13 | 0.00E+00 | Yes |

TABLE 3

Analysis of features influencing sgRNA potency. Summary of the variance in ribosomal protein-targeting sgRNA log2 fold changes explained by various features of sgRNAs using a general linear model.

| Variable | Degrees of Freedom | Variance Explained ($r^2$) |
|---|---|---|
| Full Sequence (combined) | 2460 | 1 |
| First 4 nucleotides (combined) | 250 | 0.17 |
| Middle 4 nucleotides (combined) | 251 | 0.133 |
| Last 4 nucleotides (combined) | 251 | 0.291 |
| First 4 nucleotides (additive) | 12 | 0.04 |
| Middle 4 nucleotides (additive) | 12 | 0.02 |
| Last 4 nucleotides (additive) | 12 | 0.129 |
| GC Content | 14 | 0.025 |
| gRNA Strand | 1 | 0.014 |
| Exon Type | 2 | 0.013 |

Applicants hypothesized that differences in sgRNA potency might also result from sequence features governing interactions with Cas9. To test this, Applicants developed a method to profile the sgRNAs directly bound to Cas9 in a highly parallel manner. By comparing the abundance of sgRNAs bound to Cas9 relative to the abundance of their corresponding genomic integrants, Applicants found that the nucleotide composition near the 3'-end of the spacer sequence was the most important determinant of Cas9 loading (FIG. 3F). Specifically, Cas9 preferentially bound sgRNAs containing purines in the last 4 nucleotides of the spacer sequence whereas pyrimidines were disfavored. A similar pattern emerged when Applicants examined depletion of ribosomal protein-targeting sgRNAs (r=0.81), suggesting that, in significant part, the cleavage efficiency of a sgRNA was determined by its affinity for Cas9 (Table 3).

Applicants then sought to build an algorithm to discriminate between potent and weak sgRNAs (FIG. 3G). Applicants trained a support-vector-machine classifier based on the target sequences and depletion scores of ribosomal protein-targeting single guide RNAs. As an independent test, Applicants used the classifier to predict the efficacy of sgRNAs targeting the 400 top scoring (i.e. essential) non-ribosomal genes. The top two-thirds of Applicants' predictions exhibited 3-fold higher potency than the remaining fraction, confirming the accuracy of the algorithm.

Using this algorithm, Applicants designed a whole-genome sgRNA library consisting of sequences predicted to have higher efficacy (see Genetic screens in human cells using the CRISPR-Cas9 system. Wang T, Wei J J, Sabatini D M, Lander E S. Science. 2014 Jan. 3; 343(6166):80-4. doi: 10.1126/science.1246981. Epub 2013 Dec. 12 and supplemental material, the respective content of which is incorporated herein by reference, providing Annotations for the predicted genome-wide sgRNA library containing spacer sequences and target gene information; see also herein-cited US and PCT patent applications and ATCC Deposits concerning the GeCKO Library(ies)). As with the sgRNA pool used in Applicants' screens, this new collection was also filtered for potential off-target matches. This reference set of sgRNAs may be useful both for targeting single genes as well as large-scale sgRNA screening.

Taken together, these results demonstrated the utility of CRISPR-Cas9 for conducting large-scale genetic screens in mammalian cells. Based on Applicants' experiments, this system appears to offer several powerful features that together provide significant advantages over current functional screening methods.

Figure 7:
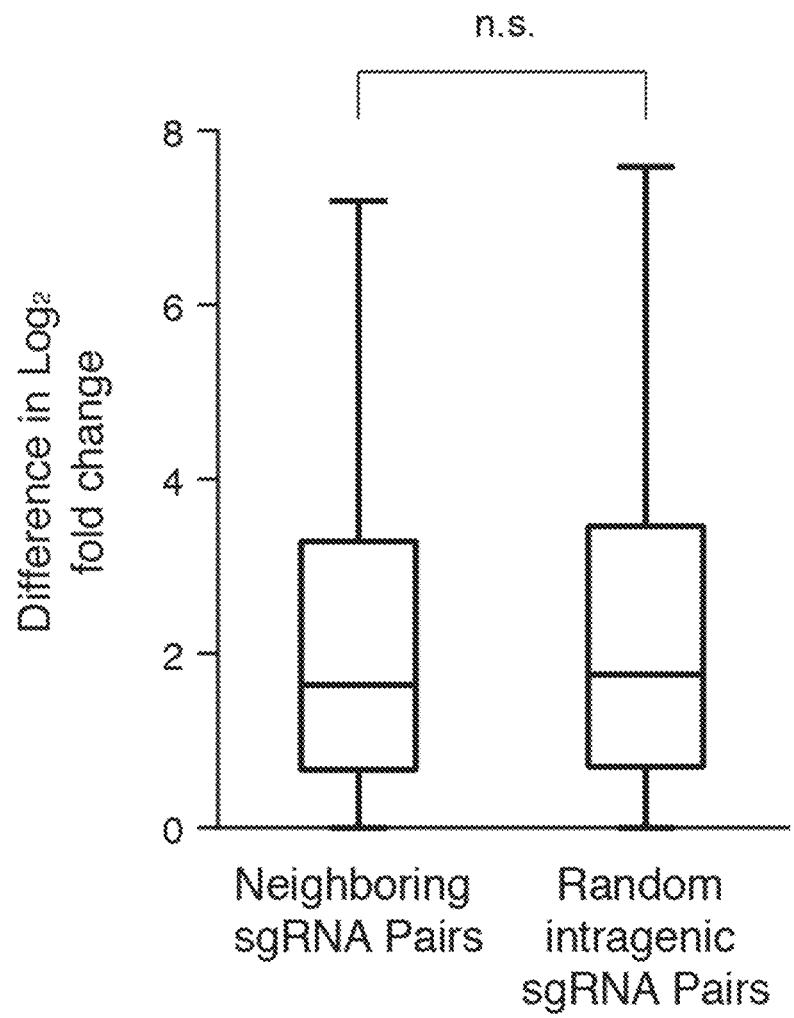
FIG. 7 shows High variability is observed between neighboring ribosomal protein gene-targeting sgRNAs. Differences in log 2 fold change of neighboring sgRNA pairs are similar to differences in log 2 fold change of random sgRNA pairs within the same gene indicating that local chromatin state does not significantly impact sgRNA efficacy.
Figure 9A:
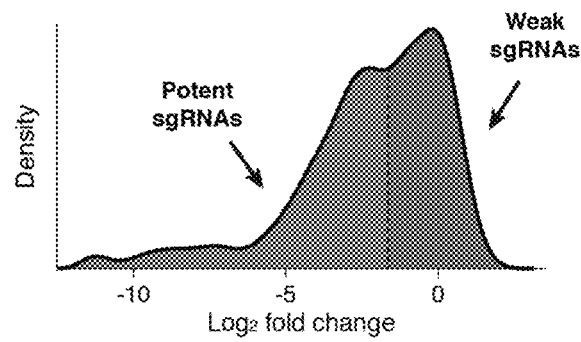
FIGS. 9A-B show a scheme for predicting weak and potent sgRNAs (A) A graphical representation of the density vs. $Log_2$ fold change of ribosomal protein-targeting sgRNAs. (B) Chart showing a representation of a machine learning algorithm (a support vector machine (SVM)) that predicts the efficacy of a sgRNA based solely on the primary sequence of the sgRNA, wherein the algorithm is trained using data from ribosomal training sgRNAs.
Figure 9B:
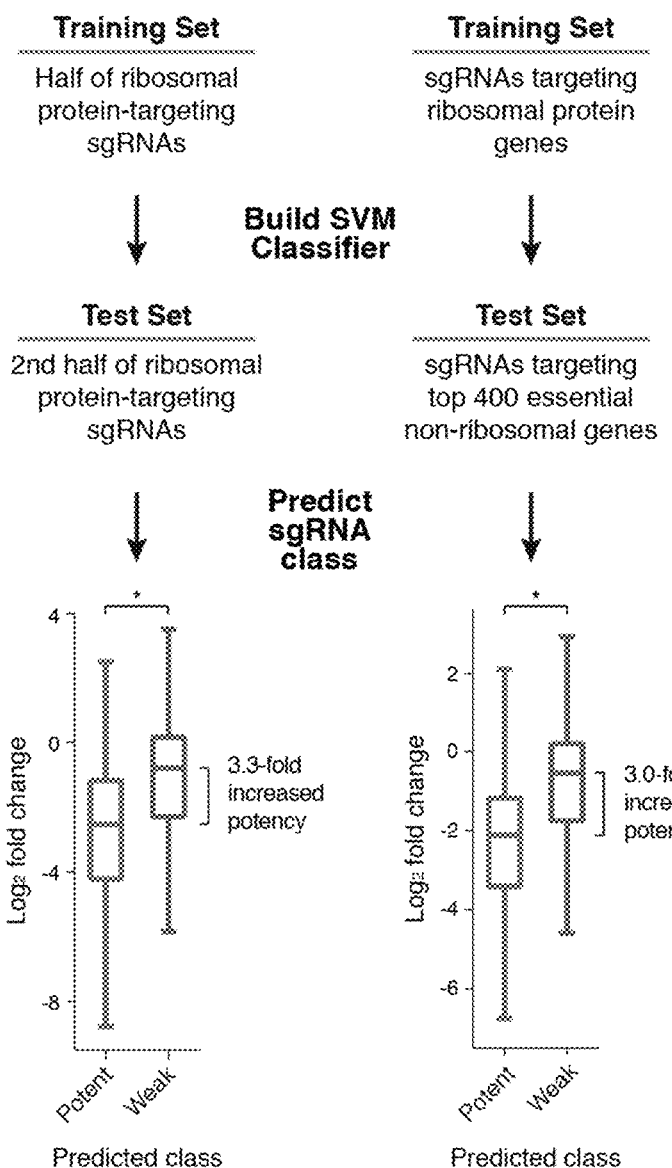

First, CRISPR/Cas9 inactivates genes at the DNA level, making it possible to study phenotypes that require a com- Example 2: Features Underlying sgRNA Potency Applicants sought to understand the features underlying sgRNA potency. Although the vast majority of sgRNAs against ribosomal protein genes showed depletion, detailed comparison of sgRNAs targeting the same gene revealed substantial variation in the precise amounts of depletion. These differences are unlikely to be caused by local accessibility to the Cas9/sgRNA complex inasmuch as comparable variability was observed even among sgRNAs targeting neighboring target sites of a given gene (FIG. 7). Given that Applicants' library includes all possible sgRNAs against each of the 84 ribosomal genes, the data allowed Applicants to search for factors that might explain the differential efficacy of sgRNAs. Because the majority of ribosomal proteins genes are essential, Applicants reasoned that the level of depletion of a given ribosomal protein-targeting sgRNA could serve as a proxy for its cleavage efficiency. Applying this approach, Applicants found several trends related to sgRNA efficacy: (1) Single guide sequences with very high or low GC content were less effective against their targets. (2) sgRNAs targeting the last coding exon were less effective than those targeting earlier exons, consistent with the notion that disruption of the terminal exon would be expected to have less impact on gene function. (3) sgRNAs targeting the transcribed strand were less effective than those targeting the non-transcribed strand (FIG. 3E). Although these trends were statistically significant, they explained only a small proportion of differences in sgRNA potency (Table 3).

plete loss of gene function to be elicited. In addition, the system should also enable functional interrogation of non-transcribed elements, which are inaccessible by RNAi.

Second, a large proportion of sgRNAs successfully generate mutations at their target sites. While this parameter is difficult to directly assess in pooled screens, Applicants obtained an estimate by examining the 'hit rate' at known genes. Applying a z-score analysis of Applicants' positive selection screens, Applicants found that over 75% (46/60) of sgRNAs score at a significance threshold that perfectly separates true and false positives on a gene level (FIG. 8A-D). Together these results show that the effective coverage of Applicants' library is very high and that the rate of false negatives should be low even in a large-scale screen.

Third, off-target effects do not appear to seriously hamper Applicants' screens, based on several lines of evidence. Direct sequencing of potential off-target loci detected minimal cleavage at secondary sites, which typically reside in non-coding regions and do not impact gene function. Moreover, in the 6-TG screens, the twenty most abundant sgRNAs all targeted one of the four members of the MMR pathway. In total, they represented over 30% of the final pool, a fraction greater the next 400 sgRNAs combined. In the etoposide screen, the two top genes scored far above background levels (p-values 100-fold smaller than the next best gene), enabling clear discrimination between true and false positive hits. Lastly, new versions of the CRISPR-Cas9 system have recently been developed that substantially decrease off-target activity.

Example 3: Confirmation of Approach

Although Applicants investigations relate to proliferation-based phenotypes, Applicants' approach can be applied to a much wider range of biological phenomena. With appropriate sgRNA libraries, the method should enable genetic analyses of mammalian cells to be conducted with a degree of rigor and completeness currently possible only in the study of microorganisms.

Methods and Materials

Cell lines and vectors: Materials were obtained from the following sources: HL-60 were kindly provided from the Whitehead Institute, Cambridge, Mass., USA; pCW57.1 Dox-inducible lentiviral vector, pX330-U6-Chimeric_BB-CBh-hSpCas9 vector, pLX304 lentiviral vector, and gRNA_AAVS1-T2 vector from Addgene.

Cell culture: Unless otherwise specified, 293T cells were cultured in DMEM (US Biological) and supplemented with 20% Inactivated Fetal Calf Serum (Sigma), 5 mM glutamine, and penicillin/streptomycin. HL60 and KBM7 cells were cultured in IMDM (Life Technologies) and supplemented with 20% IFS, 5 mM glutamine and penicilin/streptomycin.

Viability assay: Cells were seeded in 96-well tissue culture plates at 4000 cells/well in 200 µL of media under various treatment conditions. After 3 days, 35 µL of Cell-Titer-Glo reagent (Promega) was added to each well, mixed for 5 minutes, and the luminescence was read on the SpectraMax M5 Luminometer (Molecular Devices). All experiments were performed in triplicate.

Dosing of screening agents: To determine the appropriate dose of 6-TG and etoposide for screening in KBM7 and HL60 cells, cells were seeded in 96-well tissue culture plates at 4000 cells/well in 200 µL of media and were treated in triplicate with varying concentrations of 6-TG and etoposide. A CellTiter-Glo cell viability assay was performed after 4 days to assess drug toxicity. Concentrations at which the viability of WT KBM7 and HL60 cells fell below 5% were chosen.

Vector construction: To construct the lentiviral doxycycline-inducible FLAG-Cas9 vector, the FLAG-Cas9 ORF from pX330-U6-Chimeric_BB-CBh-hSpCas9 was cloned into pCW57.1 between the AgeI and EcoRI sites. To construct the lentiviral sgRNA vector, the U6 promoter, the AAVS1-targeting sequence (GGGGCCACTAGGGACAG-GAT) (SEQ ID NO: 19), and the chimeric sgRNA scaffold from gRNA_AAVS1-T2 was cloned into pLX304 between the XhoI and NheI sites.

Genome-scale lentiviral sgRNA library design: All SpCas9 Protospacer Adjacent Motif (PAM) sites within 5 bases of a coding exon for all RefSeq transcript models were identified. If the first nucleotide of the protospacer/guide sequence did not begin with a 'G' (as is required for RNA polymerase III-dependent transcription), a 'G' was prepended. The sequences were then filtered for homopolymers spanning greater than 3 nucleotides. To avoid potential off-target cleavage, guide sequences that perfectly matched or had only 1 mismatch within the first 12 bases (the 'non-seed' region) with another genomic region were identified using the short read aligner Bowtie and excluded. This specificity search was not performed for sgRNAs targeting ribosomal proteins. Subsequently, guide sequences that contained XbaI or NdeI sites were removed (although the library was eventually cloned via Gibson assembly) and guide sequences were filtered such that no two sgRNAs overlapped by more than 15 base pairs. After this step, all candidate sgRNAs for ribosomal protein genes were included in Applicants' final set. Additional candidate genes for screening were selected based upon their putative biological functions. Genes were excluded if they were not expressed (FPKM<1 in all tissues transcriptionally profiled in the Illumina Human Body Map and ENCODE project) or if 10 sgRNA sequences could not be designed. Finally for all remaining genes, 10 candidate sgRNAs were selected with a preference for sequences that (1) targeted constitutive exons, (2) were positioned closest downstream of the start codon and (3) had between 20% and 80% GC content. Sequences for non-targeting control sgRNAs were randomly generated and a specificity check, as described above, was performed. A second mini-library containing sgRNAs targeting ribosomal protein genes (2741 sgRNAs), BCR (228 sgRNAs), ABL1 (223 sgRNAs) and 600 non-targeting control sgRNAs was designed as described above and used for negative selection screening and Cas9 immunoprecipitation/sgRNA sequencing in KBM7 cells.

Design of predicted genome-wide library: All SpCas9 Protospacer Adjacent Motif (PAM) sites within 6 bases of a coding exon for all CCDS transcript models were identified. If the first nucleotide of the protospacer/guide sequence did not begin with a 'G' (as is required for RNA polymerase III-dependent transcription), a 'G' was prepended. Sequences with % GC content between 40 to 80% that did not contain any homopolymers spanning greater than 4 nucleotides were considered. Because off-target matches may be unavoidable in some cases (eg. pseudogenes and duplicated genes), sequences were removed only if they mapped to more than 5 regions in the genome. Additionally for uniquely mapped sgRNAs, Applicants then found the number off-target matches that differ from the guide sequence by only one base pair in the first twelve nucleotides (the 'non-seed' region). Olfactory receptor genes and genes with less than 5 sgRNA sequences fulfilling the criteria outlined above were excluded. For all remaining genes, 5-10 candidate sgRNAs were selected with a preference for sequences ordered by (1) the number of matches elsewhere in the genome (2) the number of 1-bp mismatched guide sequences that map elsewhere in the genome (3) the number of transcript models targeted for a given gene (4) the sgRNA score as predicted by the sgRNA potency algorithm and (5) the position along the transcript. Guide sequences were first filtered such that no two sgRNAs overlapped by more than 10 base pairs but this condition was relaxed to allow a 15 base pair overlap if no satisfactory sgRNAs could be found. Sequences for non-targeting control sgRNAs were randomly generated and a specificity check, as described above, was performed.

Genome-scale lentiviral sgRNA library construction: Oligonucleotides were synthesized on the CustomArray 12K and 90K arrays (CustomArray Inc.) and amplified as sub-pools in a nested PCR. A third round of PCR was performed to incorporate overhangs compatible for Gibson Assembly (NEB) into the lentiviral sgRNA AAVS1-targeting vector between the XbaI and NdeI sites. Gibson Assembly reaction products were transformed into chemically competent DH5alpha cells. To preserve the diversity of the library, at least 20-fold coverage of each pool was recovered in each transformation and grown in liquid culture for 16-18 hours.

Virus production and transduction: Lentivirus was produced by the co-transfection of the lentiviral transfer vector with the Delta-VPR envelope and CMV VSV-G packaging plasmids into 293T cells using XTremeGene 9 transfection reagent (Roche). Media was changed 24 hours after transfection. The virus-containing supernatant was collected 48 and 72 hours after transfection and passed through a 0.45 μm filter to eliminate cells. Target cells in 6-well tissue culture plates were infected in media containing 8 μg/mL of polybrene and spin infection was performed by centrifugation at 2,200 rpm for 1 hour. 24 hours after infection, virus was removed and cells were selected with the appropriate antibiotics.

Cas9-KBM7 and Cas9-HL60 generation: Cas9-KBM7 and Cas9-HL60 cells were generated by lentiviral transduction of the dox-inducible FLAG-Cas9 vector. After 3 days of selection with puromycin, the cells were clonally sorted using an Aria II SORP (BD FACS) into 96-well tissue culture plates containing 200 μL of media. The level of FLAG-Cas9 expression in the presence and absence of 1 μg/mL doxycycline was analyzed for several clonal populations by western blotting. Subsequently, a single colony with the greatest fold-change in Cas9 expression was selected from both cell lines for further studies.

Assessment of CRISPR/Cas9 cleavage efficiency: Cas9-KBM7 cells were infected with a sgRNA construct targeting the AASV1 locus at low MOI. At 0, 1, 2, 4, and 6 days post infection, cells were harvested for genomic DNA extraction. After amplification of the AAVS1 locus (primers sequences listed below), the SURVEYOR nuclease assay (Transgenomics) and gel quantification was performed. For deep sequencing of the target region, the AAVS1 locus was amplified with primers containing overhangs with adapters compatible with Illumina sequencing. Amplicons were sequenced on a MiSeq (Illumina) with a single-end 50 bp run. The resulting reads were aligned to the target reference sequence using the Smith-Waterman algorithm. Mutations were classified as a deletion, insertion, substitution or complex (a mixture of the previous 3 classes). Complex mutations were excluded in downstream analyses.

PCR primer sequences for Surveyor Assay
Primer 1:
(SEQ ID NO: 20)
CCCCGTTCTCCTGTGGATTC Primer 2:
(SEQ ID NO: 21)
ATCCTCTCTGGCTCCATCGT Primer sequences for MiSeq Sequencing Assay
Primer 1:
(SEQ ID NO: 22)
AATGATACGGCGACCACCGAGATCTACACCCCGTTCTCCTGTGGATTC Primer 2:
(SEQ ID NO: 23)
CAAGCAGAAGACGGCATACGAGATCATCCTCTCTGGCTCCATCGT Illumina sequencing primer:
(SEQ ID NO: 24)
TCTGGTTCTGGGTACTTTTATCTGTCCCCTCCACCCCACAGT Analysis of CRISPR/Cas9 specificity: Cas9-KBM7 cells were infected with a sgRNA construct targeting the AASV1 locus (sgAAVS). Cells were selected for two weeks with blasticidin and harvested for genomic DNA extraction. Potential off-target cleavage sites were predicted by searching for genomic regions with sequence similarity to sgAAVS1 (no more than 3 mismatches were tolerated). Nested PCR primers were designed around these regions and the AAVS1 target region and used to amplify genomic DNA from sgAAVS1-modified and unmodified wild-type cells. PCR amplicons were sequenced on a MiSeq (Illumina) with a single-end 300 bp run. The resulting reads were filtered for the presence of matching forward and reverse primers and primer-dimer products were removed. Using the Needleman-Wunsch algorithm, amplicon reads were aligned to their respective reference sequences and assessed for the presence of an insertion or deletion.

Pooled screening: In all screens, 90 million target cells were transduced with viral sub pools and selected with blasticidin 24 hours after infection for 3 days. For the 6-TG screen, Cas9-KBM7 cells were cultured in media containing 400 nM 6-TG. For screens with etoposide, Cas9-KBM7 and Cas9-HL60 cells were cultured in media containing 130 nM and 200 nM of etoposide, respectively. Cultures of untreated Cas9-KBM7 and Cas9-HL60 cells were also maintained in parallel. All cells were passaged every 3 days, and after 12 days, cells were harvested for genomic DNA extraction. In negative selection screens, 10 million cells were harvested for genomic DNA extraction 24 hours after infection. The remaining cells were maintained for 12 doublings, before being harvested for genomic DNA extraction.

Pooled screening deconvolution and analysis: In both the positive and negative selection screens, sgRNA inserts were PCR amplified in a nested PCR and the resulting libraries were sequenced on a HiSeq 2500 (Illumina) with a single-end 50 bp run. The primer sequences for these reactions are provided below. Sequencing reads were aligned to the sgRNA library, and the abundance of each sgRNA was calculated. For the etoposide screens, the sgRNA abundances between the final treated and untreated populations were compared. To identify genes whose loss conferred resistance to etoposide, the (treated-untreated) log 2 abundances of all sgRNAs targeting a gene was compared with the non-targeting sgRNAs using a one-sided Kolmogorov-Smirnov (K-S) test. p-values were corrected using the Benjamini-Hochberg method. To perform a sgRNA-level z-score analysis for all positive selection screens, the mean and standard deviation of the differential abundances of the non-targeting sgRNAs between treated versus untreated pools was determined. From these values, a z-score was calculated for all other sgRNAs.

In the negative selection screen, the log 2 fold change in abundance of each sgRNA between the initial and final populations was computed. The significance of a gene hit was assessed by a two-sided K-S test between the log 2 fold change of all sgRNAs targeting a gene and the values for all targeting sgRNAs. For ribosomal protein genes for which more sgRNAs were designed, random subsets of 10 sgRNAs were sampled for significance testing and the p-value assigned to the gene was the median value after 50 random samplings. p-values were corrected using the Benjamini-Hochberg method. Gene-based scores were defined as the median log 2 fold change of all sgRNAs targeting a given gene. For all genes, scores were calculated for both the HL60 and KBM7 screens. The two gene lists were sorted and the combined rank was determined. This metric was used for the Gene Set Enrichment Analysis of the C2 curated genes sets.

```
Primer sequences for sgRNA quantification
Outer primer 1:
                                         (SEQ ID NO: 25)
AGCGCTAGCTAATGCCAACTT Outer primer 2:
                                         (SEQ ID NO: 26)
GCCGGCTCGAGTGTACAAAA Inner primer 1:
                                         (SEQ ID NO: 27)
AATGATACGGCGACCACCGAGATCTACACCGACTCGGTGCCACTTTT Inner primer 2:
                                         (SEQ ID NO: 28)
CAAGCAGAAGACGGCATACGAGATCnnnnnTTTCTTGGGTAGTTTGCAGT
TTT (nnnnn denotes the sample barcode)

Illumina sequencing primer:
                                         (SEQ ID NO: 29)
CGGTGCCACTTTTTCAAGTTGATAACGGACTAGCCTTATTTTAACTTGCT
ATTTCTAGCTCTAAAAC Illumina indexing primer:
                                         (SEQ ID NO: 30)
TTTCAAGTTACGGTAAGCATATGATAGTCCATTTTAAAACATAATTTTAA
AACTGCAAACTACCCAAGAAA
```

Generation of sgRNA modified cell lines: Individual sgRNA constructs targeting CDK6 and TOP2A were cloned, lentivirus was produced, and target HL60 cells were transduced as described above. 24 hours after infection cells were cultured in doxycycline and blasticidin for 1 week before further experimentation.

Western blotting: Cells were lysed directly in Laemmli sample buffer, separated on a NuPAGE Novex 8% Tris-Glycine gel, and transferred to a polyvinylidene difluoride membrane (Millipore). Immunoblots were processed according to standard procedures, using primary antibodies directed to S6K1 (CST), CDK6 (CST), FLAG (Sigma), and TOP2A (Topogen) and analyzed using enhanced chemiluminescence with HRP-conjugated anti-mouse and anti-rabbit secondary antibodies (Santa Cruz Biotechnology).

FLAG-Cas9 immunoprecipitation and sgRNA-sequencing: 10 million Cas9-KBM7 cells were transduced with lentivirus from the sgRNA mini-pool as described above. 24 hours after transduction, cells were rinsed once with ice-cold PBS and lysed in RIPA buffer (0.1% SDS, 1% sodium deoxycholate, 1% NP-40, 25 mM Tris-HCl pH 7.6, 150 mM NaCl, 1 mM EDTA, one tablet of EDTA-free protease inhibitor (per 25 ml) and 200U Murine RNAse Inhibitor (Sigma)). Cell lysate was homogenized using a 28-gauge syringe needle and incubated with rotation at 4° C. for 15 minutes. The soluble fractions of cell lysates were isolated by centrifugation at 13,000 rpm in a refrigerated microcentrifuge for 10 min. The FLAG-M2 affinity gel (Sigma-Aldrich) was washed with lysis buffer three times, and 100 μl of a 50% slurry of the affinity gel was then added to cleared cell lysates and incubated with rotation for 3 hours at 4C. The beads were washed eight times with lysis buffer. Bound proteins were specifically eluted from the FLAG-M2 affinity gel with a competing FLAG peptide by incubation at room temperature for 10 minutes. The eluate was cleaned using a RNA Clean & Concentrator-5 column (Zymo Research), treated with TURBO DNase at 37° C. for 10 minutes, and dephosphorylated with FastAP Thermosensitive Alkaline Phosphatase (Thermo Scientific) at 37° C. for 10 minutes. The reaction was stopped by the addition of EDTA at a final concentration of 25 mM and heated at 68° C. for 2 minutes after which the reaction was again cleaned using a RNA Clean & Concentrator-5 column. A sgRNA-specific reverse transcription reaction was performed using the primer listed below with SuperScript III (Life Technologies) at 54° C. for 1 hour. The remainder of the library preparation protocol was performed as previously described except that a sgRNA-specific reverse primer was used for library amplification. In parallel, sgRNA barcode integrations in the DNA were also sequenced as described above. Sequencing reads from both libraries were aligned to the sgRNA library and the ratio of RNA reads to DNA reads for each sgRNA was used as a measure of Cas9 affinity.

```
Primer sequences for sgRNA-sequencing library
preparation
sgRNA-specific reverse transcription primer:
                                         (SEQ ID NO: 31)
CTCGGTGCCACTTTTTCA sgRNA-specific library amplification primer:
                                         (SEQ ID NO: 32)
CAAGCAGAAGACGGCATACGAGATCTTCAAGTTGATAACGGACTAGCC
``` sgRNA potency analysis: Log fold change (depletion) values for sgRNAs targeting ribosomal protein genes were used as a proxy for sgRNA potency. Depletion values were analyzed with respect to guide sequence GC content, the target exon position and the strand targeted. The predictive power of the features uncovered was examined by using a general linear model. sgRNAs against inessential ribosomal genes (RPS4Y2, RP4Y1, RPL22L1, RPL3L, RPL10L, RPL26L1, RPL39L, RPS27L) were omitted from this analysis.

sgRNA potency prediction: A support-vector-machine classifier was used to predict sgRNA potency. The target sequences (each encoded by a vector of 80 binary variables representing the presence or absence of each nucleotide (A, C, T, G) at each position (1-20) along the target sequence) of ribosomal protein gene-targeting sgRNAs were used as inputs to the classifier which was trained on the change in abundance observed (encoded by a binary variable corresponding to 'weak' and 'potent' sgRNAs using a cutoff based on the bimodality of the distribution). Target sequences of sgRNAs targeting the 400 most essential non-ribosomal genes from the Cas9-KBM7 screens were used to predict potency. Class membership was again determined based on the bimodality of the distribution. sgRNAs against inessential ribosomal genes (RPS4Y2, RPS4Y, RPL22L1, RPL3L, RPL10L, RPL26L1, RPL39L, RPS27L) were omitted from this analysis.

Figure 10:
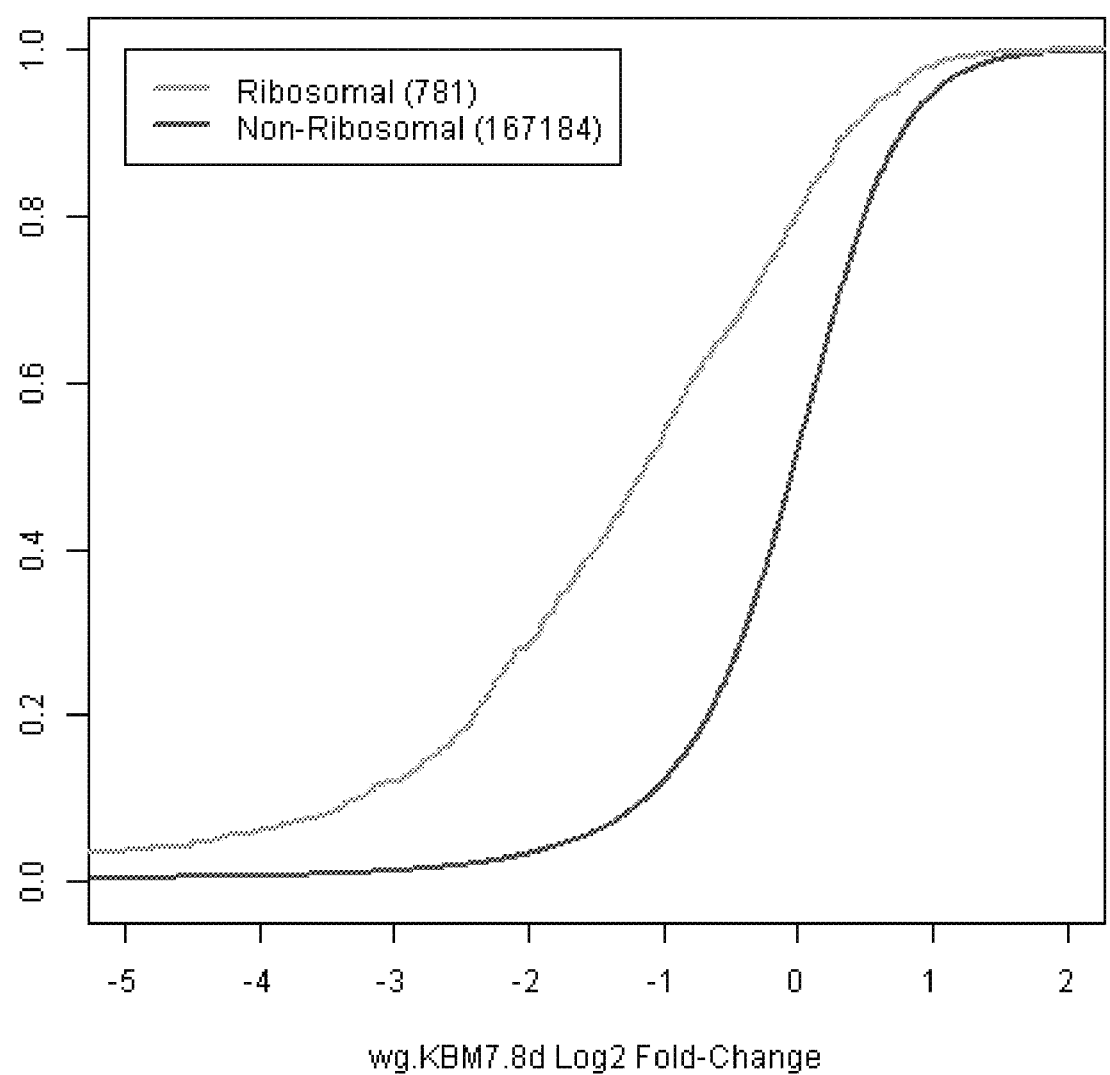
FIG. 10 is a graph showing classic depletion of sgRNAs targeting ribosomal proteins.
Figure 11:
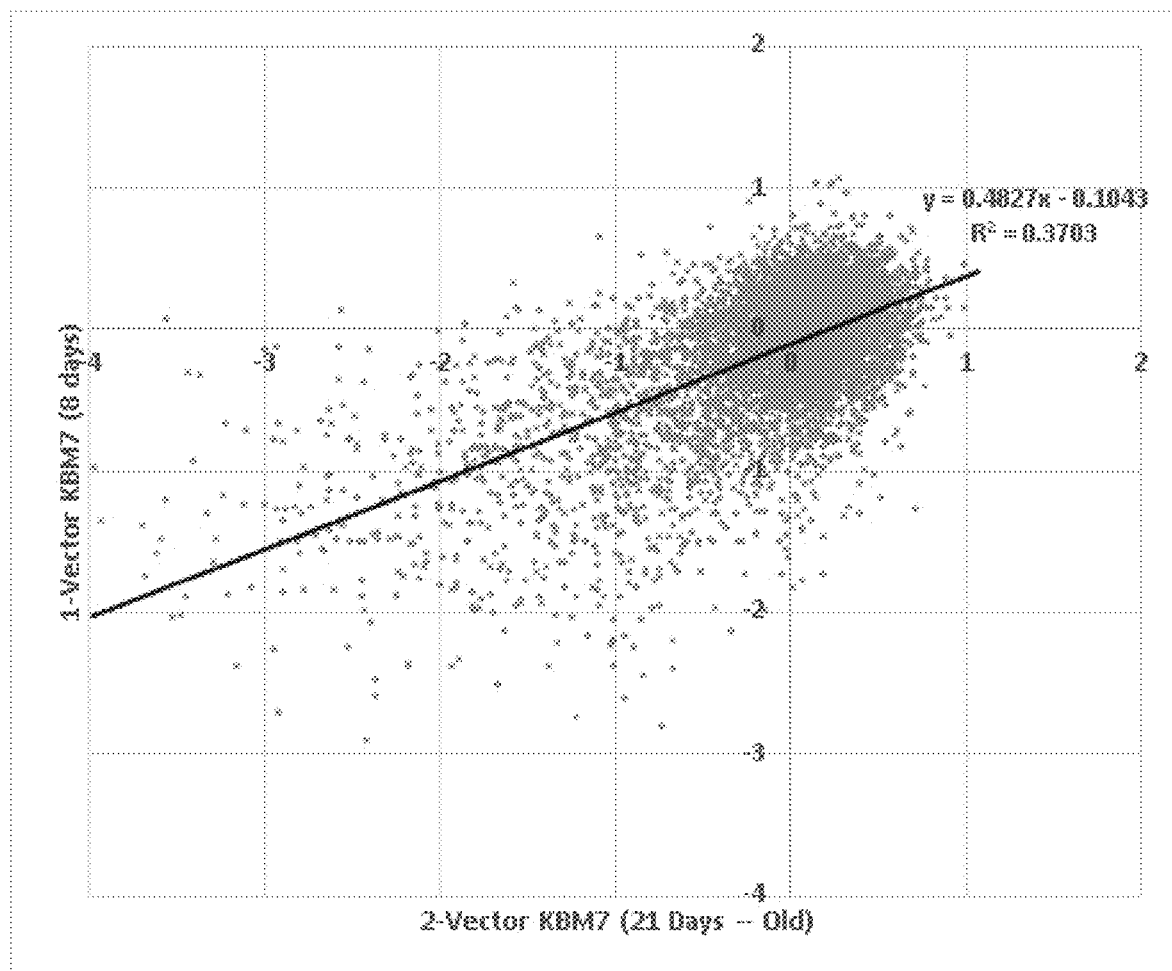
FIG. 11 shows concordance on a gene-level with the previous data (when looking at approximately 7,000 genes).
Figure 12:
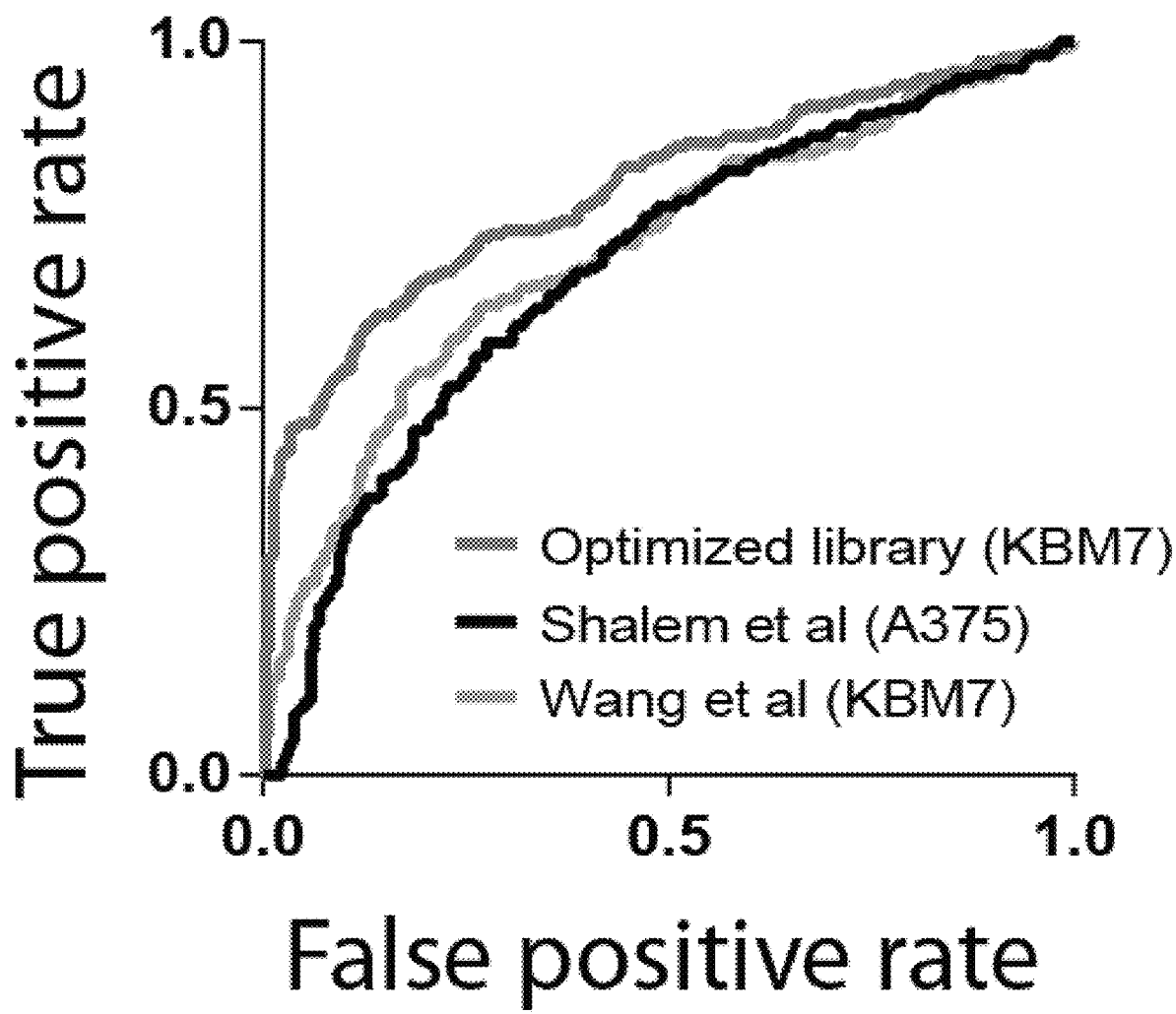
FIG. 12 is a graph of true vs false positives using gene scores from the herein-described improved optimized screening—that obtains improved and optimized sgRNA library(ies)—as well data obtained in previous screens performed (Shalem, Wang) to predict the essentiality of homologous genes in budding yeast where gene knockouts have been systematically generated and assessed for viability.

A HiSeq run was performed on some essentiality screens using the 1-vector genome-wide 180K libraries. In a sample of KBM7s that had been grown for 8 days (previous examples KBM7s can be cultured for 16-20 days). FIG. 10 is a graph showing depletion of sgRNAs targeting ribosomal proteins. The magnitude of depletion is expected to increase over time. FIG. 11 shows concordance on a gene-level with the previous data (when looking at approximately 7,000 genes). It is clearly correlated; the r^2 between KBM7 and HL60 was 0.48 (grown for 3 weeks with the same sgRNA designs for a given gene). Manual inspection of the top genes all made biological sense (BCR-ABL, splicing, ribosomal, etc). Also, FIG. 12 is a graph of true vs false positives. As shown in FIG. 12, Applicants ranked genes using gene scores from the herein-described improved optimized screening—that obtains improved and optimized sgRNA library(ies)—as well data obtained in previous screens performed (Shalem, Wang) that also obtained libraries, and measured how well they could predict the essentiality of homologs in budding yeast, where knockout mutants have been systematically generated and analyzed. Although perfect agreement in gene essentiality between two species would not be expected, Applicants reasoned that better methods of assessing human gene essentiality would more accurately predict yeast gene essentiality. From this analysis Applicants found that the improved optimized screening herein-described obtained an improved sgRNA library that did indeed gave better results.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

REFERENCES (CONTENTS OF WHICH ARE INCORPORATED HEREIN IN THEIR ENTIRETY)

1. Urnov, F. D., Rebar, E. J., Holmes, M. C., Zhang, H. S. & Gregory, P. D. Genome editing with engineered zinc finger nucleases. *Nat. Rev. Genet.* 11, 636-646 (2010).
2. Bogdanove, A. J. & Voytas, D. F. TAL effectors: customizable proteins for DNA targeting. *Science* 333, 1843-1846 (2011).
3. Stoddard, B. L. Homing endonuclease structure and function. *Q. Rev. Biophys.* 38, 49-95 (2005).
4. Bae, T. & Schneewind, O. Allelic replacement in *Staphylococcus aureus* with inducible counter-selection. Plasmid 55, 58-63 (2006).
5. Sung, C. K., Li, H., Claverys, J. P. & Morrison, D. A. An rpsL cassette, janus, for gene replacement through negative selection in *Streptococcus pneumoniae*. *Appl. Environ. Microbiol.* 67, 5190-5196 (2001).
6. Sharan, S. K., Thomason, L. C., Kuznetsov, S. G. & Court, D. L. Recombineering: a homologous recombination-based method of genetic engineering. *Nat. Protoc.* 4, 206-223 (2009).
7. Jinek, M. et al. A programmable dual-RNA-guided DNA endonuclease in adaptive bacterial immunity. *Science* 337, 816-821 (2012).
8. Deveau, H., Garneau, J. E. & Moineau, S. CRISPR/Cas system and its role in phage-bacteria interactions. Annu. Rev. Alicrobiol. 64, 475-493 (2010).
9. Horvath, P. & Barrangou, R. CRISPR/Cas, the immune system of bacteria and archaea. *Science* 327, 167-170 (2010).
10. Terns, M. P. & Terns, R. M. CRISPR-based adaptive immune systems. *Curr. Opin. Microbiol.* 14, 321-327 (2011).
11. van der Oost, J., Jore, M. M., Westra, E. R., Lundgren, M. & Brouns, S. J. CRISPR-based adaptive and heritable immunity in prokaryotes. *Trends. Biochem. Sci.* 34, 401-407 (2009).
12. Brouns, S. J. et al. Small CRISPR RNAs guide antiviral defense in prokaryotes. *Science* 321, 960-964 (2008).
13. Carte, J., Wang, R., Li, H., Terns, R. M. & Terns, M. P. Cas6 is an endoribonuclease that generates guide RNAs for invader defense in prokaryotes. *Genes Dev.* 22, 3489-3496 (2008).
14. Deltcheva, E. et al. CRISPR RNA maturation by trans-encoded small RNA and host factor RNase III. *Nature* 471, 602-607 (2011).
15. Hatoum-Aslan, A., Maniv, I. & Marraffini, L. A. Mature clustered, regularly interspaced, short palindromic repeats RNA (crRNA) length is measured by a ruler mechanism anchored at the precursor processing site. *Proc. Natl. Acad. Sci. U.S.A.* 108, 21218-21222 (2011).
16. Haurwitz, R. E., Jinek, M., Wiedenheft, B., Zhou, K. & Doudna, J. A. Sequence- and structure-specific RNA processing by a CRISPR endonuclease. *Science* 329, 1355-1358 (2010).
17. Deveau, H. et al. Phage response to CRISPR-encoded resistance in *Streptococcus thermophilus*. *J. Bacteriol.* 190, 1390-1400 (2008).
18. Gasiunas, G., Barrangou, R., Horvath, P. & Siksnys, V. Cas9-crRNA ribonucleoprotein complex mediates specific DNA cleavage for adaptive immunity in bacteria. *Proc. Natl. Acad. Sci. U.S.A.* (2012).
19. Makarova, K. S., Aravind, L., Wolf, Y. I. & Koonin, E. V. Unification of Cas protein families and a simple scenario for the origin and evolution of CRISPR-Cas systems. *Biol. Direct.* 6, 38 (2011).
20. Barrangou, R. RNA-mediated programmable DNA cleavage. *Nat. Biotechnol.* 30, 836-838 (2012).
21. Brouns, S. J. Molecular biology. A Swiss army knife of immunity. *Science* 337, 808-809 (2012).
22. Carroll, D. A CRISPR Approach to Gene Targeting. *Mol. Ther.* 20, 1658-1660 (2012).
23. Bikard, D., Hatoum-Aslan, A., Mucida, D. & Marraffini, L. A. CRISPR interference can prevent natural transformation and virulence acquisition during in vivo bacterial infection. *Cell Host Microbe* 12, 177-186 (2012).
24. Sapranauskas, R. et al. The *Streptococcus thermophilus* CRISPR/Cas system provides immunity in *Escherichia coli*. *Nucleic Acids Res.* (2011).
25. Semenova, E. et al. Interference by clustered regularly interspaced short palindromic repeat (CRISPR) RNA is governed by a seed sequence. *Proc. Natl. Acad Sci. U.S.A.* (2011).
26. Wiedenheft, B. et al. RNA-guided complex from a bacterial immune system enhances target recognition through seed sequence interactions. *Proc. Natl. Acad. Sci. U.S.A.* (2011).

27. Zahner, D. & Hakenbeck, R. The *Streptococcus pneumoniae* beta-galactosidase is a surface protein. *J. Bacteriol.* 182, 5919-5921 (2000).
28. Marraffini, L. A., Dedent, A. C. & Schneewind, O. Sortases and the art of anchoring proteins to the envelopes of gram-positive bacteria. *Microbiol. Mol. Biol. Rev.* 70, 192-221 (2006).
29. Motamedi, M. R., Szigety, S. K. & Rosenberg, S. M. Double-strand-break repair recombination in *Escherichia coli*: physical evidence for a DNA replication mechanism in vivo. *Genes Dev.* 13, 2889-2903 (1999).
30. Hosaka, T. et al. The novel mutation K87E in ribosomal protein S12 enhances protein synthesis activity during the late growth phase in *Escherichia coli*. *Mol. Genet. Genomics* 271, 317-324 (2004).
31. Costantino, N. & Court, D. L. Enhanced levels of lambda Red-mediated recombinants in mismatch repair mutants. *Proc. Natl. Acad. Sci. U.S.A.* 100, 15748-15753 (2003).
32. Edgar, R. & Qimron, U. The *Escherichia coli* CRISPR system protects from lambda lysogenization, lysogens, and prophage induction. *J. Bacteriol.* 192, 6291-6294 (2010).
33. Marraffini, L. A. & Sontheimer, E. J. Self versus non-self discrimination during CRISPR RNA-directed immunity. *Nature* 463, 568-571 (2010).
34. Fischer, S. et al. An archaeal immune system can detect multiple Protospacer Adjacent Motifs (PAMs) to target invader DNA. *J. Biol. Chem.* 287, 33351-33363 (2012).
35. Gudbergsdottir, S. et al. Dynamic properties of the *Sulfolobus* CRISPR/Cas and CRISPR/Cmr systems when challenged with vector-borne viral and plasmid genes and protospacers. *Mol. Microbiol.* 79, 35-49 (2011).
36. Wang, H. H. et al. Genome-scale promoter engineering by coselection MAGE. *Nat Methods* 9, 591-593 (2012).
37. Cong, L. et al. Multiplex Genome Engineering Using CRISPR/Cas Systems. *Science* 339, 819 (Feb. 15, 2013).
38. Mali, P. et al. RNA-Guided Human Genome Engineering via Cas9. *Science* 339, 823 (Feb. 15, 2013).
39. Hoskins, J. et al. Genome of the bacterium *Streptococcus pneumoniae* strain R6. *J. Bacteriol.* 183, 5709-5717 (2001).
40. Havarstein, L. S., Coomaraswamy, G. & Morrison, D. A. An unmodified heptadecapeptide pheromone induces competence for genetic transformation in *Streptococcus pneumoniae*. *Proc. Natl. Acad. Sci. U.S.A.* 92, 11140-11144 (1995).
41. Horinouchi, S. & Weisblum, B. Nucleotide sequence and functional map of pC194, a plasmid that specifies inducible chloramphenicol resistance. *J. Bacteriol.* 150, 815-825 (1982).
42. Horton, R. M. In Vitro Recombination and Mutagenesis of DNA: SOEing Together Tailor-Made Genes. *Methods Mol. Biol.* 15, 251-261 (1993).
43. Podbielski, A., Spellerberg, B., Woischnik, M., Pohl, B. & Lutticken, R. Novel series of plasmid vectors for gene inactivation and expression analysis in group A streptococci (GAS). *Gene* 177, 137-147 (1996).
44. Husmann, L. K., Scott, J. R., Lindahl, G. & Stenberg, L. Expression of the Arp protein, a member of the M protein family, is not sufficient to inhibit phagocytosis of *Streptococcus pyogenes*. *Infection and immunity* 63, 345-348 (1995).
45. Gibson, D. G. et al. Enzymatic assembly of DNA molecules up to several hundred kilobases. *Nat Methods* 6, 343-345 (2009).
46. Garneau J. E. et al. The CRISPR/Cas bacterial immune system cleaves bacteriophage and plasmid DNA. *Nature* 468, 67-71 (4 Nov. 2010).
47. Barrangou R. et al. CRISPR provides acquired resistance against viruses in prokaryotes. *Science.* 2007 Mar. 23, 315(5819):1709-12.
48. Ishino Y. et al. Nucleotide sequence of the iap gene, responsible for alkaline phosphatase isozyme conversion in *Escherichia coli*, and identification of the gene product. *J Bacteriol.* 1987 December; 169(12):5429-33.
49. Mojica F. J. M et al. Biological significance of a family of regularly spaced repeats in the genomes of Archaea, Bacteria and mitochondria. *Molecular Microbiology* (2000) 36(1), 244-246.
50. Jansen R. et al. Identification of genes that are associated with DNA repeats in prokaryotes. *Molecular Microbiology* (2002) 43(6), 1565-1575.
51. Luo B et al., Highly parallel identification of essential genes in cancer cells. *Proc Natl Acad Sci USA.* 2008 Dec. 23; 105(51):20380-5.
52. Paddison P J et al., A resource for large-scale RNA-interference-based screens in mammals. *Nature.* 2004 Mar. 25; 428(6981):427-31.
53. Berns K et al., A large-scale RNAi screen in human cells identifies new components of the p53 pathway, *Nature.* 2004 Mar. 25; 428(6981):431-7.
54. Moffat J et al., A lentiviral RNAi library for human and mouse genes applied to an arrayed viral high-content screen. *Cell.* 2006 Mar. 24; 124(6):1283-98.
55. Zeng Y et al., Both natural and designed micro RNAs can inhibit the expression of cognate mRNAs when expressed in human cells. *Mol Cell.* 2002 Jun.; 9(6):1327-33.
56. Hemann et al., An epi-allelic series of p53 hypomorphs created by stable RNAi produces distinct tumor phenotypes in vivo. *Nat Genet.* 2003 March; 33(3):396-400. Epub 2003 Feb. 3.
57. Stewart S A et al., Lentivirus-delivered stable gene silencing by RNAi in primary cells. *RNA.* 2003 Apr.; 9(4):493-501.
58. Brummelkamp T R et al., A system for stable expression of short interfering RNAs in mammalian cells. *Science.* 2002 Apr. 19; 296(5567):550-3. Epub 2002 Mar. 21.
59. E. S. Lander, Initial impact of the sequencing of the human genome. *Nature* 470, 187 (Feb. 10, 2011).
60. V. N. Ngo et al., A loss-of-function RNA interference screen for molecular targets in cancer. *Nature* 441, 106 (Apr. 29, 2006).
61. M. Boutros et al., Genome-wide RNAi analysis of growth and viability in *Drosophila* cells. *Science* 303, 832 (Feb. 6, 2004).
62. R. Rad et al., PiggyBac transposon mutagenesis: a tool for cancer gene discovery in mice. *Science* 330, 1104 (Nov. 19, 2010).
63. A. H. Tong et al., Global mapping of the yeast genetic interaction network. *Science* 303, 808 (Feb. 6, 2004).
64. J. E. Carette et al., Haploid genetic screens in human cells identify host factors used by pathogens. *Science* 326, 1231 (Nov. 27, 2009).
65. A. L. Jackson et al., Widespread siRNA "off-target" transcript silencing mediated by seed region sequence complementarity. *Rna* 12, 1179 (July, 2006).
66. W. G. Kaelin, Use and Abuse of RNAi to Study Mammalian Gene Function. *Science* 337, 421 (Jul. 26, 2012).

67. C. J. Echeverri et al., Minimizing the risk of reporting false positives in large-scale RNAi screens. Nature methods 3, 777 (October, 2006).
68. S. Konermann et al., Optical control of mammalian endogenous transcription and epigenetic states. *Nature* 500, 472 (Aug. 22, 2013).
69. L. A. Gilbert et al., CRISPR-Mediated Modular RNA-Guided Regulation of Transcription in Eukaryotes. Cell, (July, 2013).
70. P. Perez-Pinera et al., RNA-guided gene activation by CRISPR-Cas9-based transcription factors. *Nature methods*, (Jul. 25, 2013).
71. M. L. Maeder et al., CRISPR RNA-guided activation of endogenous human genes. *Nature methods*, (Jul. 25, 2013).
72. A. P. Blanchard, L. Hood, Sequence to array: probing the genome's secrets. *Nat Biotechnol* 14, 1649 (December, 1996).
73. P. D. Hsu et al., DNA targeting specificity of RNA-guided Cas9 nucleases. *Nat Biotechnol* 31, 827 (September, 2013).
74. A. Subramanian et al., Gene set enrichment analysis: a knowledge-based approach for interpreting genome-wide expression profiles. *Proc Natl Acad Sci USA* 102, 15545 (Oct. 25, 2005).
75. C. M. Johannessen et al., COT drives resistance to RAF inhibition through MAP kinase pathway reactivation. *Nature* 468, 968 (Dec. 16, 2010).
76. K. T. Flaherty et al., Inhibition of mutated, activated BRAF in metastatic melanoma. *The New England journal of medicine* 363, 809 (Aug. 26, 2010).
77. H. Davies et al., Mutations of the BRAF gene in human cancer. *Nature* 417, 949 (Jun. 27, 2002).
78. S. Huang et al., MED12 Controls the Response to Multiple Cancer Drugs through Regulation of TGF-β Receptor Signaling. *Cell* 151, 937 (Nov. 21, 2012).
79. S. R. Whittaker et al., A Genome-Scale RNA Interference Screen Implicates NF1 Loss in Resistance to RAF Inhibition. *Cancer Discovery* 3, 350 (Apr. 7, 2013).
80. A. L. Lin, D. H. Gutmann, Advances in the treatment of neurofibromatosis-associated tumours. Nature reviews. Clinical oncology, (Aug. 13, 2013).
81. Y. Fu et al., High-frequency off-target mutagenesis induced by CRISPR-Cas nucleases in human cells. *Nature Biotechnology*, 1 (Jul. 23, 2013).
82. F. A. Ran et al., Double Nicking by RNA-Guided CRISPR Cas9 for Enhanced Genome Editing Specificity. *Cell*, 1 (Aug. 28, 2013).
83. C. Trapnell, L. Pachter, S. L. Salzberg, TopHat: discovering splice junctions with RNA-Seq. Bioinformatics 25, 1105 (May 1, 2009).
84. C. Trapnell et al., Differential gene and transcript expression analysis of RNA-seq experiments with TopHat and Cufflinks. Nature protocols 7, 562 (March, 2012).
85. J. Merkin, C. Russell, P. Chen, C. B. Burge, Evolutionary dynamics of gene and isoform regulation in Mammalian tissues. *Science* 338, 1593 (Dec. 21, 2012).
86. B. Langmead, C. Trapnell, M. Pop, S. L. Salzberg, Ultrafast and memory-efficient alignment of short DNA sequences to the human genome. Genome biology 10, R25 (2009).
87. P. Mali et al., CAS9 transcriptional activators for target specificity screening and paired nickases for cooperative genome engineering. *Nat Biotechnol* 31, 833 (September, 2013).
88. G. Giaever et al., Functional profiling of the *Saccharomyces cerevisiae* genome. *Nature* 418, 387 (2002).
89. M. Costanzo et al., *The genetic landscape of a cell. Science* 327, 425 (Jan. 22, 2010).
90. A. Fire et al., Potent and specific genetic interference by double-stranded RNA in *Caenorhabditis elegans. Nature.* 1998 Feb. 19; 391(6669):806-11.
91. H. W. Cheung et al., Systematic investigation of genetic vulnerabilities across cancer cell lines reveals lineage-specific dependencies in ovarian cancer. *Proceedings of the National Academy of Sciences* 108, 12372 (Jul. 26, 2011).
92. M. Booker et al., False negative rates in *Drosophila* cell-based RNAi screens: a case study, *BMC Genomics* 12, 50 (2011).
93. G. Guo, W. Wang, A. Bradley, Mismatch repair genes identified using genetic screens in Blm-deficient embryonic stem cells. *Nature* 429, 891 (2004).
94. K. Chylinski, A. Le Rhun, E. Charpentier, The tracrRNA and Cas9 families of type II CRISPR-Cas immunity systems. RNA Biology 10, 726 (2013).
95. W. Y. Hwang et al., Efficient genome editing in zebrafish using a CRISPR-Cas system. *Nat Biotech* 31, 227 (2013).
96. H. Wang et al., One-step generation of mice carrying mutations in multiple genes by CRISPR/Cas-mediated genome engineering. *Cell* 153, 910 (2013).
97. T. Horii, D. Tamura, S. Morita, M. Kimura, I. Hatada, Generation of an ICF Syndrome Model by Efficient Genome Editing of Human Induced Pluripotent Stem Cells Using the CRISPR System. *International Journal of Molecular Sciences* 14, 19774 (2013).
98. T. Yan, S. E. Berry, A. B. Desai, T. J. Kinsella, DNA mismatch repair (MMR) mediates 6-thioguanine genotoxicity by introducing single-strand breaks to signal a G2-M arrest in MMR-proficient RKO cells. *Clinical Cancer Research* 9, 2327 (Jun. 1, 2003, 2003).
99. R. D. Kolodner, G. T. Marsischky, Eukaryotic DNA mismatch repair. Current Opinion in Genetics & Development 9, 89 (1999).
100. D. J. Burgess et al., Topoisomerase levels determine chemotherapy response in vitro and in vivo. *Proceedings of the National Academy of Sciences* 105, 9053 (Jul. 1, 2008).
101. B. Scappini et al., Changes associated with the development of resistance to imatinib (STI571) in two leukemia cell lines expressing p210 Bcr/Abl protein. *Cancer* 100, 1459 (2004).
102. S. Xue, M. Barna, Specialized ribosomes: a new frontier in gene regulation and organismal biology. *Nat Rev Mol Cell Biol* 13, 355 (2012).
103. C. M. Johnston et al., Large-scale population study of human cell lines indicates that dosage compensation is virtually complete. *PLoS Genet* 4, e9 (2008).
104. Luke A. Gilbert et al., CRISPR-mediated modular RNA-guided regulation of transcription in eukaryotes. *Cell* 154, 442 (2013).
105. Lei S. Qi et al., Repurposing CRISPR as an RNA-guided platform for sequence-specific control of gene expression. *Cell* 152, 1173 (2013).
106. T. J. Cradick, E. J. Fine, C. J. Antico, G. Bao, CRISPR/Cas9 systems targeting β-globin and CCR5 genes have substantial off-target activity. *Nucleic Acids Research*, (Aug. 11, 2013).
107. J. M. Engreitz et al., The Xist lncRNA exploits three-dimensional genome architecture to spread across the X chromosome. *Science.* 2013 Aug. 16; 341 (6147).

108. K. Yoshimoto et al., Complex DNA repair pathways as possible therapeutic targets to overcome temozolomide resistance in glioblastoma. *Front Oncol.* 2012 Dec. 5; 2:186.
109. X. Liu, M. Vorontchikhina, Y. L. Wang, F. Faiola, E. Martinez, STAGA recruits Mediator to the MYC oncoprotein to stimulate transcription and cell proliferation. Molecular and cellular biology 28, 108 (January, 2008).
110. B. Langmead, S. L. Salzberg, Fast gapped-read alignment with Bowtie 2. *Nat Meth* 9, 357-359 (2012).
111. S. S. Liu et al., Identification and characterization of a novel gene, clorf109, encoding a CK2 substrate that is involved in cancer cell proliferation. *Journal of Biomedical Science* 19, 49 (2012).
112. R. Renella et al., Codanin-1 mutations in congenital dyserythropoietic anemia type 1 affect HP1α localization in erythroblasts. *Blood* 117, 6928-6938 (2011).
113. S. H. Chen et al., A Knockout Mouse Approach Reveals that TCTP Functions as an Essential Factor for Cell Proliferation and Survival in a Tissue- or Cell Type-specific Manner. *Molecular Biology of the Cell* 18, 2525-2532 (2007).
114. C. Cayrol et al., The THAP-zinc finger protein THAP1 regulates endothelial cell proliferation through modulation of pRB/E2F cell-cycle target genes. *Blood* 109, 584-594 (2007).
115. B. Sonnichsen et al., Full-genome RNAi profiling of early embryogenesis in *Caenorhabditis elegans*. *Nature* 434, 462-469 (2005).
116. J. F. Rual et al., Toward Improving *Caenorhabditis elegans* Phenome Mapping With an ORFeome-Based RNAi Library. *Genome Research* 14, 2162-2168 (2004).
117. J L. Mummery-Widmer et al., Genome-wide analysis of Notch signalling in *Drosophila* by transgenic RNAi. *Nature* 458, 987-992 (2009).
118. A. C. Spradling et al., The Berkeley *Drosophila* Genome Project Gene Disruption Project: Single P-Element Insertions Mutating 25% of Vital *Drosophila* Genes. Genetics 153, 135-177 (1999).
119. A. Amsterdam et al. Identification of 315 genes essential for early zebrafish development. *Proc Natl Acad Sci USA.* 2004 Aug. 31; 101(35):12792-7.

What is claimed is:

1. A genome-wide screening method, comprising knocking out in parallel a plurality of genes in a genome by a method which comprises:
   (a) selecting a plurality of guide sequences from a library of candidate guide sequences, each guide sequence targeting a DNA molecule encoding a gene product, wherein a guide sequence is selected if the candidate guide sequence satisfies the following rules:
      (i) binding affinity between the candidate guide sequence and a CRISPR-Cas protein is higher than binding affinity between a reference guide sequence in the library and the CRISPR-Cas protein,
      (ii) none of the last four nucleotides of the candidate guide sequence is a pyrimidine, and
      (iii) the candidate guide sequence has a % GC nucleotide content between 20% and 80%; and
   (b) introducing into a population of cells a composition comprising:
      (i) a plurality of guide polynucleotide sequences, each comprising a guide sequence from (a), whereby different guide polynucleotide sequences are introduced into different cells of the population; and
      (ii) a Type II CRISPR-Cas protein or a polynucleotide sequence encoding a Type II CRISPR-Cas protein,
   wherein each guide sequence directs sequence-specific binding of a CRISPR complex to a target sequence in a genomic locus of the DNA molecule encoding the gene product,
   wherein the CRISPR complex comprises the CRISPR-Cas protein complexed with a guide sequence that is hybridized to the target sequence, and
   wherein the CRISPR-Cas protein cleaves the genomic locus of the DNA molecule encoding the gene product, whereby each cell in the population of cells has a unique gene knocked out in parallel.

2. The method of claim 1, wherein the selection of the guide sequences further comprises predicting the efficacy of a guide sequence based on one or more of:
   targeting early constitutive exons of coding genes, or
   targeting of a non-transcribed DNA strand.

3. The method of claim 1, wherein the cell is a eukaryotic cell.

4. The method of claim 3, wherein the eukaryotic cell is a human cell, animal cell, or plant cell.

5. The method of claim 1, wherein the CRISPR-Cas system guide polynucleotide sequences and the CRISPR-Cas protein are comprised in one or more vectors.

6. The method of claim 5, wherein the one or more vectors is a lentivirus, an adenovirus or an AAV vector.

7. The method of claim 1, where the CRISPR-Cas system guide polynucleotide sequences and the CRISPR-Cas protein are comprised in one vector.

8. The method of claim 7, wherein the one vector is a lentivirus, an adenovirus or an AAV vector.

9. The method of claim 1, wherein the targeting is of about 100 or more sequences.

10. The method of claim 1, wherein the CRISPR-Cas protein is a Cas9.

11. The method of claim 10, wherein the Cas9 protein is *Streptococcus pyogenes* Cas9 or *Staphylococcus aureus* Cas9.

12. The method of claim 1, wherein the targeting is of about 1000 or more sequences.

13. The method of claim 1, wherein the targeting is of about 20,000 or more sequences.

14. The method of claim 1, wherein the targeting is of the entire genome.

15. The method of claim 1, further comprising ranking the candidate guide sequences based on off-target scores and selecting guide sequences with the lowest scores.

16. The method of claim 1, wherein each cell has introduced a single CRISPR-Cas system guide polynucleotide sequence.

17. The method of claim 1, wherein the cells are transduced with a multiplicity of infection (MOI) of 0.3-0.75.

18. The method of claim 1, comprising selecting guide sequences that target early constitutive exons of coding genes and/or selecting guide sequences that target non-transcribed DNA strands.

19. The method of claim 1, further comprising selecting guide sequences that do not comprise a thymine at any one of the last four nucleotides of the guide sequences.

* * * * *

UNITED STATES PATENT AND TRADEMARK OFFICE
CERTIFICATE OF CORRECTION

Page 1 of 4

PATENT NO. : 11,149,267 B2
APPLICATION NO. : 15/141348
DATED : October 19, 2021
INVENTOR(S) : Tim Wang et al.

It is certified that error appears in the above-identified patent and that said Letters Patent is hereby corrected as shown below:

On the Title Page

On the page 2, in Column 1, under (56), "Other Publications", Line 7, delete "Elake" and insert -- Blake --.

On the page 2, in Column 1, under (56), "Other Publications", Line 8, delete "Elake" and insert -- Blake --.

On the page 2, in Column 1, under (56), "Other Publications", Line 10, delete "Frashant" and insert -- Prashant --.

On the page 2, in Column 1, under (56), "Other Publications", Line 11, after "No." insert -- 61/613,373 --.

On the page 3, in Column 1, under (56), "Other Publications", Line 17, delete "1-35," and insert -- 1-35. --.

On the page 3, in Column 2, under (56), "Other Publications", Line 36, delete "416/viru." and insert -- 4161/viru. --.

On the page 4, in Column 2, under (56), "Other Publications", Line 38, delete "nbt.2675," and insert -- nbt.2675. --.

On the page 5, in Column 1, under (56), "Other Publications", Line 25, delete "2015;" and insert -- 2015, --.

On the page 5, in Column 1, under (56), "Other Publications", Line 33, delete "al.," and insert -- al. --.

On the page 5, in Column 1, under (56), "Other Publications", Line 51, delete "forurm/#ltopic" and insert -- forum/#!topic/ --.

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*

On the page 5, in Column 1, under (56), "Other Publications", Line 54, delete "ltop1c/" and insert -- !topic/ --.

On the page 5, in Column 1, under (56), "Other Publications", Line 59, delete "'iprofo _nt" and insert -- !profo_nt --.

On the page 5, in Column 1, under (56), "Other Publications", Line 60, delete "Fu3r-1/" and insert -- Fu3r-l/ --.

On the page 5, in Column 1, under (56), "Other Publications", Line 62, delete "Lou" and insert -- Luo --.

On the page 5, in Column 2, under (56), "Other Publications", Line 15, delete "geonome" and insert -- genome --.

On the page 6, in Column 1, under (56), "Other Publications", Line 10, delete "Zho," and insert -- Cho, --.

In the Specification

In Column 2, Line 5, delete "HG03067" and insert -- HG003067 --.

In Column 2, Line 15, delete "10,724" and insert -- 11,102 --.

In Column 3, Line 3, delete "23:" and insert -- 23; --.

In Column 10, Line 32, delete "I" and insert -- II --.

In Column 12, Line 11, delete "PSMA 4." and insert -- PSMA4. --.

In Column 12, Line 44, delete "log 2" and insert -- $\log_2$ --.

In Column 12, Line 58, delete "log 2" and insert -- $\log_2$ --.

In Column 13, Line 1, delete "log 2" and insert -- $\log_2$ --.

In Column 13, Line 5, delete "log 2" and insert -- $\log_2$ --.

In Column 13, Line 12, delete "sgAAVS-modified" and insert -- sgAAVS1-modified --.

In Column 13, Line 32, delete "log 2" and insert -- $\log_2$ --.

In Column 13, Line 33, delete "log 2" and insert -- $\log_2$ --.

In Column 15, Line 12, delete "Manraffini" and insert -- Marraffini --.

CERTIFICATE OF CORRECTION (continued)
U.S. Pat. No. 11,149,267 B2

In Column 15, Line 24, delete "Nature2466." and insert -- Nature12466. --.

In Column 15, Line 37, after "Jul. 21;" delete "Y".

In Column 15, Line 44, delete "Hecki," and insert -- Heckl, --.

In Column 15, Line 62, delete "3:" and insert -- 3; --.

In Column 20, Line 41, delete "900," and insert -- 90%, --.

In Column 23, Line 36, delete "H" and insert -- H1 --.

In Column 26, Line 6, delete "Silfolobus," and insert -- Sulfolobus, --.

In Column 26, Line 9, delete "Aqifex," and insert -- Aquifex, --.

In Column 26, Line 29, delete "mice" and insert -- mice; --.

In Column 27, Line 17, delete "5-0/o." and insert -- 5-0%. --.

In Column 31, Line 27, delete "is" and insert -- in --.

In Column 31, Line 45, delete "NNNNNNNNNNNNNNNNNNNNNAGAAW" and insert -- NNNNNNNNNNNNNNNNNNNNNAGAAW --.

In Column 31, Line 55, delete "11" and insert -- 9 --.

In Column 31, Line 55, delete "12" and insert -- 13 --.

In Column 31, Line 55, delete "15" and insert -- 16 --.

In Column 31, Line 55, delete "12" and insert -- 10 --.

In Column 31, Line 56, delete "nucleotide)" and insert -- nucleotide, unknown, other, or a modified nucleotide) --.

In Column 32, Line 15, delete "Biotechology" and insert -- Biotechnology --.

In Column 36, Line 11, delete "level," and insert -- level; --.

In Column 38, Line 55, delete "0.0072" and insert -- 0.0372 --.

In Column 38, Lines 62-63, delete "CRISPR-Cas93system." and insert -- CRISPR-Cas9 system. --.

In Column 39, Line 15, delete "(>99° %)" and insert -- (>99%) --.

CERTIFICATE OF CORRECTION (continued)
U.S. Pat. No. 11,149,267 B2

In Column 40, Line 57, delete "sgAAVS-" and insert -- sgAAVS1- --.

In Column 47, Line 53, delete "penicilin/" and insert -- penicillin/ --.

In Column 50, Line 22, delete "(sgAAVS)." and insert -- (sgAAVS1). --.

In Column 50, Line 61, delete "log 2" and insert -- $log_2$ --.

In Column 51, Line 4, delete "log 2" and insert -- $log_2$ --.

In Column 51, Line 7, delete "log 2" and insert -- $log_2$ --.

In Column 51, Line 16, delete "log 2" and insert -- $log_2$ --.

In Column 52, Line 11, delete "4C." and insert -- 4° C. --.

In Column 52, Line 43, delete "Log" and insert -- $Log_2$ --.

In Column 52, Line 50, delete "RP4Y1," and insert -- RPS4Y1, --.

In Column 52, Line 67, delete "RPS4Y," and insert -- RPS4Y1, --.

In Column 54, Line 6, delete "Alicrobiol." and insert -- Microbiol. --.

In Column 54, Line 53, delete "Marraffni," and insert -- Marraffini, --.

In Column 56, Line 5, delete "23," and insert -- 23; --.

In Column 58, Line 65, delete "IncRNA" and insert -- lncRNA --.

SEQUENCE LISTING

```
<160> NUMBER OF SEQ ID NOS: 32

<210> SEQ ID NO 1
<211> LENGTH: 23
<212> TYPE: DNA
<213> ORGANISM: Streptococcus pyogenes
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (9)..(20)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, t, unknown, other, or a modified
      nucleotide

<400> SEQUENCE: 1 nnnnnnnnn nnnnnnnnnn ngg                                           23

<210> SEQ ID NO 2
<211> LENGTH: 15
<212> TYPE: DNA
<213> ORGANISM: Streptococcus pyogenes
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, t, unknown, other, or a modified
      nucleotide

<400> SEQUENCE: 2
nnnnnnnnnn nnngg                                                   15

<210> SEQ ID NO 3
<211> LENGTH: 23
<212> TYPE: DNA
<213> ORGANISM: Streptococcus pyogenes
<220> FEATURE:
<221> NAME/KEY: misc_feature
<222> LOCATION: (1)..(9)
```

```
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, t, unknown, other, or a modified
      nucleotide

<400> SEQUENCE: 3
nnnnnnnnnn nnnnnnnnnn ngg                                              23

<210> SEQ ID NO 4
<211> LENGTH: 14
<212> TYPE: DNA
<213> ORGANISM: Streptococcus pyogenes
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, t, unknown, other, or a modified
      nucleotide

<400> SEQUENCE: 4
nnnnnnnnnn nngg                                                        14

<210> SEQ ID NO 5
<211> LENGTH: 27
<212> TYPE: DNA
<213> ORGANISM: Streptococcus thermophilus
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (9)..(20)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, t, unknown, other, or a modified
      nucleotide
<220> FEATURE:
<221> NAME/KEY: misc_feature
<222> LOCATION: (27)..(27)
<223> OTHER INFORMATION: w is a or t

<400> SEQUENCE: 5
nnnnnnnnnn nnnnnnnnnn nnagaaw                                          27

<210> SEQ ID NO 6
<211> LENGTH: 19
<212> TYPE: DNA
<213> ORGANISM: Streptococcus thermophilus
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, t, unknown, other, or a modified
      nucleotide
<220> FEATURE:
<221> NAME/KEY: misc_feature
<222> LOCATION: (19)..(19)
<223> OTHER INFORMATION: w is a or t
```

```
<400> SEQUENCE: 6 nnnnnnnnn nnnnagaaw                                                              19

<210> SEQ ID NO 7
<211> LENGTH: 27
<212> TYPE: DNA
<213> ORGANISM: Streptococcus thermophilus
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, t, unknown, other, or a modified
      nucleotide
<220> FEATURE:
<221> NAME/KEY: misc_feature
<222> LOCATION: (27)..(27)
<223> OTHER INFORMATION: w is a or t

<400> SEQUENCE: 7
nnnnnnnnnn nnnnnnnnnn nnagaaw                                                    27

<210> SEQ ID NO 8
<211> LENGTH: 18
<212> TYPE: DNA
<213> ORGANISM: Streptococcus thermophilus
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, t, unknown, other, or a modified
      nucleotide
<220> FEATURE:
<221> NAME/KEY: misc_feature
<222> LOCATION: (18)..(18)
<223> OTHER INFORMATION: w is a or t

<400> SEQUENCE: 8
nnnnnnnnnn nnnagaaw                                                              18

<210> SEQ ID NO 9
<211> LENGTH: 25
<212> TYPE: DNA
<213> ORGANISM: Streptococcus pyogenes
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (9)..(20)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, t, unknown, other, or a modified
      nucleotide
<220> FEATURE:
<221> NAME/KEY: misc_feature
<222> LOCATION: (24)..(24)
<223> OTHER INFORMATION: n is a, c, g, t, unknown, other, or a modified
      nucleotide
```

```
<400> SEQUENCE: 9
nnnnnnnnnn nnnnnnnnnn nggng                                              25

<210> SEQ ID NO 10
<211> LENGTH: 17
<212> TYPE: DNA
<213> ORGANISM: Streptococcus pyogenes
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, t, unknown, other, or a modified
      nucleotide
<220> FEATURE:
<221> NAME/KEY: misc_feature
<222> LOCATION: (16)..(16)
<223> OTHER INFORMATION: n is a, c, g, t, unknown, other, or a modified
      nucleotide

<400> SEQUENCE: 10
nnnnnnnnnn nnnggng                                                       17

<210> SEQ ID NO 11
<211> LENGTH: 25
<212> TYPE: DNA
<213> ORGANISM: Streptococcus pyogenes
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, t, unknown, other, or a modified
      nucleotide
<220> FEATURE:
<221> NAME/KEY: misc_feature
<222> LOCATION: (24)..(24)
<223> OTHER INFORMATION: n is a, c, g, t, unknown, other, or a modified
      nucleotide

<400> SEQUENCE: 11
nnnnnnnnnn nnnnnnnnnn nggng                                              25

<210> SEQ ID NO 12
<211> LENGTH: 16
<212> TYPE: DNA
<213> ORGANISM: Streptococcus pyogenes
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, t, unknown, other, or a modified
      nucleotide
<220> FEATURE:
<221> NAME/KEY: misc_feature
<222> LOCATION: (15)..(15)
<223> OTHER INFORMATION: n is a, c, g, t, unknown, other, or a modified
      nucleotide

<400> SEQUENCE: 12
nnnnnnnnnn nnggng                                                        16
```

```
<210> SEQ ID NO 13
<211> LENGTH: 137
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)
<223> OTHER INFORMATION: n is a, c, g, or t

<400> SEQUENCE: 13
nnnnnnnnnn nnnnnnnnnn gttttttgtac tctcaagatt tagaaataaa tcttgcagaa    60
gctacaaaga taaggcttca tgccgaaatc aacaccctgt cattttatgg cagggtgttt   120
tcgttattta attttttt                                                 137

<210> SEQ ID NO 14
<211> LENGTH: 123
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)
<223> OTHER INFORMATION: n is a, c, g, or t

<400> SEQUENCE: 14
nnnnnnnnnn nnnnnnnnnn gttttttgtac tctcagaaat gcagaagcta caaagataag    60
gcttcatgcc gaaatcaaca ccctgtcatt ttatggcagg gtgttttcgt tatttaattt   120
ttt                                                                 123

<210> SEQ ID NO 15
<211> LENGTH: 110
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)
<223> OTHER INFORMATION: n is a, c, g, or t

<400> SEQUENCE: 15
nnnnnnnnnn nnnnnnnnnn gttttttgtac tctcagaaat gcagaagcta caaagataag    60
gcttcatgcc gaaatcaaca ccctgtcatt ttatggcagg gtgttttttt               110

<210> SEQ ID NO 16
<211> LENGTH: 102
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)
<223> OTHER INFORMATION: n is a, c, g, or t

<400> SEQUENCE: 16
nnnnnnnnnn nnnnnnnnnn gttttagagc tagaaatagc aagttaaaat aaggctagtc    60
cgttatcaac ttgaaaaagt ggcaccgagt cggtgctttt tt                      102

<210> SEQ ID NO 17
```

```
<211> LENGTH: 88
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)
<223> OTHER INFORMATION: n is a, c, g, or t

<400> SEQUENCE: 17
nnnnnnnnnn nnnnnnnnnn gttttagagc tagaaatagc aagttaaaat aaggctagtc    60
cgttatcaac ttgaaaaagt gttttttt                                       88

<210> SEQ ID NO 18
<211> LENGTH: 76
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)
<223> OTHER INFORMATION: n is a, c, g, or t

<400> SEQUENCE: 18
nnnnnnnnnn nnnnnnnnnn gttttagagc tagaaatagc aagttaaaat aaggctagtc    60
cgttatcatt tttttt                                                    76

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
ggggccacta gggacaggat                                                20

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
ccccgttctc ctgtggattc                                                20

<210> SEQ ID NO 21
<211> LENGTH: 20
<212> TYPE: DNA
<213> ORGANISM: Artificial Sequence
<220> FEATURE:
<223> OTHER INFORMATION: Synthetic primer

<400> SEQUENCE: 21
atcctctctg gctccatcgt                                                20

<210> SEQ ID NO 22
<211> LENGTH: 48
<212> TYPE: DNA
<213> ORGANISM: Artificial Sequence
<220> FEATURE:
<223> OTHER INFORMATION: Synthetic primer

<400> SEQUENCE: 22
```
aatgatacgg cgaccaccga gatctacacc ccgttctcct gtggattc        48

<210> SEQ ID NO 23
<211> LENGTH: 45
<212> TYPE: DNA
<213> ORGANISM: Artificial Sequence
<220> FEATURE:
<223> OTHER INFORMATION: Synthetic primer

<400> SEQUENCE: 23
caagcagaag acggcatacg agatcatcct ctctggctcc atcgt            45

<210> SEQ ID NO 24
<211> LENGTH: 42
<212> TYPE: DNA
<213> ORGANISM: Artificial Sequence
<220> FEATURE:
<223> OTHER INFORMATION: Synthetic primer

<400> SEQUENCE: 24
tctggttctg ggtacttttta tctgtcccct ccaccccaca gt              42

<210> SEQ ID NO 25
<211> LENGTH: 21
<212> TYPE: DNA
<213> ORGANISM: Artificial Sequence
<220> FEATURE:
<223> OTHER INFORMATION: Synthetic primer

<400> SEQUENCE: 25
agcgctagct aatgccaact t                                      21

<210> SEQ ID NO 26
<211> LENGTH: 20
<212> TYPE: DNA
<213> ORGANISM: Artificial Sequence
<220> FEATURE:
<223> OTHER INFORMATION: Synthetic primer

<400> SEQUENCE: 26
gccggctcga gtgtacaaaa                                        20

<210> SEQ ID NO 27
<211> LENGTH: 47
<212> TYPE: DNA
<213> ORGANISM: Artificial Sequence
<220> FEATURE:
<223> OTHER INFORMATION: Synthetic primer

<400> SEQUENCE: 27
aatgatacgg cgaccaccga gatctacacc gactcggtgc cactttt          47

<210> SEQ ID NO 28
<211> LENGTH: 53
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (26)..(30)
<223> OTHER INFORMATION: n is a, c, g, or t

<400> SEQUENCE: 28
caagcagaag acggcatacg agatcnnnnn tttcttgggt agtttgcagt ttt   53

```
<210> SEQ ID NO 29
<211> LENGTH: 67
<212> TYPE: DNA
<213> ORGANISM: Artificial Sequence
<220> FEATURE:
<223> OTHER INFORMATION: Synthetic primer

<400> SEQUENCE: 29
cggtgccact ttttcaagtt gataacggac tagccttatt ttaacttgct atttctagct    60
ctaaaac                                                              67

<210> SEQ ID NO 30
<211> LENGTH: 71
<212> TYPE: DNA
<213> ORGANISM: Artificial Sequence
<220> FEATURE:
<223> OTHER INFORMATION: Synthetic primer

<400> SEQUENCE: 30
tttcaagtta cggtaagcat atgatagtcc attttaaaac ataattttaa aactgcaaac    60
tacccaagaa a                                                         71

<210> SEQ ID NO 31
<211> LENGTH: 18
<212> TYPE: DNA
<213> ORGANISM: Artificial Sequence
<220> FEATURE:
<223> OTHER INFORMATION: Synthetic primer

<400> SEQUENCE: 31
ctcggtgcca cttttttca                                                 18

<210> SEQ ID NO 32
<211> LENGTH: 48
<212> TYPE: DNA
<213> ORGANISM: Artificial Sequence
<220> FEATURE:
<223> OTHER INFORMATION: Synthetic primer

<400> SEQUENCE: 32
caagcagaag acggcatacg agatcttcaa gttgataacg gactagcc                 48
```